US007904139B2

(12) United States Patent
Chance

(10) Patent No.: US 7,904,139 B2
(45) Date of Patent: *Mar. 8, 2011

(54) OPTICAL EXAMINATION OF BIOLOGICAL TISSUE USING NON-CONTACT IRRADIATION AND DETECTION

(75) Inventor: Britton Chance, Marathon, FL (US)

(73) Assignee: Non-Invasive Technology Inc., Philadelphia, PA (US)

( * ) Notice: Subject to any disclaimer, the term of this patent is extended or adjusted under 35 U.S.C. 154(b) by 339 days.

This patent is subject to a terminal disclaimer.

(21) Appl. No.: 11/203,826

(22) Filed: Aug. 13, 2005

(65) Prior Publication Data

US 2006/0058683 A1    Mar. 16, 2006

Related U.S. Application Data

(63) Continuation-in-part of application No. 10/752,440, filed on Jan. 5, 2004, and a continuation-in-part of application No. 10/618,579, filed on Jul. 10, 2003, now abandoned, which is a continuation-in-part of application No. 09/383,476, filed on Aug. 26, 1999, now Pat. No. 6,949,081.

(60) Provisional application No. 60/438,229, filed on Jan. 4, 2003.

(51) Int. Cl.
*A61B 6/00* (2006.01)
(52) U.S. Cl. .......... 600/476; 600/407; 600/473; 600/477
(58) Field of Classification Search .................. 600/407, 600/473, 476, 477
See application file for complete search history.

(56) References Cited

U.S. PATENT DOCUMENTS

| 2,706,927 | A | 4/1955 | Wood ............................. 600/344 |
| 2,790,438 | A | 4/1957 | Taplin et al. .................. 600/344 |
| 3,068,742 | A | 12/1962 | Hicks, Jr. et al. ............. 600/339 |
| 3,412,729 | A | 11/1968 | Smith, Jr. ...................... 600/324 |
| 3,461,856 | A | 8/1969 | Polanyi ......................... 600/323 |
| 3,638,640 | A | 2/1972 | Shaw ............................ 600/323 |
| 3,704,706 | A | 12/1972 | Herczfeld et al. ............ 600/324 |
| 3,709,612 | A | 1/1973 | Clemens ....................... 356/407 |
| 3,866,599 | A | 2/1975 | Johnson ........................ 600/342 |
| 3,994,585 | A | 11/1976 | Frey .............................. 356/40 |
| 3,998,550 | A | 12/1976 | Konishi et al. ................. 356/39 |

(Continued)

OTHER PUBLICATIONS

Brehm, Denise; "Researchers employ infrared imaging for tumor detection," Sep. 24, 1997. MIT Tech Talk. http://web.mit.edu/newsoffice/1997/infrared-0924.html.*

(Continued)

*Primary Examiner* — Tse Chen
*Assistant Examiner* — James Kish
(74) *Attorney, Agent, or Firm* — Ivan D. Zitkovsky

(57) ABSTRACT

An optical system for examination of biological tissue includes a light source, a light detector, optics and electronics. The light source generates a light beam, transmitted to the biological tissue, spaced apart from the source. The light detector is located away (i.e., in a non-contact position) from the examined biological tissue and is constructed to detect light that has migrated in the examined tissue. The electronics controls the light source and the light detector, and a system separates the reflected photons (e.g., directly reflected or scattered from the surface or superficial photons) from the photons that have migrated in the examined tissue. The system prevents detection of the "noise" photons by the light detector or, after detection, eliminates the "noise" photons in the detected optical data used for tissue examination.

35 Claims, 30 Drawing Sheets

U.S. PATENT DOCUMENTS

| | | | |
|---|---|---|---|
| 4,014,321 A | 3/1977 | March | 600/319 |
| 4,029,085 A | 6/1977 | DeWitt et al. | 600/315 |
| 4,086,915 A | 5/1978 | Kofsky et al. | 600/330 |
| 4,119,406 A | 10/1978 | Clemens | 422/81 |
| 4,129,125 A | 12/1978 | Lester et al. | 600/484 |
| 4,138,727 A | 2/1979 | Mantz | 708/813 |
| 4,162,405 A | 7/1979 | Chance et al. | 424/9.6 |
| 4,167,331 A | 9/1979 | Nielsen | 356/39 |
| 4,222,389 A | 9/1980 | Rubens | 600/328 |
| 4,223,680 A | 9/1980 | Jobsis | 600/324 |
| 4,224,948 A | 9/1980 | Cramer et al. | 600/503 |
| 4,259,963 A | 4/1981 | Huch | 600/359 |
| 4,266,554 A | 5/1981 | Hamaguri | 600/323 |
| 4,281,645 A | 8/1981 | Jobsis | 600/324 |
| 4,321,930 A | 3/1982 | Jobsis et al. | 600/344 |
| 4,380,240 A | 4/1983 | Jobsis et al. | 600/344 |
| 4,416,285 A | 11/1983 | Shaw et al. | 600/339 |
| 4,447,884 A | 5/1984 | Wada | 702/131 |
| 4,452,250 A | 6/1984 | Chance et al. | 600/410 |
| 4,469,107 A | 9/1984 | Asmar et al. | 600/494 |
| 4,510,938 A | 4/1985 | Jobsis et al. | 600/344 |
| 4,515,165 A | 5/1985 | Carroll | 600/475 |
| 4,576,173 A | 3/1986 | Parker et al. | 600/317 |
| 4,612,938 A | 9/1986 | Dietrich et al. | 600/476 |
| 4,616,657 A * | 10/1986 | Stoller | 600/475 |
| 4,648,892 A | 3/1987 | Kittrell et al. | 65/387 |
| 4,655,225 A | 4/1987 | Dahne et al. | 600/316 |
| 4,700,708 A | 10/1987 | New, Jr. et al. | 600/331 |
| 4,714,341 A | 12/1987 | Hamaguri et al. | 356/41 |
| 4,738,267 A | 4/1988 | Lazorthes et al. | 600/561 |
| 4,773,422 A | 9/1988 | Isaacson et al. | 600/326 |
| 4,774,679 A | 9/1988 | Carlin | 702/41 |
| 4,800,495 A | 1/1989 | Smith | 600/322 |
| 4,800,885 A | 1/1989 | Johnson | 600/330 |
| 4,805,623 A | 2/1989 | Jobsis | 600/328 |
| 4,807,637 A | 2/1989 | Bjorkholm | 600/476 |
| 4,824,242 A | 4/1989 | Frick et al. | 356/41 |
| 4,836,207 A | 6/1989 | Bursell et al. | 600/318 |
| 4,846,183 A | 7/1989 | Martin | 600/336 |
| 4,869,254 A | 9/1989 | Stone et al. | 600/336 |
| 4,880,304 A | 11/1989 | Jaeb et al. | 356/41 |
| 4,908,762 A | 3/1990 | Suzuki et al. | 600/407 |
| 4,926,867 A | 5/1990 | Kanda et al. | 600/334 |
| 4,937,526 A | 6/1990 | Ehman et al. | 324/309 |
| 4,940,453 A | 7/1990 | Cadwell | 600/13 |
| 4,951,682 A | 8/1990 | Petre | 600/526 |
| 4,972,331 A | 11/1990 | Chance | 600/310 |
| 5,035,243 A | 7/1991 | Muz | 600/344 |
| 5,057,695 A | 10/1991 | Hirao et al. | 250/575 |
| 5,062,431 A | 11/1991 | Potter | 600/478 |
| 5,088,493 A | 2/1992 | Giannini et al. | 600/323 |
| 5,090,415 A | 2/1992 | Yamashita et al. | 600/476 |
| 5,106,387 A | 4/1992 | Kittrell et al. | 606/15 |
| 5,119,815 A | 6/1992 | Chance | 600/433 |
| 5,122,974 A | 6/1992 | Chance | 600/323 |
| 5,137,355 A | 8/1992 | Barbour et al. | 356/342 |
| 5,139,025 A | 8/1992 | Lewis et al. | 600/477 |
| 5,143,081 A | 9/1992 | Young et al. | 600/554 |
| 5,158,090 A | 10/1992 | Waldman et al. | 600/473 |
| 5,174,298 A | 12/1992 | Dolfi et al. | 600/425 |
| 5,178,142 A | 1/1993 | Harjunmaa et al. | 600/310 |
| 5,187,672 A | 2/1993 | Chance et al. | 600/407 |
| 5,190,039 A | 3/1993 | Takeuchi et al. | 600/311 |
| 5,198,977 A | 3/1993 | Salb | 382/128 |
| 5,203,339 A | 4/1993 | Knuttel et al. | 600/425 |
| 5,213,105 A | 5/1993 | Gratton et al. | 600/473 |
| 5,218,962 A | 6/1993 | Mannheimer et al. | 600/331 |
| 5,257,202 A | 10/1993 | Feddersen et al. | 702/32 |
| 5,277,181 A | 1/1994 | Mendelson et al. | 600/322 |
| 5,287,276 A | 2/1994 | Crawford et al. | 378/4 |
| 5,300,097 A | 4/1994 | Lerner et al. | 607/93 |
| 5,309,907 A | 5/1994 | Fang et al. | 600/342 |
| 5,309,912 A | 5/1994 | Knuttel | 600/425 |
| 5,353,799 A | 10/1994 | Chance | 600/473 |
| 5,358,503 A | 10/1994 | Bertwell et al. | 606/27 |
| 5,402,778 A | 4/1995 | Chance | 600/310 |
| 5,408,093 A | 4/1995 | Ito et al. | 250/227.26 |
| 5,413,098 A | 5/1995 | Benaron | 600/310 |
| 5,416,582 A | 5/1995 | Knutson et al. | 356/484 |
| 5,431,170 A | 7/1995 | Mathews | 600/479 |
| 5,494,032 A | 2/1996 | Robinson et al. | 600/323 |
| 5,497,769 A | 3/1996 | Gratton et al. | 600/323 |
| 5,551,422 A | 9/1996 | Simonsen et al. | 600/322 |
| 5,551,423 A | 9/1996 | Sugiura | 600/476 |
| 5,596,987 A | 1/1997 | Chance | 600/310 |
| 5,625,458 A | 4/1997 | Alfano et al. | 356/446 |
| 5,655,530 A | 8/1997 | Messerschmidt | 600/366 |
| 5,673,701 A | 10/1997 | Chance | 600/473 |
| 5,706,821 A | 1/1998 | Matcher et al. | 600/310 |
| 5,779,631 A | 7/1998 | Chance | 600/328 |
| 5,782,755 A | 7/1998 | Chance et al. | 600/322 |
| 5,807,263 A * | 9/1998 | Chance | 600/476 |
| 5,845,639 A | 12/1998 | Hochman et al. | 600/407 |
| 5,930,330 A * | 7/1999 | Wolfe et al. | 378/98.2 |
| 5,943,133 A | 8/1999 | Zeylikovich et al. | 356/496 |
| 5,949,077 A | 9/1999 | Alfano et al. | 250/459.1 |
| 5,952,664 A * | 9/1999 | Wake et al. | 250/459.1 |
| 5,983,125 A | 11/1999 | Alfano et al. | 600/473 |
| 5,987,351 A | 11/1999 | Chance | 600/473 |
| 5,995,856 A | 11/1999 | Mannheimer et al. | 600/322 |
| 6,006,001 A | 12/1999 | Alfano et al. | 385/115 |
| 6,058,324 A | 5/2000 | Chance | 600/473 |
| 6,091,983 A | 7/2000 | Alfano et al. | 600/431 |
| 6,108,576 A | 8/2000 | Alfano et al. | 600/476 |
| 6,175,759 B1 * | 1/2001 | Chan et al. | 600/431 |
| 6,201,989 B1 | 3/2001 | Whitehead et al. | 600/476 |
| 6,215,587 B1 | 4/2001 | Alfano et al. | 359/368 |
| 6,230,046 B1 * | 5/2001 | Crane et al. | 600/476 |
| 6,240,309 B1 * | 5/2001 | Yamashita et al. | 600/407 |
| 6,813,440 B1 * | 11/2004 | Yu et al. | 396/14 |
| 6,917,038 B2 * | 7/2005 | Zheng et al. | 250/339.04 |
| 7,113,817 B1 * | 9/2006 | Winchester et al. | 600/476 |
| 7,610,082 B2 | 10/2009 | Chance | 600/475 |
| 2002/0099295 A1 | 7/2002 | Gil et al. | |
| 2003/0012253 A1 | 1/2003 | Pavlidis | |
| 2003/0018271 A1 * | 1/2003 | Kimble | 600/473 |
| 2004/0010192 A1 * | 1/2004 | Benaron et al. | 600/431 |
| 2004/0215082 A1 * | 10/2004 | Chance | 600/473 |
| 2005/0154290 A1 * | 7/2005 | Langleben | 600/410 |

OTHER PUBLICATIONS

Ntziachristos et al., "Concurrent MRI and diffuse optical tomography of breast after indocyanine green enhancement." Mar. 14, 2000, PNAS, vol. 97, No. 6, p. 2767-2772.*

* cited by examiner

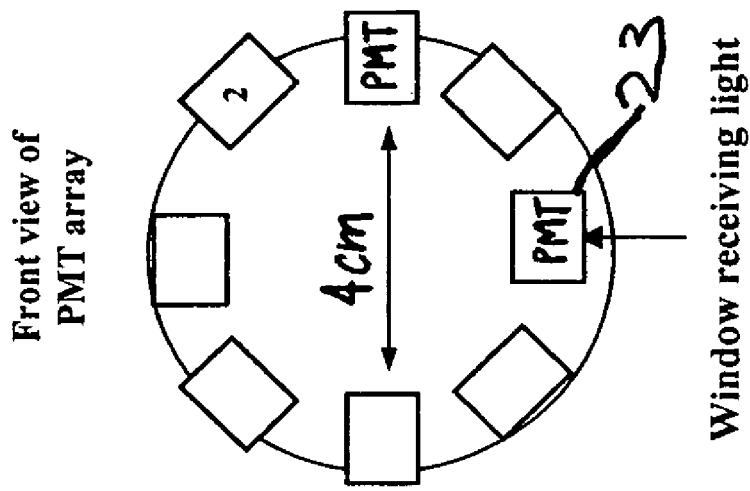
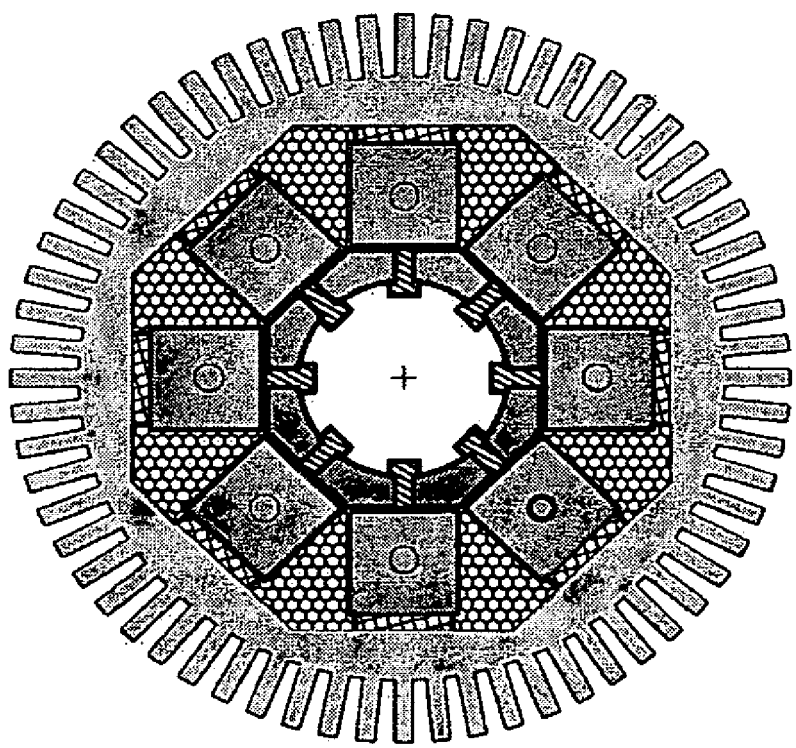
Fig.2A-II

OXYGENATION CHANGES

BLOOD VOLUME CHANGES

OXYGENATION
SUBJECT TELLS THE TRUTH

OXYGENATION
SUBJECT TELLS A LIE

EVENT RELATED IMAGE:
15 SECONDS AFTER SUDDEN INSIGHT MINUS
15 SECONDS BEFORE SUDDEN INSIGHT

OXYGENATION

OPTICAL EXAMINATION OF BIOLOGICAL TISSUE USING NON-CONTACT IRRADIATION AND DETECTION

This application is a continuation-in-part of U.S. application Ser. No. 10/752,440, filed on Jan. 5, 2004, entitled "Examination of Biological Tissue using Non-Contact Optical Probes," which claims priority from U.S. Provisional Application 60/438,229, filed on Jan. 4, 2003 now abandoned; and is also a continuation-in-part of U.S. application Ser. No. 10/618,579, filed on Jul. 10, 2003, entitled "Examination and Imaging of Brain Cognitive Functions," all of which are incorporated by reference. This application is also a continuation-in-part of U.S. application Ser. No. 09/383,476, filed on Aug. 26, 1999 now U.S. Pat. No. 6,949,081, entitled "Sensing and Interactive Drug Delivery," which is incorporated by reference.

The present invention relates to in vivo non-invasive examination or imaging of biological tissue including tissue models used to study pathological tissue conditions and diseases including the effects of drug agents thereon.

BACKGROUND OF THE INVENTION

X-ray or γ-ray radiation, optical radiation, ultrasound waves and magnetic field have been used to examine and image biological tissue. X-rays or γ-rays propagate in the tissue on straight, ballistic lines, that is, their scattering is negligible. Thus, imaging is based on evaluation of the absorption levels of different tissue types. For example, in roentgenography the X-ray film contains darker and lighter spots: the denser bone that the X-rays cannot travel through, and the muscle, fat and tissue the X-rays can easily travel through. In more complicated systems, such as computerized tomography (CT), a cross-sectional picture of human organs is created by transmitting X-ray radiation through a section of the human body at different angles and by electronically detecting the variation in X-ray transmission. The detected intensity information is digitally stored in a computer that reconstructs the X-ray absorption of the tissue at a multiplicity of points located in one cross-sectional plane. Similar things can be done with different types of radiation, where radiation absorption levels of molecules within a tissue can reveal structure, or changes in concentrations of absorbing molecules, therefore showing changes in some aspect of the metabolism of the tissue.

Near infrared radiation (NIR) has been used to study biological tissues non-invasively, including oxygen metabolism in the brain, finger, or ear lobe, for example. The use of visible, NIR and infrared (IR) radiation for medical imaging may have several advantages over other forms of radiation: In the NIR or IR range the contrast factor between a tumor and a surrounding tissue is much larger than in the X-ray range. In addition, the visible to IR radiation is preferred over the X-ray radiation since it is non-ionizing and thus, generally causes fewer side effects. However, the visible or IR radiation is strongly scattered and absorbed in biological tissue, and the migration path cannot be approximated by a straight line, making inapplicable certain aspects of cross-sectional imaging techniques.

NIR spectrometry adapted to the principles of computerized tomography has been used for in vivo imaging. This technique utilizes NIR radiation in an analogous way to the use of X-ray radiation in an X-ray CT. The X-ray source is replaced by several laser diodes (or other light sources) emitting light in the NIR range. The NIR-CT uses a set of photodetectors that detect the light that had migrated in the imaged tissue. The detected data are manipulated by a computer in a manner similar to the detected X-ray data in an X-ray CT. Different NIR-CT systems have recognized the scattering aspect of the non-ionizing radiation and have modified the X-ray CT algorithms accordingly.

Together with intensive theoretical derivations and data acquisition protocols at many source-detector positions, the NIR field has been brought to the point where further development of 3D image resolution and achievement of improved signal-to-noise ratio is limited by the sensor/subject coupling in number, accuracy and reproducibility. The congestion of the subject's head, breast or limb due to a large number of optical coupling devices, particularly for in-magnet imaging of breast cancers, reaches the limit of convenience and accessibility. Furthermore, the uncontrolled contact positions of such fibers to the tissue, particularly the breast, have become one of the principal sources of irreproducibility in data acquisition. While compression, matching fluids, and probes are currently used, many problems could be solved if the test object could be viewed from afar in a non-intrusive, untethered fashion, particularly if the source position and detector acquisition could be consistently aimed or rapidly scanned over the tissue for multi-site data acquisition.

Brain tissue has been particularly studied by many burgeoning technologies, wherein MRI is truly versatile as being capable of imaging hemodynamic and metabolic signals in a unique fashion. Positron emission tomography (PET) has similar possibilities of large chemical specificity governed by the combination of lifetimes and radiation from radioactive isotopes. Other methods give highly specialized signals, for example, magnetoencephalography (MEG) and electronencephalography (EEG), which have respectively high and low resolution for neurophysiological signals. Optical tomography is somewhat more quantitative with respect to hemodynamic changes and has latent possibilities for measuring neuronal signals.

Furthermore, the propagation of near infrared light through tissue such as the brain and breast has been experimentally studied and theoretically modeled. Accurate theoretical models are based on Monte Carlo methods for statistical physics and the diffusion equation and on analytic expressions that show propagation into the gray matter of the brain in adults and especially in neonates. This propagation of light into cranial tissue has been verified by clinical measurements of the presence of X-ray CT-identified cranial hematomas at depths of about 3-4 cm. Detection of the oxygenation state and amount of hemoglobin has been the goal of tissue oximetry and quantitative results are obtained by time and frequency domain devices. However, single volume determination of optical parameters of a highly heterogeneous system such as the human brain may give only a fraction of the signal of a localized focal activation already shown to be highly localized by fMRI (functional magnetic resonance imaging).

The way optical spectroscopy has been used to quantitatively monitor and image tissue blood oxygenation and volume is by measuring absorption of oxyhemoglobin and deoxyhemoglobin in the NIR wavelength region: below 700 nm, light is strongly absorbed by hemoglobin, and above 900 nm, it is strongly absorbed by water. By making differential measurements at either side of the isosbestic point of oxyhemoglobin and deoxyhemoglobin absorbance (near 800 nm), it is possible to quantify the blood oxygenation and volume levels. Typically, these measurements are made at 750 nm and 830 nm.

Lastly, optical systems are relatively simple, safe, portable and affordable as required by today's health care industry. There are several optical examination and imaging devices that have been used for imaging functional activity of adult, full-term and pre-term neonate brain. These optical examination and imaging systems are described in U.S. Pat. Nos. 5,353,799; 5,853,370; 5,807,263, 5,820,558, which are incorporated by reference. These optical systems do not require subject immobilization (as do MRI and PET), nor do they require multisubject averaging of data. The images are acquired in less than half a minute and show two-dimensional resolution of blood changes to better than a centimeter. In these optical systems, however, light sources and light detectors are mounted directly next to the examined tissue or the light is coupled to the tissue using light guides (e.g., optical fibers). In these optical systems, however, the subject has to wear the optical coupler or probe. Furthermore, the optical probe has to provide electrical insulation to prevent electrical shock to the subject.

There is still a need for optical examination and imaging systems for examining various types of biological tissue including the brain or breast tissue, which the present invention manages to fulfill.

SUMMARY OF THE INVENTION

The present invention relates to non-invasive optical examination or imaging of biological tissue including tissue models used to study pathological tissue conditions and diseases including the effects of drug agents thereon. This is performed preferably in vivo, using non-contact spectroscopic systems, but contact irradiation or detection depending on the examined tissue and the ability to effectively deliver and collect light to and from the tissue. The examined biological tissue is human tissue, animal tissue or model, or generally any tissue model.

The described systems perform non-invasive optical examination and imaging including molecular imaging and functional imaging.

According to one aspect, an optical system for examination of biological tissue includes a light source, a light detector, optics and electronics. The light source generates a light beam, transmitted to the biological tissue, spaced apart from the source. The light detector is located away (i.e., in a non-contact position) from the examined biological tissue and is constructed to detect light that has migrated in the examined tissue. The electronics controls the light source and the light detector, and a system separates the reflected photons (e.g., directly reflected or scattered from the surface or superficial photons) from the photons that have migrated in the examined tissue. The system prevents detection of the "noise" photons by the light detector or, after detection, eliminates the "noise" photons in the detected optical data used for tissue examination.

The light source launches photons through the skin, skull and arachnoid space where they are highly diffused due to scattering events. A fraction of the photons emerge within the solid angle of the detector, and a number of source-detector couplings sample the region of interest. The incremental modulation of the signals, which is due to activation of metabolism or alterations of blood flow, causes a differential attenuation between particular light sources and detectors. This incremental attenuation, approximately a 1% change, can be detected with a stable light source and a sensitive detector followed by a low-noise amplifier.

The optical system, including its electronics, may comprise a time resolved spectroscopic (TRS) system, a phase modulation system (PMS), a phase array system, or a continuous wave (CW) system. In each case, the detector is located away from the examined tissue and there is no optical fiber in contact with the tissue surface. Conventionally, this reduces the light collection efficiency (reduces the effective numerical aperture), which in prior art was considered as a barrier to an effective spectrophotometric system. Thus, the present invention discards the conventional concept.

According to another aspect, an optical system for examination of brain tissue of a subject undergoing a security check includes a light source, a light detector, optics and electronics. The light source generates a light beam, transmitted to the head of the subject spaced apart from the source. The light detector is located away from the head and is constructed to detect light that has migrated in the tissue being examined. The electronics controls the light source and the light detector, and a system separates the reflected photons from the photons that have migrated in the examined tissue to prevent detection of the reflected photons by the light detector or eliminate after detection the reflected photons in the detected optical data used for tissue examination.

Preferred embodiments of these aspects include one or more of the following features: The optical system includes a lens associated with the light detector (e.g., a fresnel lens for a CW system, or a cassegrain lens). The light detector includes a charge coupled device (CCD), an intensified charge coupled device (ICCD) or other types of detectors, for example, detectors used in Computed Tomography (CT). The number of source detector positions is limited mainly by the excitation spot size and by the resolution of the detectors. The light source is associated with a scanning system for scanning the emitted light beam over a tissue.

According to another aspect, the non-contact optical system is used for molecular imaging, for example, by following particular processes via tracking byproducts of catabolism or anabolism (metabolic processes) of cellular compounds in the cell, wherein such byproducts a have different optical properties.

According to another aspect, the non-contact optical system is used for tracking medical processes associated with progress of diseases and treatment. The TRS, PMS or CW systems detect and quantify naturally occurring or injected compounds and their metabolites based on their optical properties, or metabolites of chemical or pharmacological agents based on their optical properties.

The TRS, PMS or CW systems are used for tracking medical processes associated with progress of diseases and treatment via detection and quantification of injected compounds and their metabolites via their optical properties. Optionally, a specific compound is tagged for detection.

The TRS, PMS or CW systems are used for functional imaging and non-invasively monitoring physiological processes in the examined tissue, primarily based on blood flow and cellular metabolism. The molecular imaging may further image one or several selected, targeted processes and pathways in the examined tissues, including cells within the tissue. The molecular imaging may further measure absorption and scattering properties, fluorescence intensity and fluorescence lifetime to provide tissue characteristics and improve contrast of the collected image and analyze metabolism of pharmacological agents and their effect in medical treatment. The optical systems can detect changes in tissue pH.

In general, there are three types of optical systems suitable for remote delivery and/or sensing of visible or NIR signals:

1. Time Resolution System (TRS). This is a system in which time resolution of specular and diffusive photons is made on a time basis. A pulsed oscillator at 50 MHz activates a series of laser diodes at the desired wavelength with 10% duty ratio and illuminates the desired targets, (prefrontal cortex, or PFC, breast, muscle) through the appropriate optical system. The emergent photons are detected through wide band PMT that allows discrimination of reflected and diffusive photons. The decay of intensity is followed and processed with either time correlated single photon counting (TCSPC) or a boxcar detector. No blocking filters are needed to eliminate overload due to reflected photons in this system.

The system functions by remote detection of photon migration signals from breast and brain, which affords non-contact spectroscopy and imaging of functional activity in physiological and pathological states with an NIR optical system at a distance of over two meters by employing an efficient optical system (>10% solid angle) of the backscattered photons, thereby affording unobtrusive, untethered detection of hemodynamic parameters in localized regions. While in many cases the subject is stationary, a galvanometer-activated mirror-tracking system can be used for a moving target and, furthermore, TRS. The problem of separating specular reflections from migrating photons is dealt with at a few levels: First, by using fluorescence imaging with an effective secondary filter protecting the detector system. Second, by using time resolved or frequency resolved recording so that the early reflected photons are separated from the subsequently diffusing photons. Third, by using crossed polaroids on the source and detector. Fourth, using an optical system, either refractive or reflective, which will incorporate aperture stops in order to better separate reflected from back-scattered photons.

2. Phase Modulation System (PMS) or Phase Array System. In this case, sine wave modulated sources at variable frequencies are required for illumination of the typical target via blocking filters or polarizers. The emergent photons are detected with a narrow-band detector of variable frequency. Signal detection occurs in a wide band phase detector which may or may not be a network analyzer, but essential phase lock with a transmitter is required. The blocking filters may be polarizers or excitation/emission fluorescent filters.

The system by the Network for Transitional Research for Optimal Imaging (NTROI) is a frequency domain system of this sort, which our group is helping develop. The system has sine wave modulated sources, driven by variable frequency oscillators in the range of 50 to 500 MHz. The PFC, breast or muscle is illuminated through a narrow-band optical filter or a polarizer, or both, and the emergent photons are viewed through a cross-polarizer or a tight secondary filter illuminating specular reflection signals. The detector is narrow-banded at the particular frequency, which is variable over the range of 50 to 500 MHz. A wide-band phase detector, sometimes termed a network analyzer, must be phase locked to the sine wave modulator for the light source.

3. Continuous Wave System. The CW system has CW sources which may be time shared or frequency shared, and blocking filters or polarizers illuminating the typical targets: PFC, breast, or muscle. In the case of blocking filters, only one wavelength is used. The diffusive radiation is detected in a narrow-band detector and separated from blocking filters or polarizers for the detector. The detector is protected from specular reflection by cross-polarization, plus a blocking filter, as may be necessary to eliminate specular reflection. The detector is narrow-band, either at a variety of frequencies for multi-wavelength elimination, or time multiplex. It should be noted that there must be phase lock or time lock coupling between the CW sources and the narrow-band detectors.

While timesharing of CW systems and frequency domain systems (such as PMS) is usually in the kilohertz region, the TRS system intrinsically employs time-sharing in the megahertz region, with activating flashes every 20 ns. Usually, the high repetition rate data can be stored in the boxcar integrators until the signal-to-noise ratio requirements are satisfied. The actual time resolution is set by the choice if time constants employed for the integrators and the frequency with which analog-to-digital converter (ADC) interrogates the integrators. The software can be arranged to average over any desired interval that gives a suitable signal-to-noise ratio.

Undoubtedly, the CW system is the simplest, with the frequency domain systems (such as PMS) having to solve the difficult problem of phase locking at the various frequencies employed. These three systems are suitable for the test systems and for the special purpose systems described below.

In studying brain tissues, signals obtained by the system can be of several types: one is a conventional signal, or "hemodynamic" signal, caused by the augmentation of blood flow activated by neuronal function based on blood oxygenation as measured by oxy and deoxyhemoglobin, the states of hemoglobin, the molecule that carries oxygen in the blood. The second type of signal is of a completely different nature and is due to an incremental change of metabolism, such as might be caused by a functional activation of neuronal activity, causing breakdown of ATP and formation of ADP and inorganic phosphate.

The first type of signal, or "hemodynamic" signal, is measured at the isosbestic point of oxy and deoxyhemoglobin, the states of hemoglobin, where both states of hemoglobin have the same absorption coefficient. Therefore, measurement of absorption measures total blood levels, and is indicated by a simple rise in absorption at that wavelength, unaffected by the ratio of oxy to deoxyhemoglobin blood volume. In addition, an appropriate fraction of the change at 724 and 850 nm gives, over a limited range, the incremental absorption similar to that at 805 nm due to the hemodynamics of response to critical function. It is generally acknowledged that the "hemodynamic signal" has all of the problems of the blood oxygenation level dependent (BOLD) signal. Namely, it is a "downstream" signal, activated by chemical messengers from the region under activation; for example, adenosine monophosphate (AMP), formed from adenosine diphosphate (ADP) generated in response to neuronal breakdown of adenosine triphosphate (ATP). Therefore, the hemodynamic signal is delocalized and is likely to be found downstream of the point where activation is maximal.

The second type, or metabolic signal, is generally based on the breakdown of ATP and formation of ADP and inorganic phosphate. As waste products, ADP and phosphate act as stimulants of respiration for neuronal mitochondria and are responsible for increased oxygen intake from circulating hemoglobin through the oxygen gradient that exists between neuronal mitochondria and the adjacent capillary bed. Thus the oxyhemoglobin of the capillary bed becomes deoxygenated to an extent, depending upon the activation of respiration, the blood flow through the capillaries, and generally, the ratio of capillary volume to mitochondrial volume. This second signal is thus a good measure of brain energy use.

Generally, a system and method for examining brain function of a subject introduces optical radiation from a light source into the brain of a subject and detects radiation that has migrated in a brain region from the light source to a detector. The system may also optionally provide brain stimulation: either visual, auditory, or cognitive stimulation. The system evaluates the detected radiation to determine brain function of a subject. According to another embodiment, this can be used to test malevolence of the subject: The system data is evaluated to determine truthfulness of statements by the subject, for example, based on a test where some type of stimulation has been provided. Furthermore, the described system can be used as a "deceit measure detector" that provides a strong signal at the signature voxel when the subject is lying and provides a weak signal at the signature voxel when the subject is telling the truth.

In the case of breast cancer detection, the convenient activation processes described for the brain are not available for the hemoglobin signal. The spatial distribution of blood volume and hemodynamic signals are the two intrinsic signals available. Thus, cancer detection using intrinsic signals depends upon the different localization of hemoglobin deoxygenation due to increased metabolic activity of the cancer and increased blood volume signal due to the increased blood vessel content of the tumor. This proposal emphasizes the TRS system as having particular advantages of time resolution of specular reflection and maximizing the separation between shallow and deep photon migration patterns as well as having the capability to measure different biomedical components at different wavelengths or combinations thereof: hemoglobin, water, lipid, melanin and fluorescent beacons as well. The spatial distribution of blood volume, the oxygenation states of hemoglobin, lipid and water are the "intrinsic" signals available. Thus, cancer detection using intrinsic signals depends upon the localized hemoglobin deoxygenation due to increased metabolic activity of the cancer and increased blood volume signal due to the increase blood vessel content of the tumor. In addition, high sensitivity may be acquired by the use of increased water content and an altered lipid content to increase the sensitivity/specificity of cancer detection. Regarding the fluorescent beacons, the most promising is an activation signal obtained by the intravenous delivery of indocyanine green dye (ICG), or cardiogreen, at approximately 0.2 mg/kg. There will then be incremental fluorescence emission at 830 nm in response to 805 nm excitation in the tumor volume. The use of fluorescence signal with an appropriate secondary filter minimizes the possible interference due to specular reflected photons. Use of this method will increase as molecular beacons specific for particular cancers become both approved by the FDA, and available for clinical studies.

Another important application can be intra-operative monitoring of cardiac surgery. While the heart can withstand ischemia during the surgical procedure itself, the ability to secure a reperfusion without reperfusion injury is often the test of a successful cardiac operation. The remote sensing TRS can display a pattern of the previously ischemic portion of the myocardium and determine the reoxygenation of myoglobin and hemoglobin during the reperfusion interval, which may be delayed or refractory. In this case, the delivery of light pulses is synchronized with systole and diastole to give myocardial oxygenation at these times. In cardiac surgery, interference from room lighting must be avoided by using optical filters, which are effective if fluorescent lights are used. Another application in cardiopulmonary bypass is to monitor the reoxygenation of the brain by scanning the forehead as mentioned above. In both cases, quantitative values of cardiac and brain saturation are obtained from the untethered patient and the fact that fiber coupling to the tissue surface is not necessary will make a significant difference in the applicability of the system.

BRIEF DESCRIPTION OF THE DRAWINGS

FIG. 2A-II illustrates a multiple detector 8 channel PMT array.

FIGS. 4, 4A, 4B, and 4C show schematically a TRS system used for non-contact optical examination or imaging, wherein FIG. 4 is a schematic block diagram of the TRS system using a single boxcar integrator, FIG. 4A is a schematic block diagram of a related TRS system using multiple boxcar integrators, FIG. 4B is a timing diagram for the TRS system of FIG. 4A, and FIG. 4C shows an example of a time resolved spectrum collected by the TRS system of FIG. 4A.

DESCRIPTION OF PREFERRED EMBODIMENTS

The described systems and methods use non-contact (i.e., remote) or contact light coupling in four different embodiments. The first embodiment is a spectroscopic system providing contactless (i.e., non-contact) light irradiation and light detection of photons emanating from the tissue surface. This specification primarily describes this type of optical coupling for tissue examination and imaging. In another embodiment, the optical system utilizes remote irradiation and a contact light collection system touching the tissue surface. In the third embodiment, the optical system uses a contact delivery system (being in contact with the tissue surface) and a remote light collection system. The last embodiment is an optical system utilizing contact irradiation and contact light collection.

Figure 1:
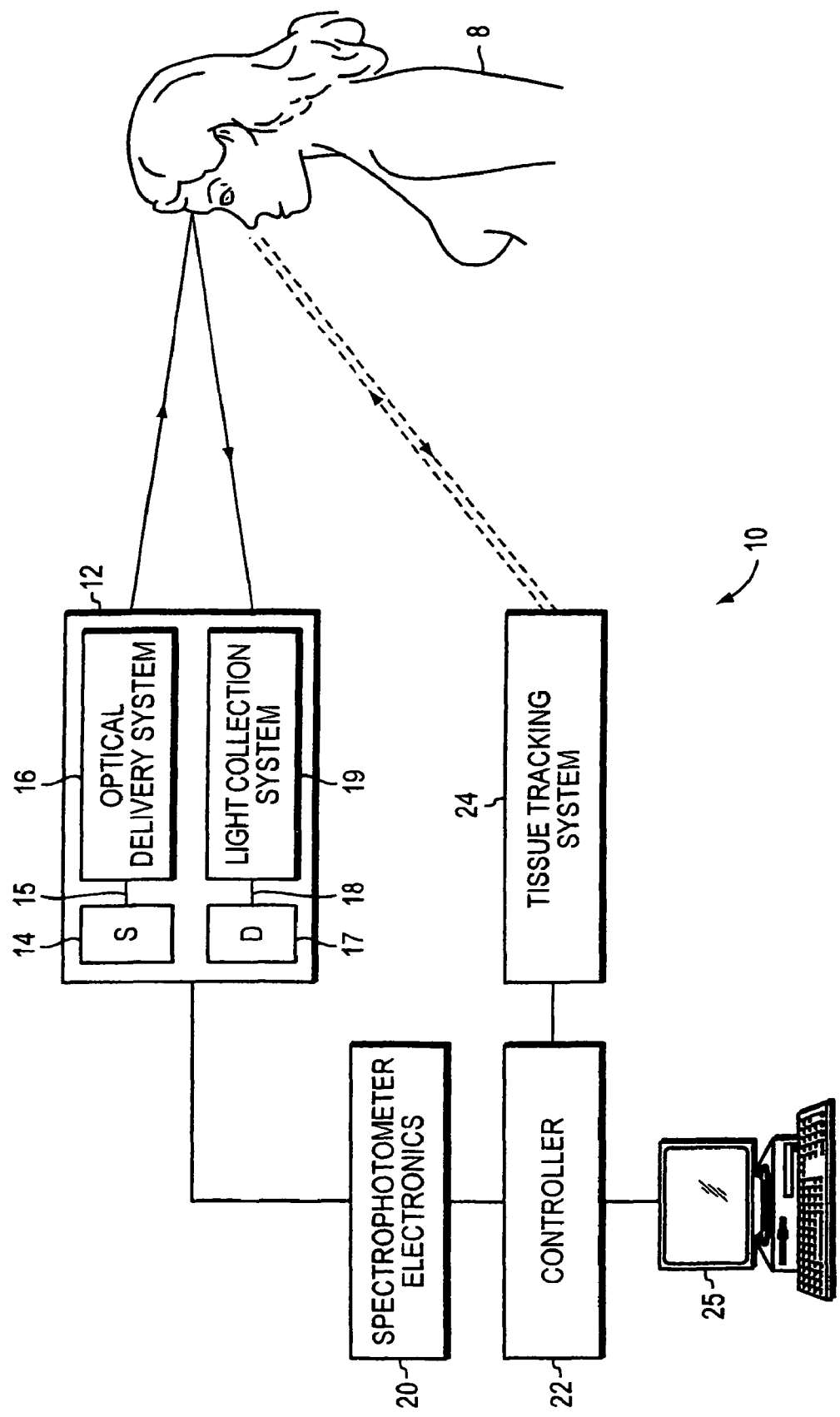
FIG. 1 shows schematically a non-contact optical examination or imaging system having an optical probe, including a light source and a light detector remotely located from the examined biological tissue.

FIG. 1 shows schematically a non-contact optical system 10 including a non-contact optical probe 12, spectrophotometer electronics 20, a system controller 22, a tissue tracking system 24 and a computer 25. Spectrophotometer electronics 20 control optical probe 12, including light emission from a light source 14, light delivery or scanning by an optical delivery system 16, light collection and receiving by a light collection system 19 and the corresponding detection by a light detector 17. Light source 14 emits a light beam of a selected wavelength focused and/or scanned over the examined tissue surface by delivery system 16. Light detector 17 receives light from a light collection system 19, which collects light emanating from the tissue surface. A controller 22 controls the entire operation of the spectrophotometer (including electronics 20 and optical probe 12) and controls operation of a tissue tracking system 24. (Note: while the biological tissue being shown in all cases is human, the biological tissue that can be imaged with this technology can include animal tissues and research animal models.)

Tissue tracking system 24 is optional and operates together with non-contact optical probe 12 by "locating" a selected tissue region, and providing focusing data to the optics of probe 12. The simplest embodiment of tissue tracking system 24 includes an automatic focusing system used in optical cameras or video recorders. Alternatively, tissue tracking system 24 provides a picture or another type of optical image of the tissue of interest to computer 25, wherein the operator can select the irradiation region of the examined tissue surface for light delivery system 16, based on an optical image collected by the tissue tracking system. Alternatively, tissue tracking system 24 may include optics and electronics of an optical or video camera (operating in the visible or infrared range). Tissue tracking system 24 can automatically provide focus and raster information to optical probe 12, accounting for a moving biological tissue of interest during examination and imaging. Even though schematically shown separately, tissue tracking system 24 may be constructed as an integral part of optical probe 12, using even the same light source and detector.

The entire non-contact, remote optical system uses spectrophotometer electronics 20, which may be a CW spectrophotometer described in PCT application PCT/US95/15666, which is incorporated by reference. Alternatively, the spectrophotometer is a TRS system as described in PCT applications PCT/US94/03518 or PCT/US94/07984, or U.S. Pat. No. 5,119,815 or U.S. Pat. No. 5,386,827, all of which are incorporated by reference. In another embodiment, the spectrophotometer is a phase modulation system described in U.S. Pat. Nos. 4,972,331; 5,122,974; 5,187,672; 5,553,614; 5,564,417; PCT application PCT/99/03066; PCT application PCT/99/02953; and PCT application PCT/99/03030, all of which are incorporated by reference. In another embodiment, the spectrophotometer is a phased array, phase cancellation system described in PCT application PCT/US93/05868 or an amplitude cancellation system described in PCT application PCT/US95/15694, both of which are incorporated by reference as if fully set forth herein.

Figure 1A:
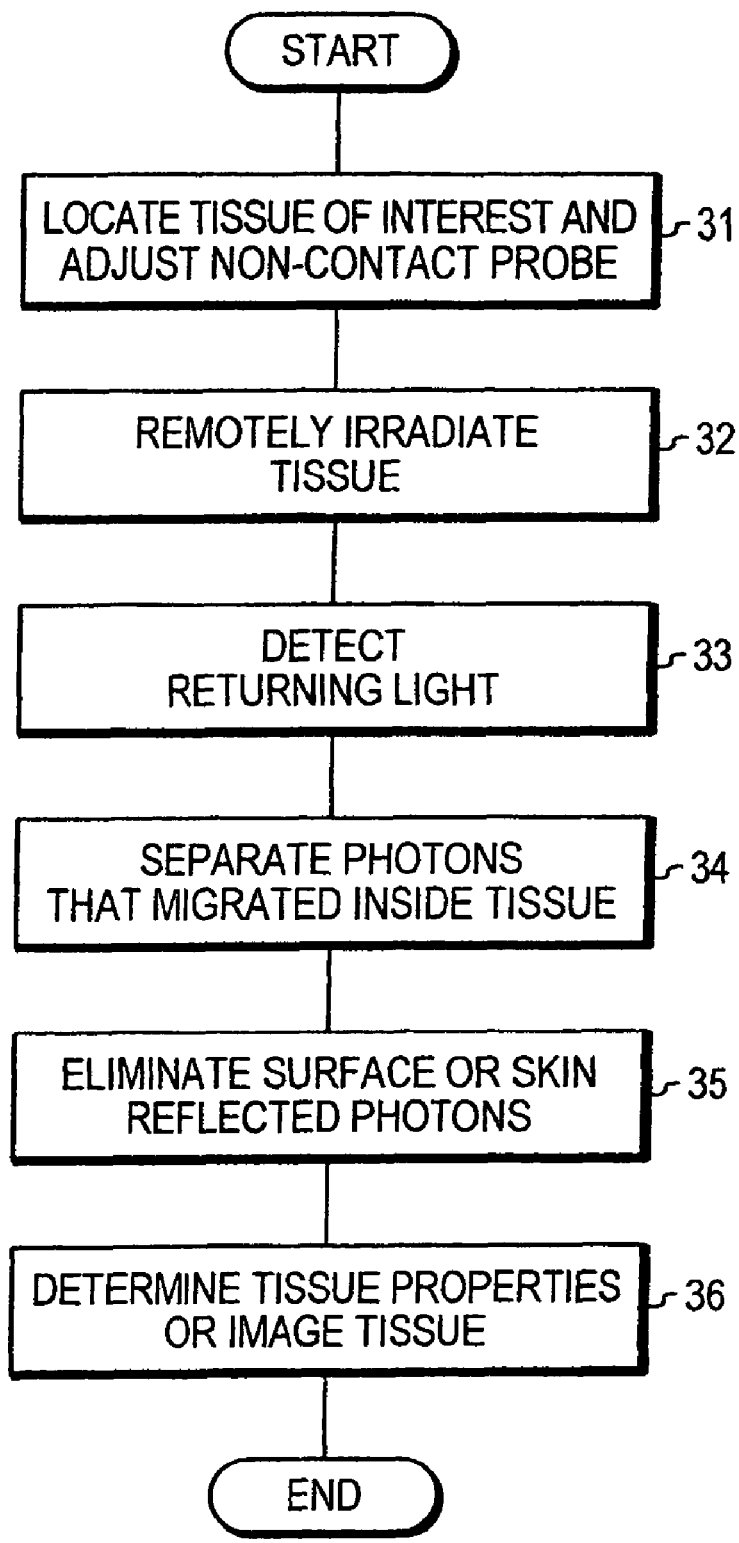
FIG. 1A illustrates schematically an examination or imaging process preformed by the system of FIG. 1.

FIG. 1A illustrates schematically an examination and imaging process performed by the system of FIG. 1. The entire process is controlled by computer 25, which executes all data acquisition and processing algorithms. Initially, tissue tracking system 24 locates a tissue region of interest. The tissue region of interest may be displayed on the monitor of computer 25, and an operator can select the size of the examined region, the raster density and area, the acquisition time and other parameters. Then, tissue tracking system 24 "locks on" the selected tissue area and provides orientation and focusing data to light delivery system 16 and light collection system 19 of non-contact optical probe 12 (step 31).

Light source 14 emits a light beam 15 of a selected wavelength, and optical delivery system 16 scans and/or directs the irradiation light to the selected tissue area (step 32). Light collection system 19 collects the returning light and light detector 17 detects the light provided by light collection system 19, as described below (step 33). In steps 34 and 35, the system separates the "useful" photons that migrated in the examined tissue from the "unwanted" photons returned due to specular reflection or reflection from the skin layers. This separation may be done optically or electronically. Once this is done, tissue properties can be determined using the data (step 36).

The system acquires optically only the "useful" photons, for example, by using confocal detection, polarized light, or detecting fluorescent radiation excited inside the tissue of interest. For example, light source 14 emits a light beam that is polarized by a polarizer (included in optical delivery system 16), which polarized light beam is scanned over the irradiation location of the examined tissue. Reflected photons maintain polarization, while the useful migrating photons lose polarization. Thus, the system can optically eliminate the reflected light. Alternatively, optical delivery system 16 and light collection system 19 include a pinhole for confocal detection (or pseudo-confocal detection) of photons from a selected depth inside the examined tissue. Alternatively, light source 14 emits a light beam of a wavelength selected to excite fluorescent radiation inside the examined tissue. Light collection system 19 includes a suitable interference filter and thus light detector 17 detects the fluorescent light excited inside the examined tissue.

The system separates electronically or computationally the detected signal to receive only the "useful" photons. As described in connection with FIGS. 4, 4A, 4B and 4C, a time resolved spectroscopic system (TRS) eliminates the reflected photons using proper timing of the gates shown in FIG. 4B. The time resolved spectroscopic system of FIG. 5 also eliminates the reflected photons using proper timing.

Figure 1B:
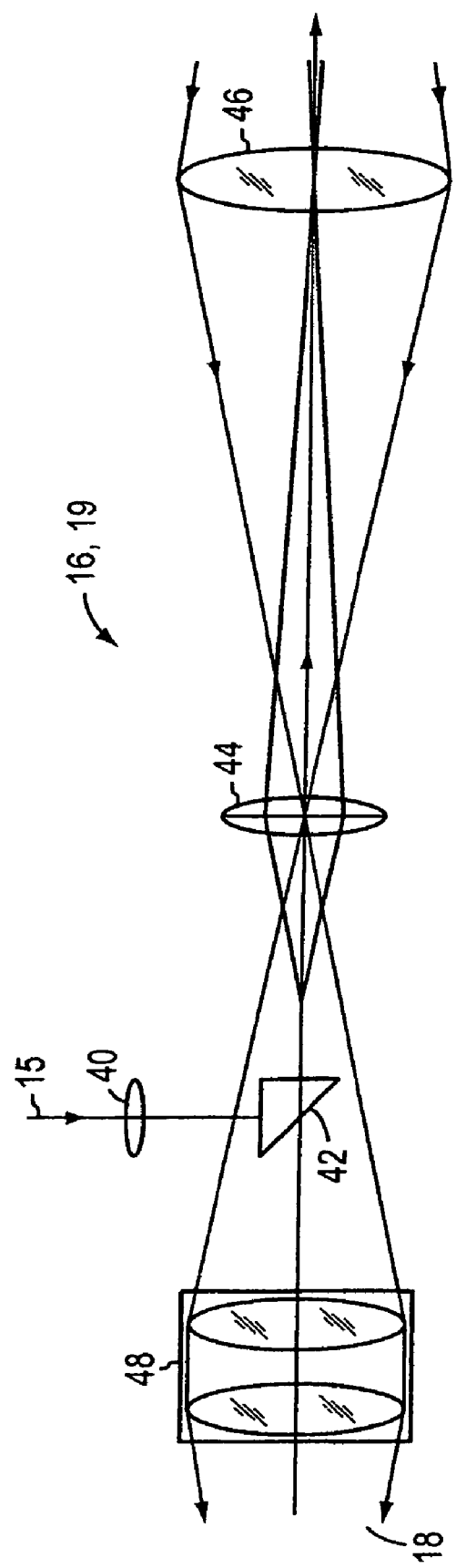
FIG. 1B illustrates schematically an optical delivery and collection system used in the system of FIG. 1.

FIG. 1B illustrates schematically an optical delivery and collection system (a combination of systems 16 and 19) used in the system of FIG. 1. This system is designed for direct imaging or for scanning the image over the detector. The optical delivery and collection system includes a large objective lens 46, a lens 44, and a detector lens system 48. Objective lens 46 forms an intermediate image of the examined tissue 8 and this is transferred to detector 17 by detector lens system 48. The irradiation laser beam 15 is focused by a lens 40 to a small prism 42 (or a mirror). The light scattered directly at the sample surface is blocked by prism 42.

The light collected from the examined tissue 8 by the large objective lens 46 forms an intermediate image in the plane of lens 44. Detector lens system 48 is constructed and arranged to transfer the first image into detector 17, which is preferably a multianode photomultiplier tube (PMT). Detector lens system 48 uses two or more lenses to obtain a higher aperture while maintaining an acceptable image quality.

Referring still to FIG. 1B, the scanning design includes a scan mirror assembly located between prism 42 and lens 44. As described above, objective lens 46 forms an intermediate image of the examined tissue, which is transferred to the detector by detector lens system 48. The input laser beam 15 is provided through lens 40 and prism 42 (or a mirror) and focused on lens 44. Lens 44 is the 'scan lens' that sends the laser at a variable angle through a stationary spot at the center of objective lens 46. A baffle in front of the detector may be used to block light scattered directly at the tissue surface. Photons detected by, for example, an 8×8 PMT detector are recorded into several separate channels and assigned to the different scan positions. This gives an n-dimensional data array for two detector coordinates, two source coordinates, and the time in the time-of-flight measurement. The system may include also a polarizer and may be adapted for detecting fluorescent light excited in the examined tissue.

Figure 2:
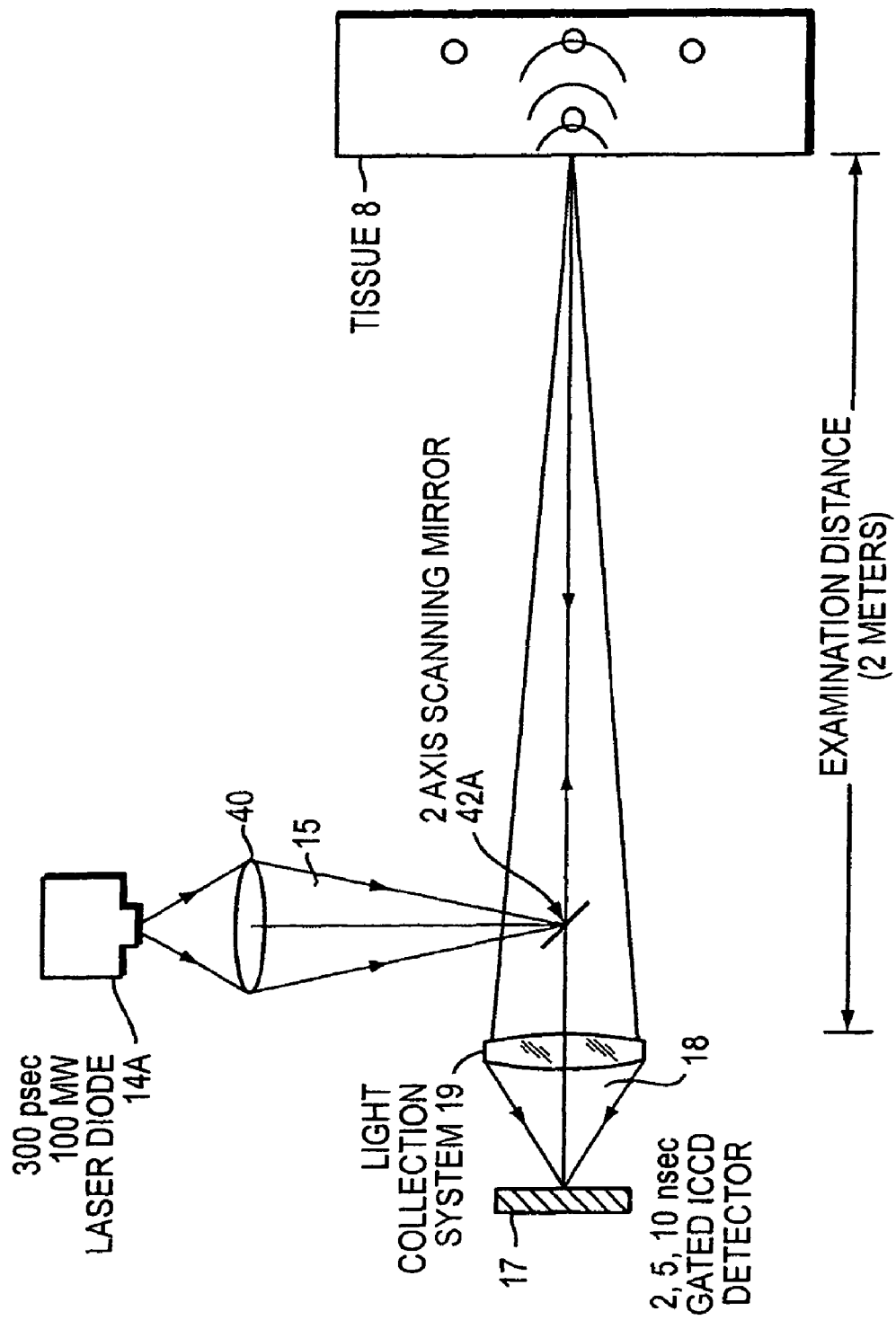
FIG. 2 shows schematically another embodiment of a non-contact optical examination system having a light source and a light detector remotely located from the examined biological tissue.

FIG. 2 shows schematically a non-contact optical system including optical delivery system 16 and light collection system 19. Optical delivery system 16 includes a scanning mirror 42A for scanning a light beam emitted from light source 14A over two dimensions. Specifically, mirror 42A guides the laser beam to tissue 8 by scanning in 2 axes in the flying spot manner. Light collection system 19 is arranged on axis with the scanned beam to receive returning light from tissue 8. Light collection system 19 provides the collected light to light detector 17. Light detector 17 is an ICCD that is gated at 2, 5 and 10 nanoseconds.

Importantly, the non-contact optical system irradiates biological tissue with photons of at least one selected wavelength and then detects photons that have migrated in the tissue and exited the tissue (i.e., emergent photons), but separates the "reflected" photons, i.e., photons that were reflected from the tissue surface and thus provide "no tissue property information" since these photons did not migrate within the tissue. This separation may be done using different techniques depending on the spectroscopic system. For example, the TRS system described below uses light pulses of about 2 nanoseconds to distinguish between the reflected photons that reach the detector first, and the photons that have migrated in the tissue prior to detection, which photons are delayed several nanoseconds. Other spectrophotometric systems separate the reflected photons from the emergent photons using optical barriers, various properties of light such as polarization, different wavelengths such as excitation and fluorescent wavelength, and other methods.

Figure 2A:
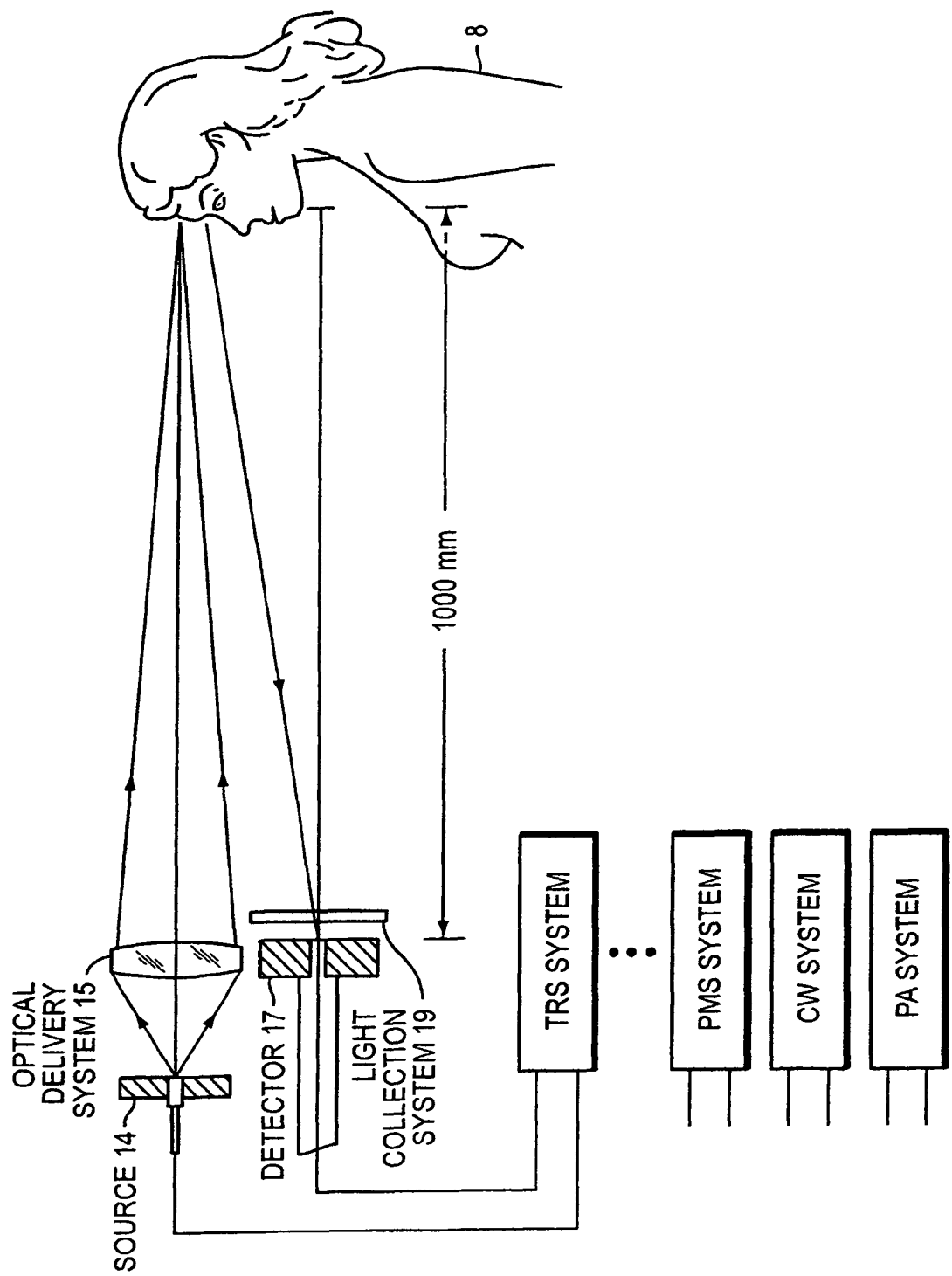
FIG. 2A shows schematically another embodiment of a non-contact optical examination system.

The spectrophotometer of FIG. 2A uses a similar scanning and light collection system. The non-contact optical probe may be collected to a TRS system, a PMS system, a CW system, or a phased array (PA) system. This system may be used for different applications, including medical applications, security applications or malevolence detection, as described below.

Referring to FIGS. 2A-I and 2A-II, the optical system can use different types of photodetectors, single channel or multiple channel. For example, Peltier cooled gallium arsenide PMTs have adequate sensitivity and speed for a 2 nsec gate and are sensitive to wavelength range 690-850 nm. For multiple channel detectors, PMT arrays, microchannel plate or ICCDs can be chosen. With multiple channels imaging data collecting can be done more rapidly, giving more adequate time resolution, appropriate spectral sensitivity, and a low cross talk. The multichannel detector is shown in FIG. 2A-II, wherein a "rosette" or circle of GaAs PMT detectors (23) in TO-8 size form a multichannel detector. The detector system has 8 independent PMT channels, directly exposed to back-scattered light without attenuation by an optical fiber. Each PMT has an individual cooler and sends a signal to a router which connects to the SPC module. Light source 14 focuses to the center of this circle or scans to each PMT position.

Figure 2B:
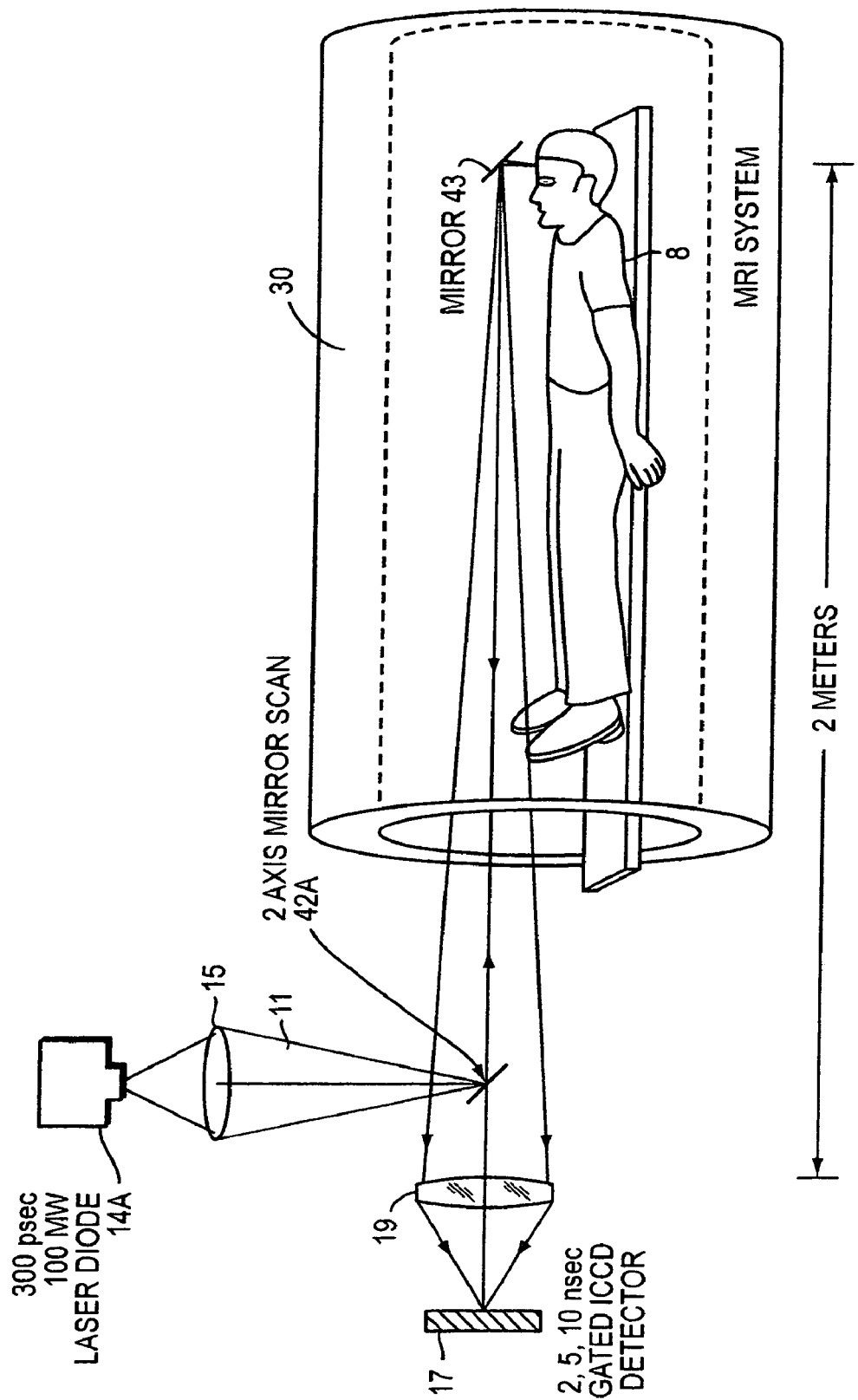
FIG. 2B shows schematically another embodiment of a non-contact optical examination system used for examination together with an MRI system.

Referring to FIG. 2B, a non-contact TRS system is designed for use with an MRI magnet used, for example, for MRI or fMRI examination. The TRS system includes light source 14A providing 300 picosec. light pulses and light detector 17, which is an ICCD. Coaxial mirror 42A sends the illumination beam 11 along the axis of lens system 19 and another mirror 43 (also used for observations of the subject) directs photons to and from the forehead of subject 8 as he is in the MRI imaging magnet 30. Mirrors 42A and 43 may be used to scan light over the forehead in the flying spot manner to obtain an image of the human forehead (or any other biological tissue). The nuclear magnetic resonance coil (NMR coil, not shown) is arranged in a squirrel cage manner so that optical access to the forebrain is possible. A computer collects the data and displays the data corresponding to the remitted photons from the brain as a logarithmic progression, or as a gated output of 2, 5 and 10 ns, as shown in FIG. 4C or 5A.

Figure 2C:
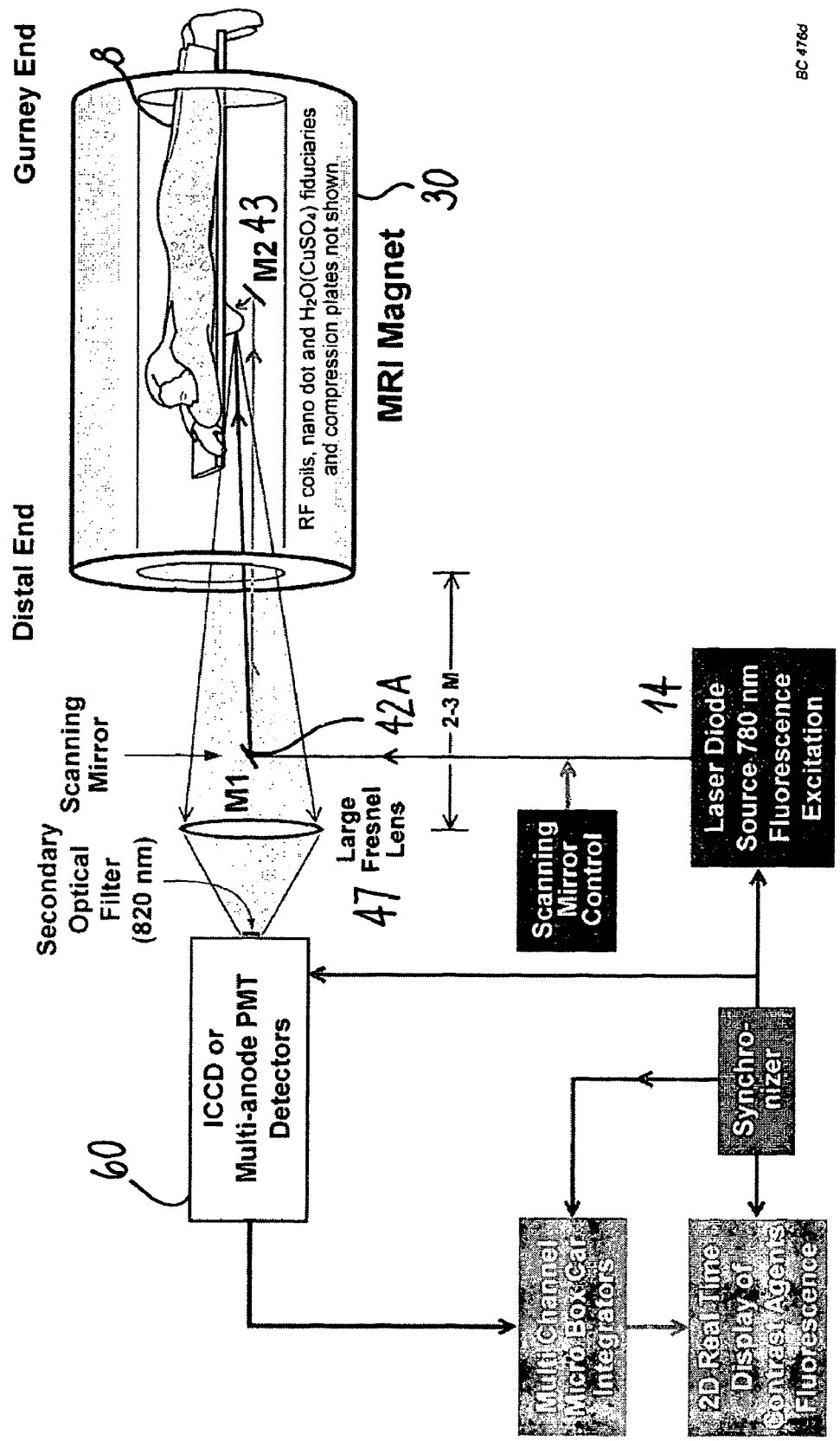
FIG. 2C shows a patient undergoing a non-contact breast examination inside the MRI magnet.

FIG. 2C shows a non-contact TRS system similar to that in FIG. 2B, where this time subject 8 is in MRI magnet 30 for breast examination. This system's light source 14 provides light pulses of 780 nm wavelength, and it has a multiplicity of light detectors 60, either ICCD or PMT. A coaxial mirror 42A also sends the illumination beam 11 along the axis of lens system 19 and another mirror 43 directs photons to and from, in this case, the breast of subject 8 as she is in MRI imaging magnet 30. Mirrors 42A and 43 may be scanned as explained previously with control 49.

Figure 2D:
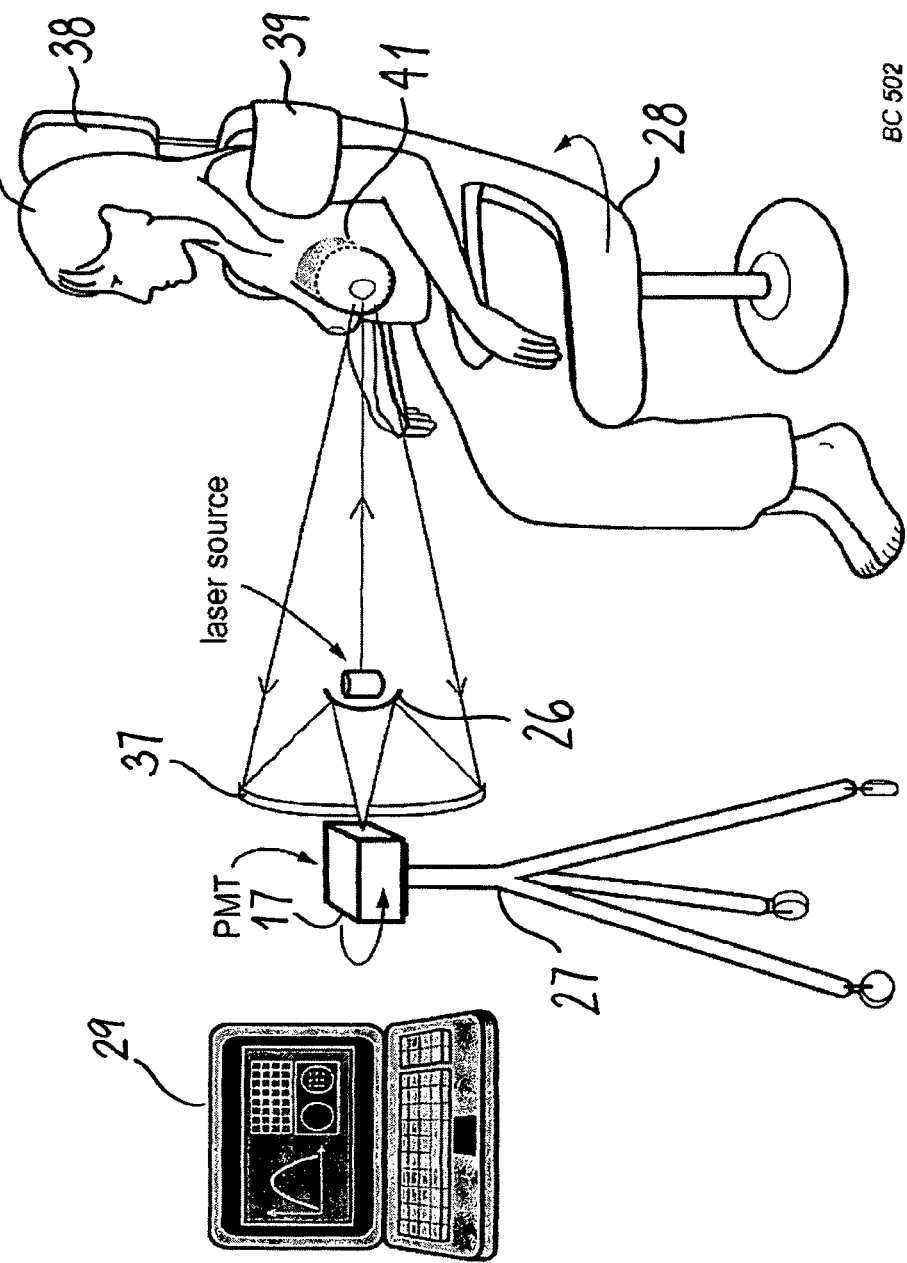
FIG. 2D shows schematically another embodiment of a non-contact optical examination system adapted for breast examination.

FIG. 2D illustrates remote sensing of the breast. Subject 8 is seated on rotatable stool 28, only 1-2 m away from the tripod-mounted reflective optics 27, including mounted parabolic mirror 26. Headrest 38 and shoulder clips 39 keep the patient stationary. The contours of the nipple and fiduciaries can also be obtained to monitor motion. Laser source 14 is directed towards a spot on the patient's breast where a suspicious mass is located. The photon migration signals from the surrounding area are gathered by parabolic reflector 37 and imaged onto multi-element detector 17, with acquisition times of a few seconds. The optic assembly can be scanned over the breast itself by mechanical movements. Furthermore, deliberate movements of the breast will present all views of it. The contralateral breast may be scanned and compared to the other. This system can especially detect the contingent region between chest and breast, 41. There is also access to the patient at the sentinal lymph nodes. Different perspectives, like a side view of the breast, are obtained by rotating the chair. Furthermore, the system moves or turns the optics or the detector for optimal data collection.

In addition, other scans are possible with this equipment: the Scout Scan quickly identifies a suspicious mass in a breast by starting a low resolution scan and covering a large area of just a few voxels, like 5×5 of 1 cm each. The resulting rough image can be presented in real time with the use of a simple data processing method: back projection, which analyzes the photon decay pattern data from each detector. If an anomalous signal occurs in one of the voxels and displays online on computer 29, (the anomaly being an incremental signal of angiogenesis, deoxygenation, water, or lipid) we identify this voxel as suspicious and start a Fine Scan. After identifying a suspicious mass, a high-resolution scan will start only in this region.

The Fine Scan is a raster scan with a high resolution, and with limits to a particular ROI. Sufficient volume of suspicious mass is included so that signal will increase for image analysis. A baseline scan of either model tissue or contralateral ROI is taken with longer integrating time, perhaps 5 sec. electronically switched into the gated integrator. Furthermore, the gated integrator is programmed to time resolve the photon decay kinetics for TRS. Then, flying spot iterating between the model and the true ROI is done, until a different signal appears clearly in terms of angiogenesis, hypermetabolism, or the presence of molecular beacons between the two tissues. The molecular beacon ICG does not work well for this purpose.

Then, as a search for additional anomalies, a scout scan across both breasts is performed. The system can record the time course of ICG introduction, absorption and release, providing the scout scan has localized a suspicious area which is to be studied by a fine resolution scan immediately following the IV delivery of 2/10 milligram per kilogram of ICG. Successive scans every 10 seconds will be recorded over as many voxels as is feasible and images of the ICG response will be created. At the same time, a time course of ICG response of the voxels of maximal signal-to-noise ratio will be computed and the kinetics fitted to a 2-4 compartment model to extract useful diagnostic information on this type of tumor.

While FIG. 2C suggests measuring the ICG kinetics in magnet 30 for fused imaging, the use of appropriate fiducials on the human breast during the intra-magnet Scout Scan enables correlation of optical data with the MRI.

Referring to FIG. 2D, for the breast, the advantages of the above scanning procedure is that both breasts can be checked at the same time, so normal tissue can be compared with tumor tissue and maximal contrast can be achieved. 'Rough' scanning can be done before 'fine' scanning to check a site quickly. The former helps find an abnormal region and the latter increases signal (recruit more volume) and resolution. Some regions can be closely checked to get more diagnostic information, like the chest-breast contingent and middle line between two breasts, where the contact optical imaging system using fibers cannot reach. Scanning of the lymph nodes on the chest and neck to check any metastasis of a tumor can be done, as well. This technology will be uniquely advantageous and efficient when the FDA approves molecular beacons for breast cancer. This procedure can even guide surgery for removal of tumor tissue.

Figure 2E:
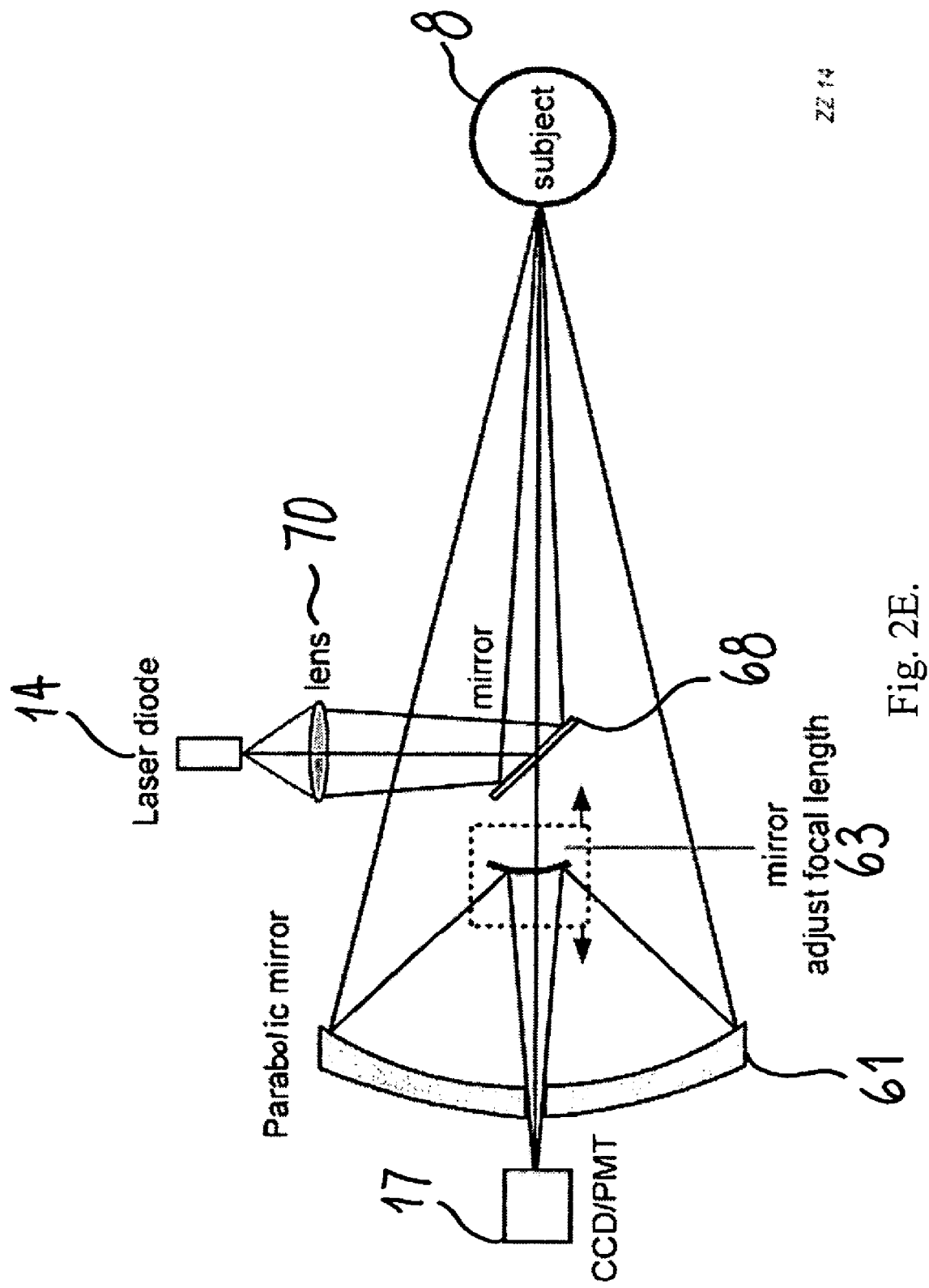
FIG. 2E shows a reflective optics system with integral scan for remote sensing.

FIG. 2E illustrates a Flying Spot Mirror Galvanometer System utilizing a 2-axis mirror galvanometer. The system may use a single PMT detector or multiple detectors. The geometry enables flying spot imaging of small animal brain, which works successfully even at low resolution. Higher resolution can readily be obtained by replacing the single PMT with an array of PMTs or an ICCD much in the way used in small animal imaging. Mechanical pointing of the entire optical system is made particularly convenient with parabolic mirror 63. These two methods of moving the laser can be used in combination, in fact: a flying spot scan is an essential feature of the device. As described later, there are two types of scans—a low resolution large area scan, and a high resolution smaller area scan. The low resolution, or Scout Scan, for locating an abnormal area, has a large step size and moves the whole system, including optics and detector. The high resolution smaller area, or Fine Scan, uses a small step size and a high resolution image, where flying spot technology is preferred.

If laser beam 14 is fixed, illumination can be of two types. The first type provides on-axis illumination. Fixed mirror 68 is used for aiming a laser at the focal point of the optical system. The second type provides all illumination approximately 45 degrees with respect to the optic axis of the lens system. If laser beam 14 is moveable, light can be delivered to different positions very rapidly as the fine structure of the ROI is examined, or the ROI is changed to a different position. This method is good for a multiple detector array (See FIG. 2A-II) or an ICCD. The advantage of this technique is the speed of the laser scanning. In a short time, a great number of source and detector positions can be analyzed, which will give a large amount of data and increase image accuracy.

The Flying Spot Mirror Galvanometer System of FIG. 2E is the 2-axis mirror galvanometer drive we developed for flying spot applications with a single PMT detector. It is the geometry used successfully in the past to construct a flying spot imager for small animal brain, which worked successfully at low resolution. Higher resolution can readily be obtained by replacing the single PMT with an array of PMTs or an ICCD much in the way used in small animal imaging. Mechanical pointing of the entire optical system is made particularly convenient with parabolic mirror 63. These two methods of moving the laser can be used in combination, in fact: a flying spot scan is an essential feature of the device. As described later, there are two types of scans—a low resolution scan large area scan, and a high resolution smaller area scan. The low resolution, or Scout Scan, for locating an abnormal area, has a large step size and moves the whole system, including optics and detector. The high resolution smaller area, or Fine Scan, uses a small step size and a high resolution image, where flying spot technology is preferred.

Figure 2F:
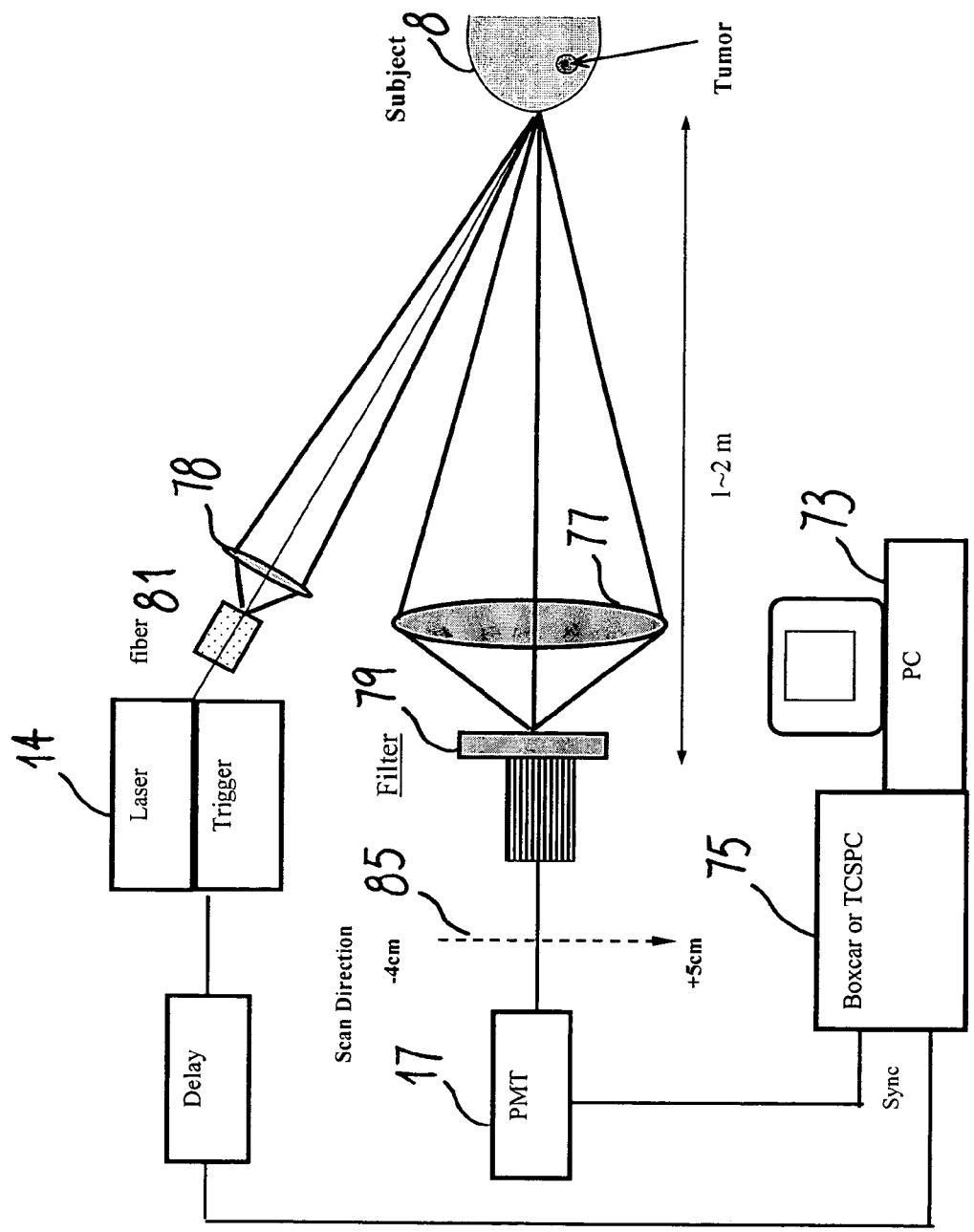
FIG. 2F shows the refractive optics system for remote sensing.

FIG. 2F illustrates a simple version of the use of refracting lenses in a TRS system for studying breast cancer imaging. This system has a major advantage in that alterations in the configuration can readily be made. We have compared one lens with three lenses and found that, as expected, the multiple lens system was much more flexible and performed as well. Between the 3 lenses, 2 aperture stops are used to block specular reflection. Detector 17 can be moved laterally and is located usually 1~2 cm off-axis (85) to minimize the photon counts of specular reflection. Laser source 14 is 1-2 m away and detector 17 is 2.5 m away from subject 8. Laser beam 14 is fixed in this case, so to provide movement of the illumination towards subject 8 in this case, fiber 81 or lens 83 can be moved. This system has a pulsed laser diode (FWHM=300 ps), mainly using wavelengths 690 and 780 nm; detector 17; time-correlated single photon counting system (TCSPC) 75 which has TAC; and a computer display of count rate 73. The optical system is X-Y scanned and the magnification is varied.

Specular reflections have a much higher intensity than multiple-scattered light, to vary the depth dissemination. The time-resolved system has the advantage of being able to discriminate between the two by their different photon arriving times. In addition, the source light is at a 45 degree angle: detector 17 is off axis 85 so there is a 2 or 3 cm deflection between the illuminated spot and the detecting spot. We may use 1 or 2 aperture stops to block the specular reflection as shown in FIG. 2E.

Figure 3:
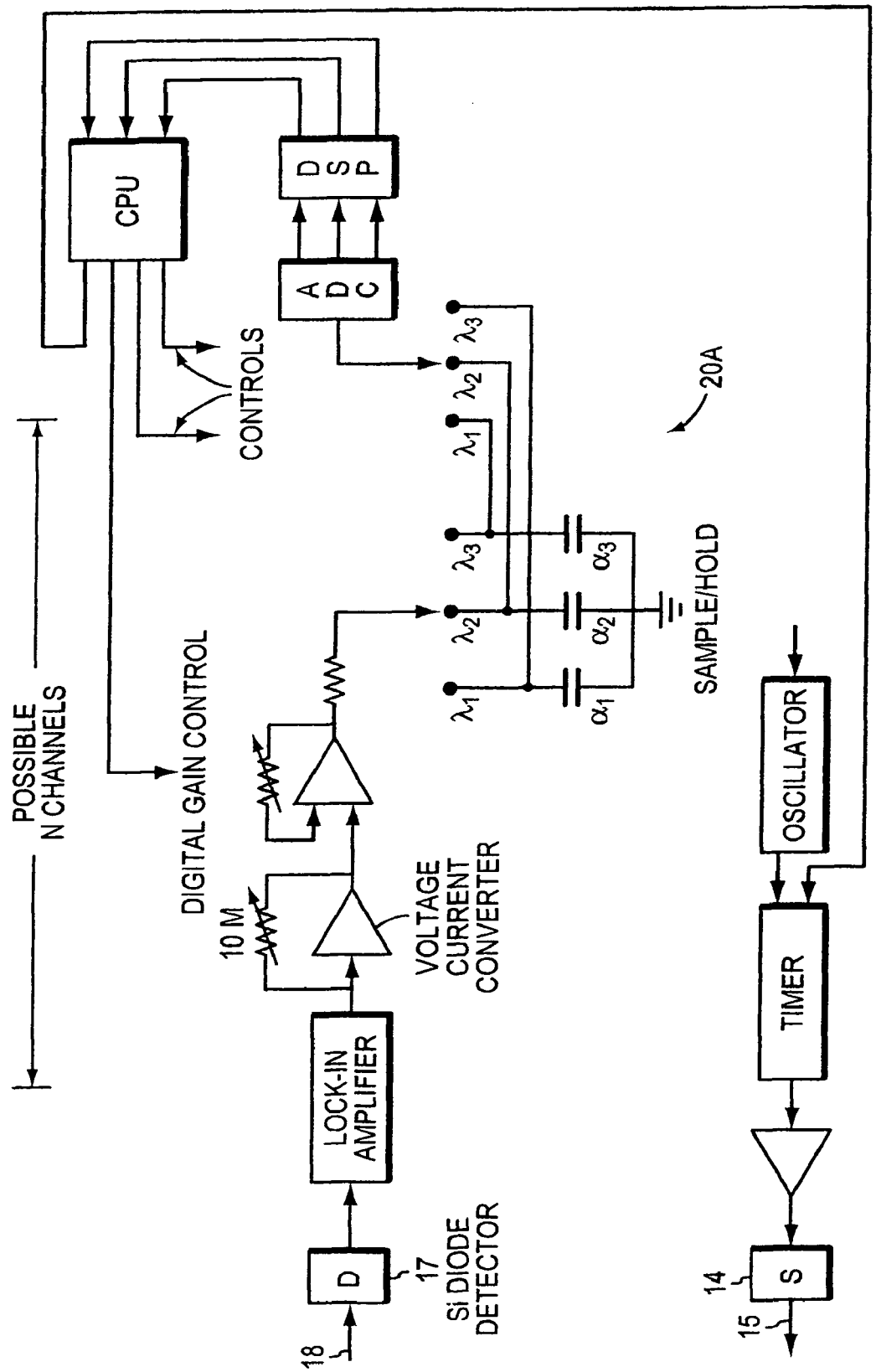
FIGS. 3 and 3A show schematically a CWS system used for non-contact optical examination or imaging.
Figure 3A:
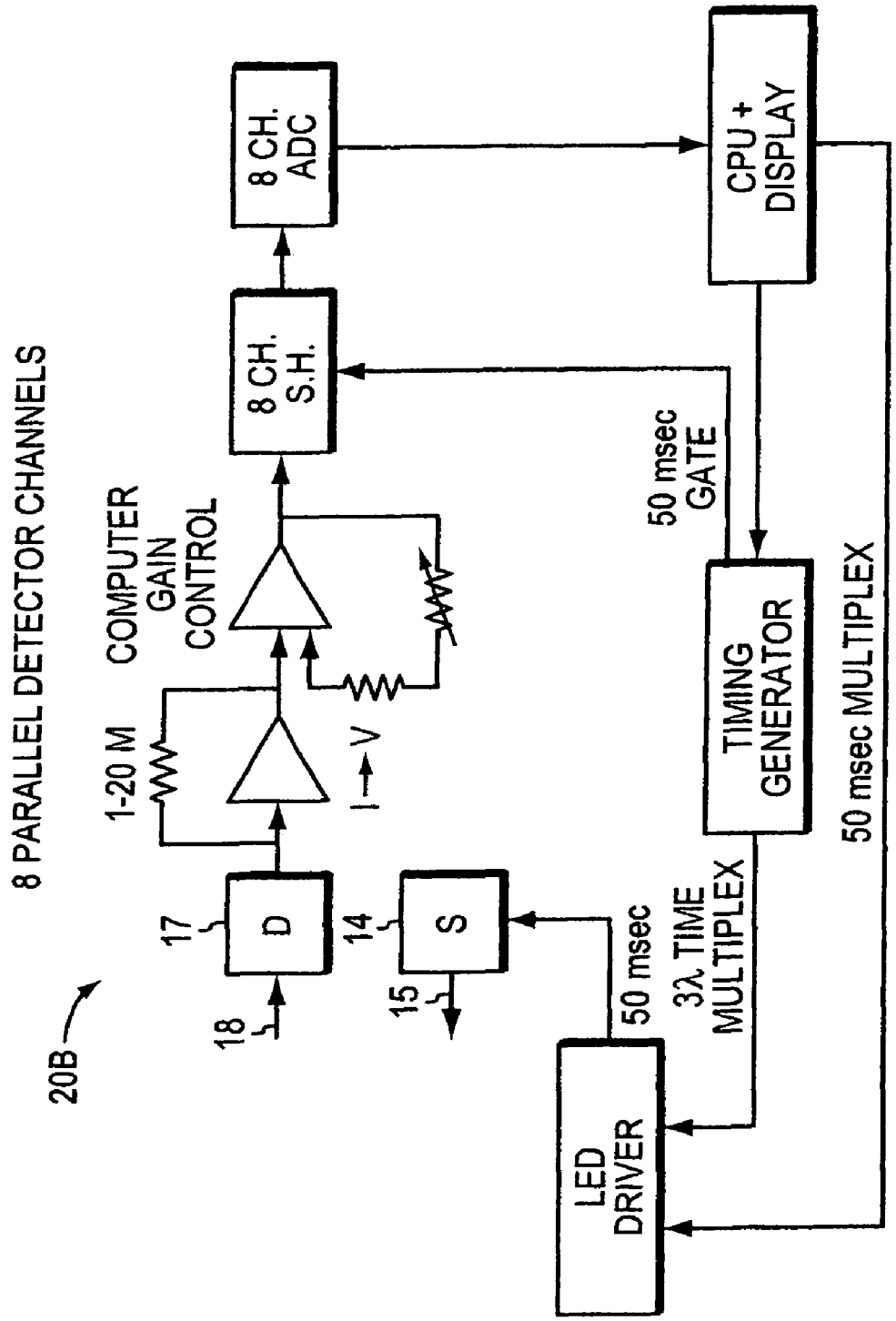

FIGS. 3 and 3A show schematically electronics 20A and 20B of a CWS system used for non-contact optical examination or imaging. FIG. 3 shows schematically a three-wavelength optical module designed for examination and imaging of cognitive functions. The system includes a gain control for calibrating the optical signal in μM, prior to brain examination, as described below. The optical data are provided to a computer in a digital format. FIG. 3A shows schematically another embodiment of a three-wavelength, non-contact optical module. The electronics of 20B uses eight parallel channels for receiving optical data. This imager uses a probe having 8-channels; the input to each channel is obtained from one of the eight silicon diode detectors located around a single 3-wavelength LED source. It uses the frequencies in the ISM band to transfer the data from the probe to the remote receiver, where the data acquisition and analysis are done. The synchronization between the transmitter and the receiver is achieved using the Sync pulses, produced by the timing circuitry at the probe and transmitted every cycle.

In the system of FIG. 3A, everything is localized with a mercury battery timer and driver for the two or 3 wavelength LED a mercury battery operated silicon diode Complementary Metal Oxide Semiconductor (CMOS) detector and a radio transmitter using an RF frequency encoded system so that all 8 detectors are at a different transmitter frequency. Time multiplex is less complicated, i.e., the only timer here is the light source that gives the 2 or 3 wavelengths and then a dark interval, which is used as a synchronizer. This gives the ultimate flexibility and a good measure of non-transmission from source to detector because each detector is recessed with the rubber rim around the edge of the light source.

For example, in order to exactly equalize the outputs from several integrated chip silicon diode detectors, there may be a fifty-dB digitally controlled gain stage. The output in the region of 1-5 V pulses at 5 ms time multiplex pulses are connected to a sample-and-hold circuit in order to obtain an averaged "peak value" over 100 ms. Here, simple reed switches are adequate to give closure during the peak value of the input signals at the three wavelengths as are provided by the computer clock-controlled time-sequenced switches. Instead of taking the output at the time of closure of the input switches, the averaged value is sampled by the ADC program at an interval when the charge on the capacitors has stabilized and an average value of over the preceding twenty (20) closures of the switch is obtained. Thus, ADC sampling can take place at any time except when the signal switches are activated to impart new information to the holding circuit. An 8-bit ADC is quite adequate and Digital Signal Processing (DSP) thereafter is optimal in view of the excellent averaging properties of the sample-and-hold circuit. The back projection algorithm for imaging provides information for each one of the 16 sectors.

Figure 4:
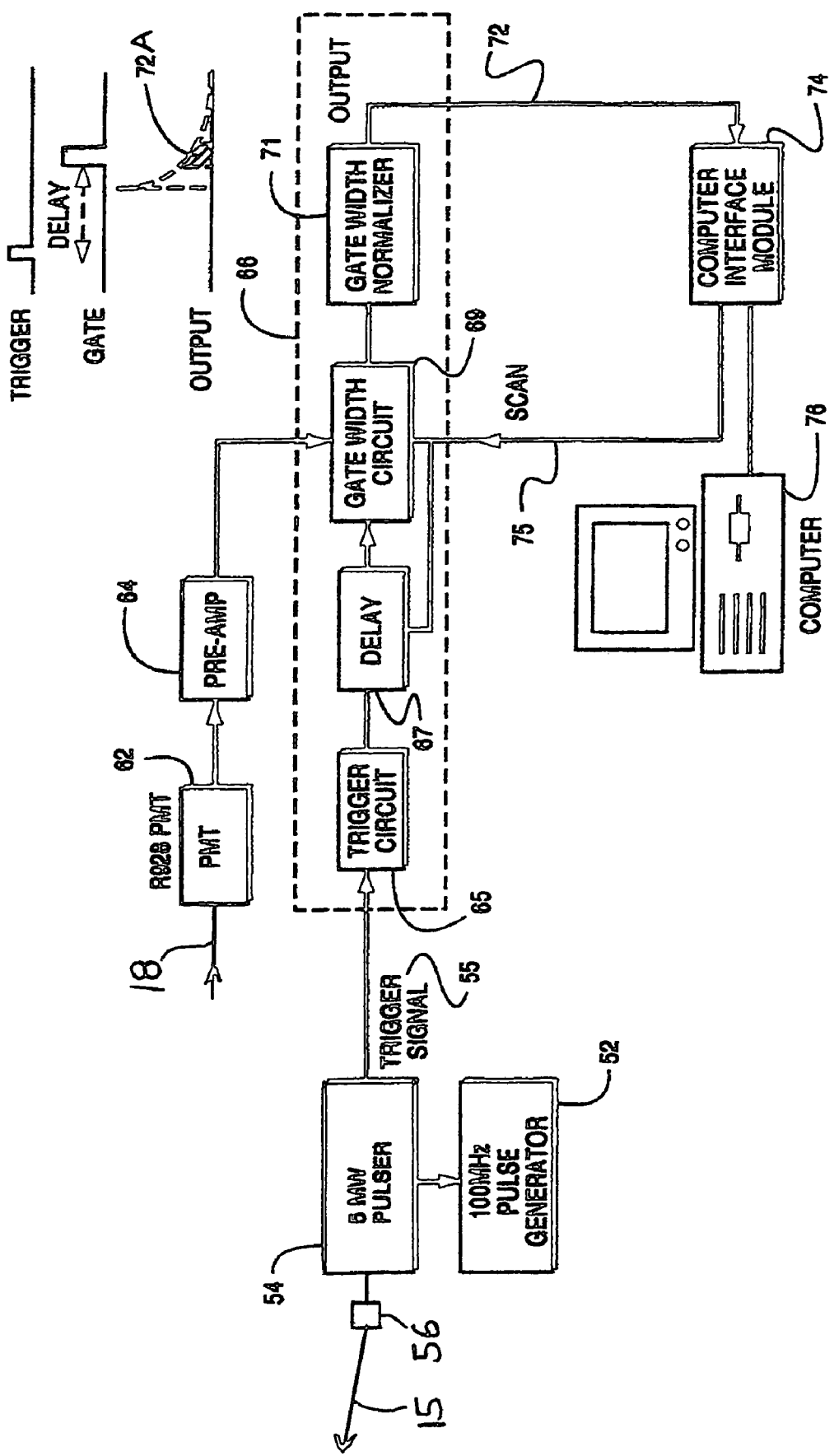

FIG. 4 shows diagrammatically the TRS system using a single "boxcar" integrator for the gated photon signal integration. A pulse generator 52 operating at a frequency on the order of 100 MHz connected to a pulser 54 drives a laser 56 (e.g., Hamamatsu PLP-10 pulsed laser diode). Laser 56 generates a train of light pulses of a known wavelength (e.g., 754 nm) and constant duration on the order of 100 psec. (Pulses of the order of a nanosecond can also be used.) The light pulses are emitted as light beam 15 and are delivered to biological tissue 8. The introduced photons migrate in the examined biological tissue and, during the migration process, the input pulse is modified by the scattering and absorptive properties of the tissue. Both reflected photons and photons migrating inside the tissue are provided to detector 62 (for example, Hamamatsu photomultipliers R928, R1517, MCP R1712, R1892 or ICCD commercially available from Jobin Yvon Inc., Edison, N.J. 08820) by light collection system 19 (FIG. 1).

Depending on which detector is used, the output of detector 62 may be amplified in a wide band preamplifier/impedance changer 64 and coupled to a boxcar integrator 66. Activated by a pulse gate, integrator 66 collects all arriving photons over a predetermined time interval. The integrator output (72) is sent to computer interface module 74. Computer 76 stores the total number of counts detected during the collection interval of integrator 66. FIG. 4 also shows a graph 72A of the detected counts corresponding to the delayed gate (illustrated in greater detail in FIG. 4C).

Integrator 66 includes a trigger 65 that is triggered by a signal 55 from pulser 54. Trigger 65 activates a delay gate 67 that, in turn, starts the counting of all detected photons during the time interval specified by a gate width circuit 69. Output from a gate width normalizer 71 is an analog signal or a digital signal representing all photons that arrived at the detection port during the preselected gate width interval. A suitable integrator can be achieved by using SR 250 manufactured by Stanford Research Systems.

Depending on the application, computer 76 sets the delay time of delay gate 67 and the gate width time of gate width circuit 69. The system can scan integration gate widths over the whole time profile of the detected pulse. Gate width normalizer 71 adjusts the width of the integration time depending on the detected signal level. The gate width may be increased logarithmically for smaller signals in accordance with the exponential decay of the fall of the detected pulse; this increases the signal-to-noise ratio. The system operates at a repetition rate of at least 10 KHz.

Figure 4A:
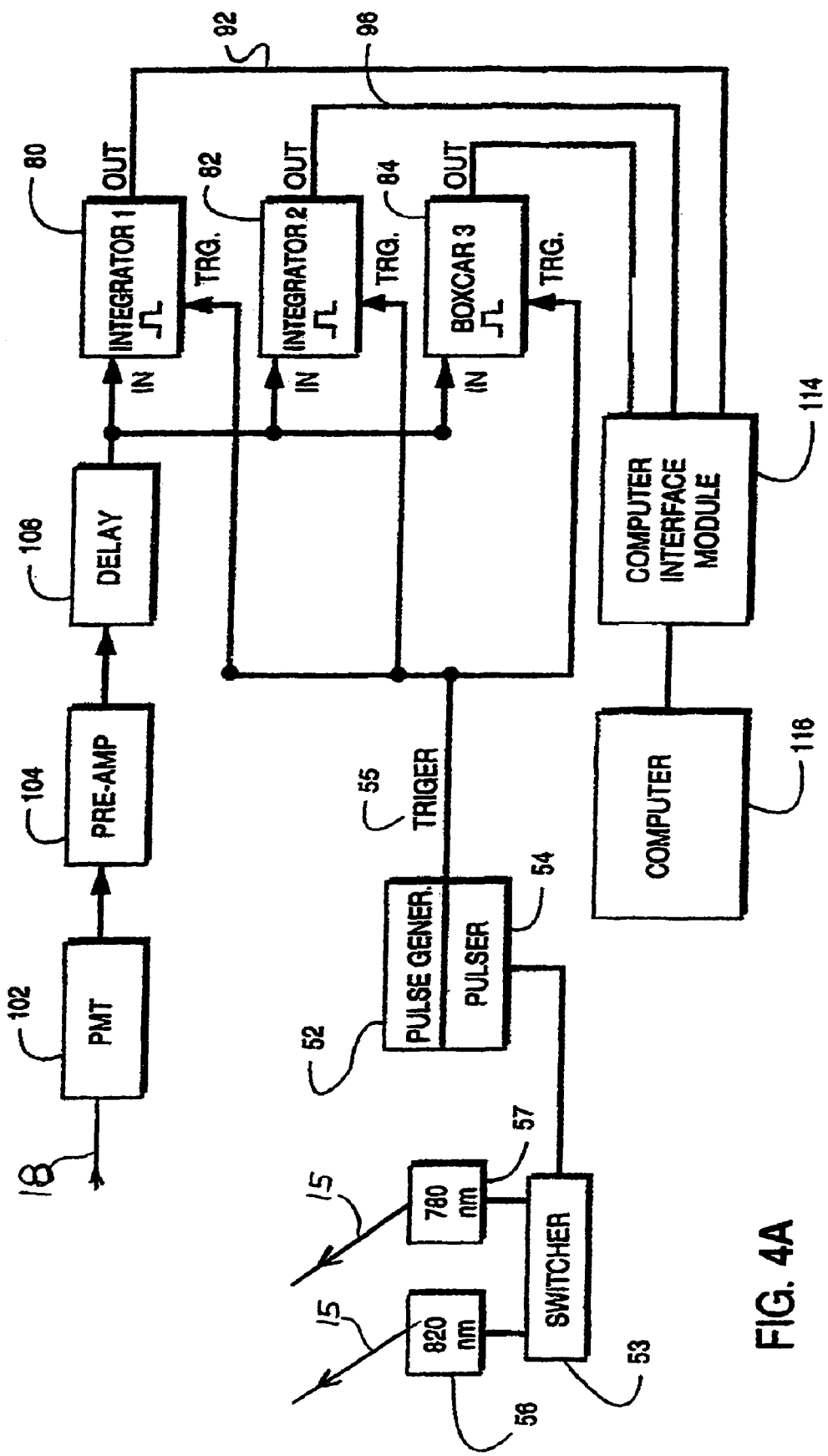

Referring to FIG. 4A, alternatively, the TRS system uses multiple, parallel integrators arranged in a faster and more efficient system. This system, just as the system of FIG. 4, may be used to determine the whole profile of the detected pulse shown in FIG. 4C by appropriately selecting the delay gates and the gate widths shown in FIG. 4B. Pulse generator 52 connected to a pulser 54 drives alternately lasers 56 and 57. The alternate coupling is provided by a switcher 53 that operates at frequencies on the order of $10^7$ Hz. Pulses of light of wavelengths in the visible or infrared range and duration in the range of about several nanoseconds to picoseconds are generated. These light pulses are alternately coupled to subject 8. The light pulses are modified by subject 8's tissue and are detected by detector 102.

The detected signal is amplified by preamplifier 104. Integrators 80, 82, and 84 collect data during selected gate width intervals, as shown on the timing diagram of FIG. 4B. Trigger 55 correlated with the input pulse 55A, triggers delay gates 1, 2, and 3 (shown in FIG. 4B) that are set to have selected delay times. Each delay gate then triggers its corresponding integrator that collects all photons arriving at the detector during the delay width time. Each integrator collects photons arriving at the detection port during its integration time defined by the gate width. This configuration can achieve a repetition rate of at least 10 kHz. The TRS system can separate the detected "useful" photons (which have migrated in the examined tissue) from the specular or surface-scattered photons that arrive much earlier since they are not delayed by the photon migration in the examined tissue.

Figure 4B:
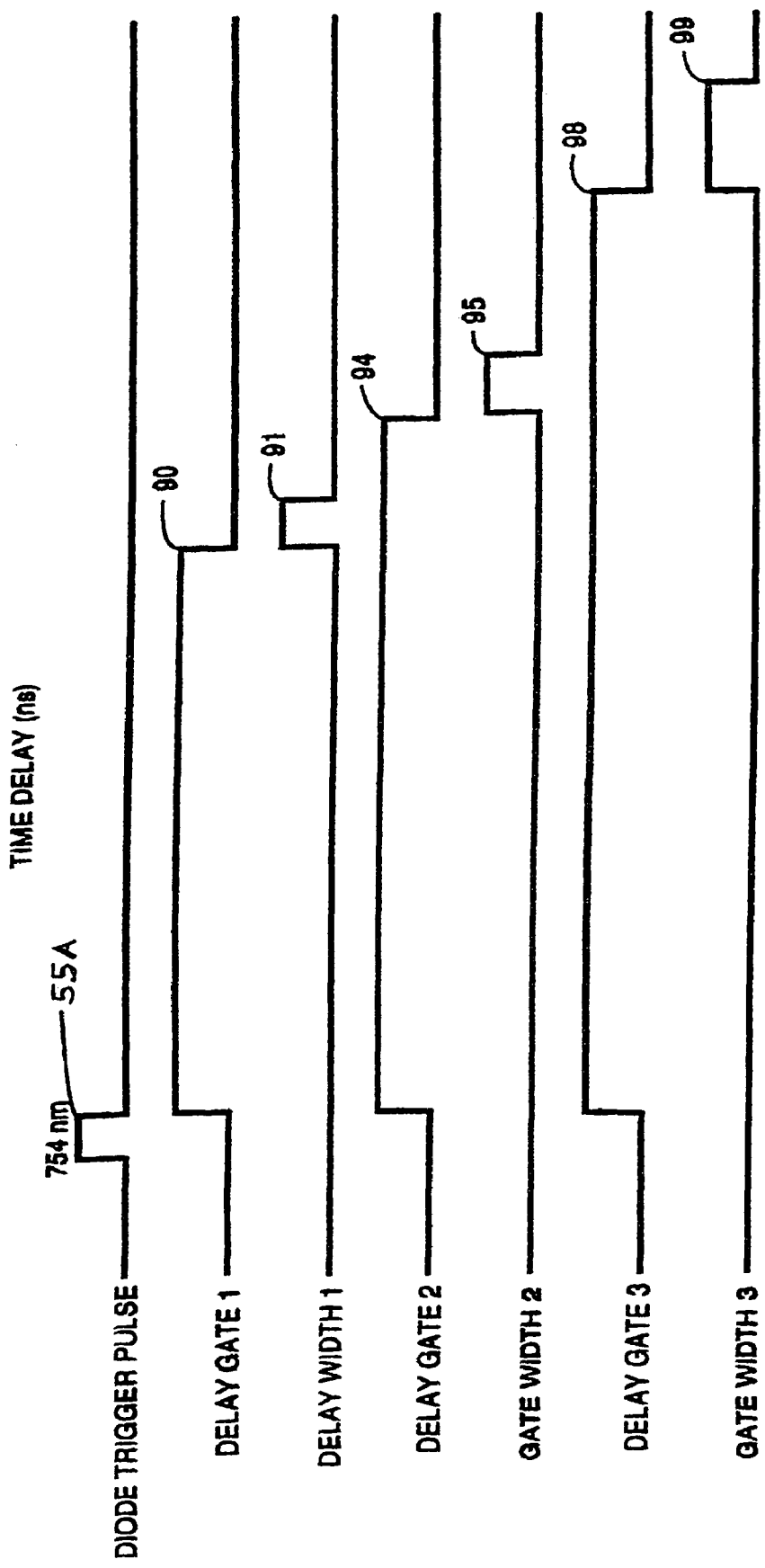
Figure 4C:
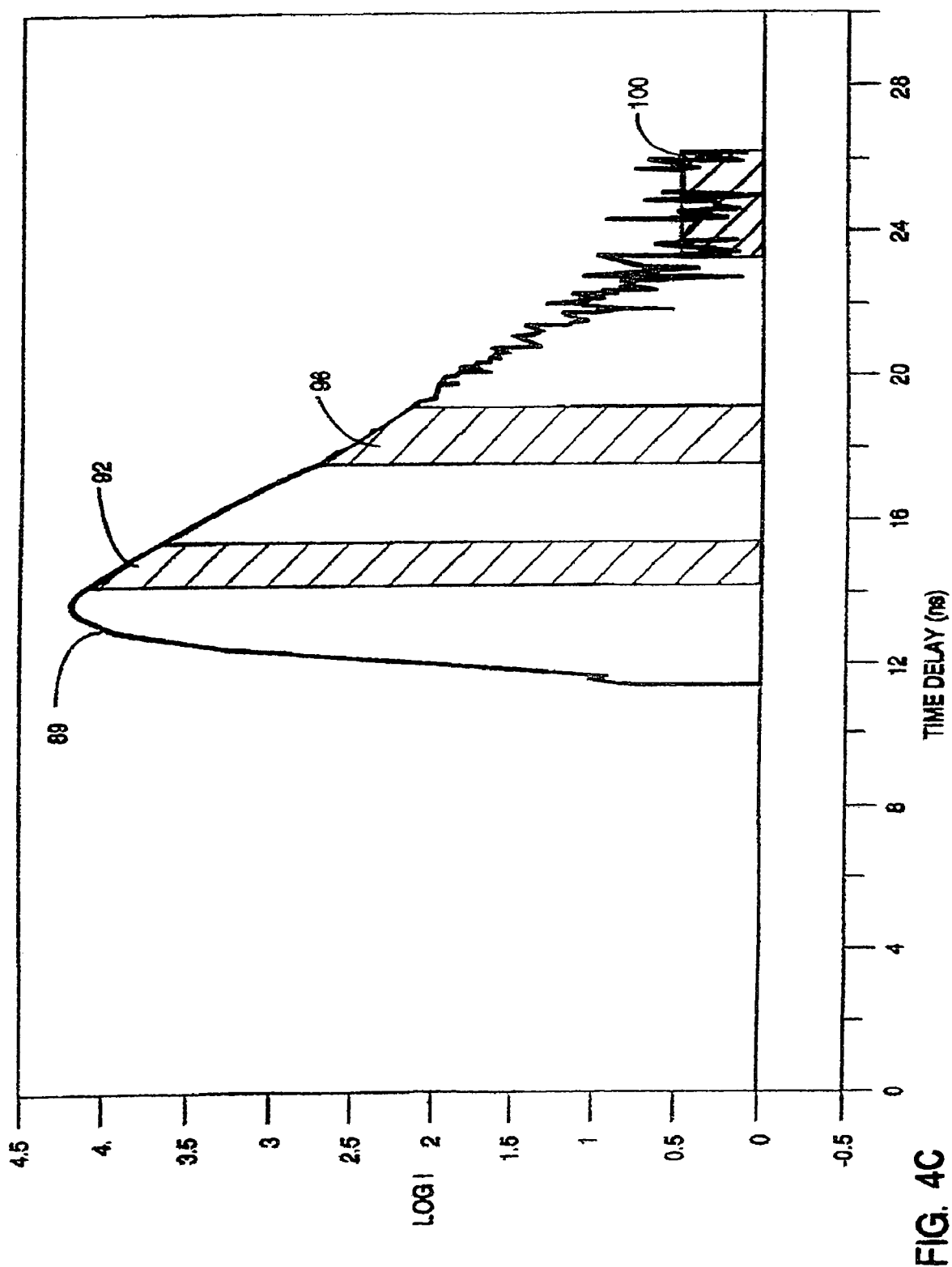

Referring to FIG. 4B, the TRS system uses the gate arrangement including gates 91 and 95 timed to detect the decay slope of the signal shown in FIG. 4C, while the third gate 99 may be used to determine the background signal shown as region 100 in FIG. 4C. Outputs 92 and 96 of integrators 80 and 82 are used to calculate the slope. To obtain approximately equal signal-to-noise ratios in the individual integrators, the length of the time windows is tailored to an exponential decay of the signal intensity with a logarithmic increase in the gate width with delay time.

Referring to FIGS. 4B and 4C, by scanning the delay gates (90, 94, and 98) and appropriately adjusting the gate widths, the system collects data corresponding to the entire detected pulse; subsequently, the shape (89) of the detected pulse is then calculated, i.e., time dependent light intensity profile I(t) is determined. The detected pulse shape, I(t), possesses information about the scattering and absorption properties of the examined tissue, which are closely related to the distribution of photon pathlengths in the tissue. The optical field is a function of the input-output port separation ($\rho$) as well as the optical properties of the tissue (absorption coefficient, $\mu_a$, scattering coefficient, $\mu_s$, and the mean cosine of anisotropic scattering, g). The general diffusion equation is used to describe the photon migration in tissue, as described by E. M. Sevick, B. Chance, J. Leigh, S. Nioka, and M. Maris in *Analytical Biochemistry* 195, 330 (1991) which is incorporated by reference as if fully set forth herein.

The system utilizes a previously determined solution for the fluency distribution in an infinite media as a Green's function with near infinite boundary conditions, wherein the diffusion equation is solved for the intensity of detected light in the reflectance geometry, R($\rho$,t), or the transmittance geometry T($\rho$,d,t). In the reflectance arrangement in a semi-infinite media with the separation of the input and output ports on the order of centimeters the reflectance was determined using equations provided in the above publication.

The TRS system enables direct measurement of the absorption coefficient or the effective scattering coefficient (1-g). $\mu_s$, using the equations described in the above-publication or as described in detail in U.S. Pat. No. 5,386,827, which is incorporated by reference. As described in U.S. Pat. No. 5,386,827, the systems of FIG. 4, 4A, or 5 enable direct, real-time output of the absorption coefficient $\mu_a$, tissue saturation (Y), average optical pathlength (<L>), and the scattering coefficient $\mu_s$. The absorption coefficient is quantified by evaluating the decaying slope of the detected pulse, as shown in FIG. 6.

As stated above, the intensity profile of the detected pulse, I(t), is strongly dependent on the absorption and scattering properties of the examined tissue. For a relatively homogeneous tissue (e.g., breast tissue), the detected pulse, in general, exhibits a single exponential decay. In cases wherein the light pulse migrates through different types of tissues (e.g., brain tissue, which includes white matter and gray matter), the detected profile I(t) includes "two or more superimposed pulses", each characteristic of one type of tissue. The TRS system of FIG. 4 can scan the delay gates over the entire arrival time delay of the migrating photons to collect and deconvolute the intensity profile, I(t). A computer processor then fits iteratively the intensity profile to two or more overlapping curves and determines the scattering and absorption coefficients for each tissue effectively using Equations (3) and (5) provided in U.S. Pat. No. 5,386,827.

In the TRS system that includes two wavelengths sensitive to hemoglobin (Hb) and oxyhemoglobin (HbO$_2$) (e.g., 754 nm and 816 nm), the hemoglobin saturation (Y) is calculated by taking the ratio of absorption coefficients and using the equation 8 provided in U.S. Pat. No. 5,386,827 for the oxygen saturation.

In the studies of the brain, the TRS-pulse system is used to obtain the scattering ($\mu_a$) and absorption ($\mu_s$) coefficients of the white and gray matter at each wavelength. The absorption factors are used to determine oxygen saturation which is then used to detect hypoxia, localized bleeding and other reversible or irreversible disorders. The scattering changes in the examined tissue could be a manifestation of periventricular signal hyperintensity (PVH), Alzheimer's disease manifested as plaques and tangles embedded in the gray matter, and others.

As implied in the earlier description, it is desirable to precisely determine the delay time of the detected pulse. In the systems of FIGS. 4 and 4A, the pulser sends a trigger signal directly to each boxcar integrator.

Figure 5:
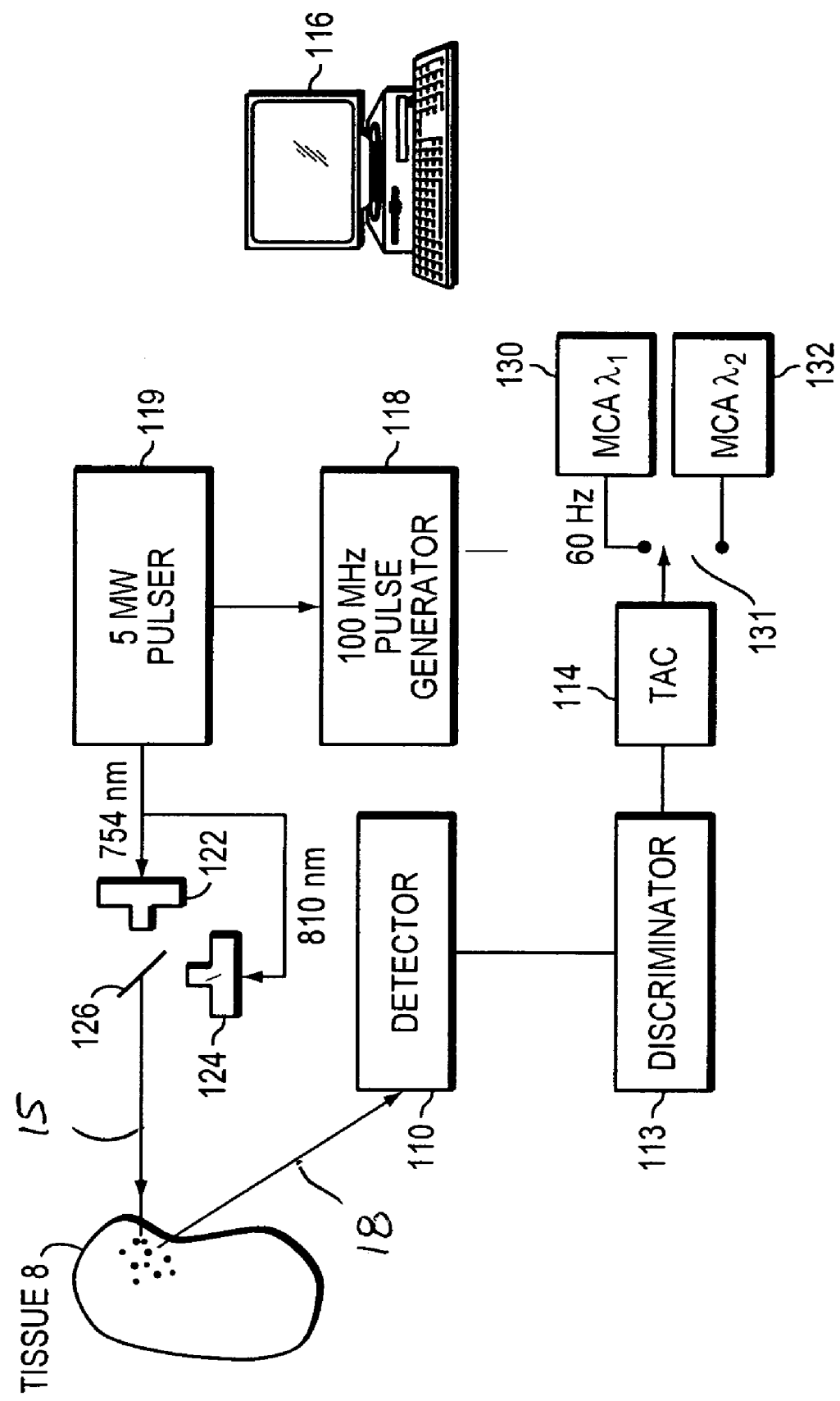
FIG. 5 is a schematic block diagram of another embodiment of a TRS system utilizing single photon counting electronics.
Figure 5A:
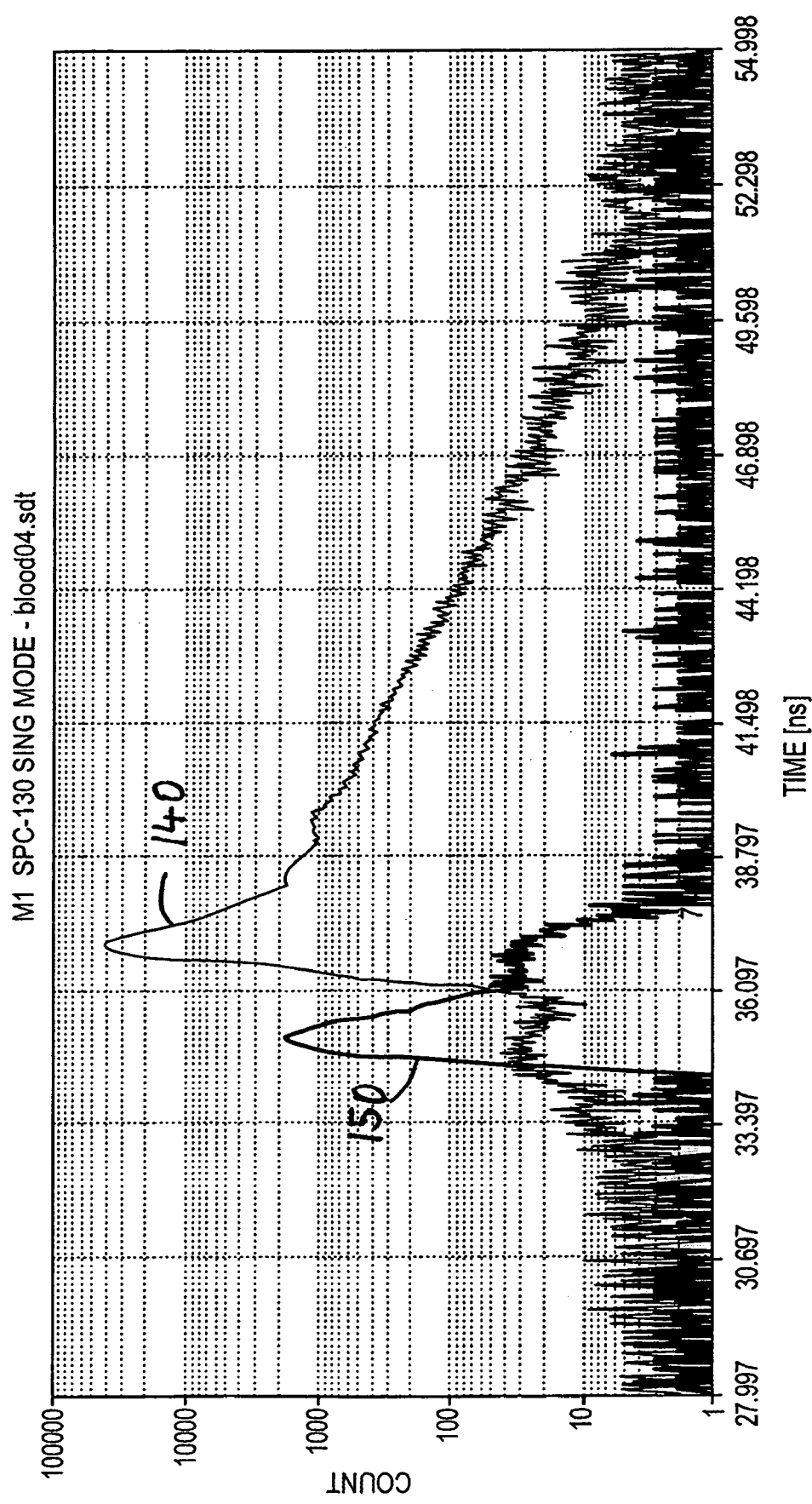
FIG. 5A is a time resolved spectrum measured by the TRS system of FIG. 5, which spectrum includes a modified pulse and a reference pulse.
Figure 6:
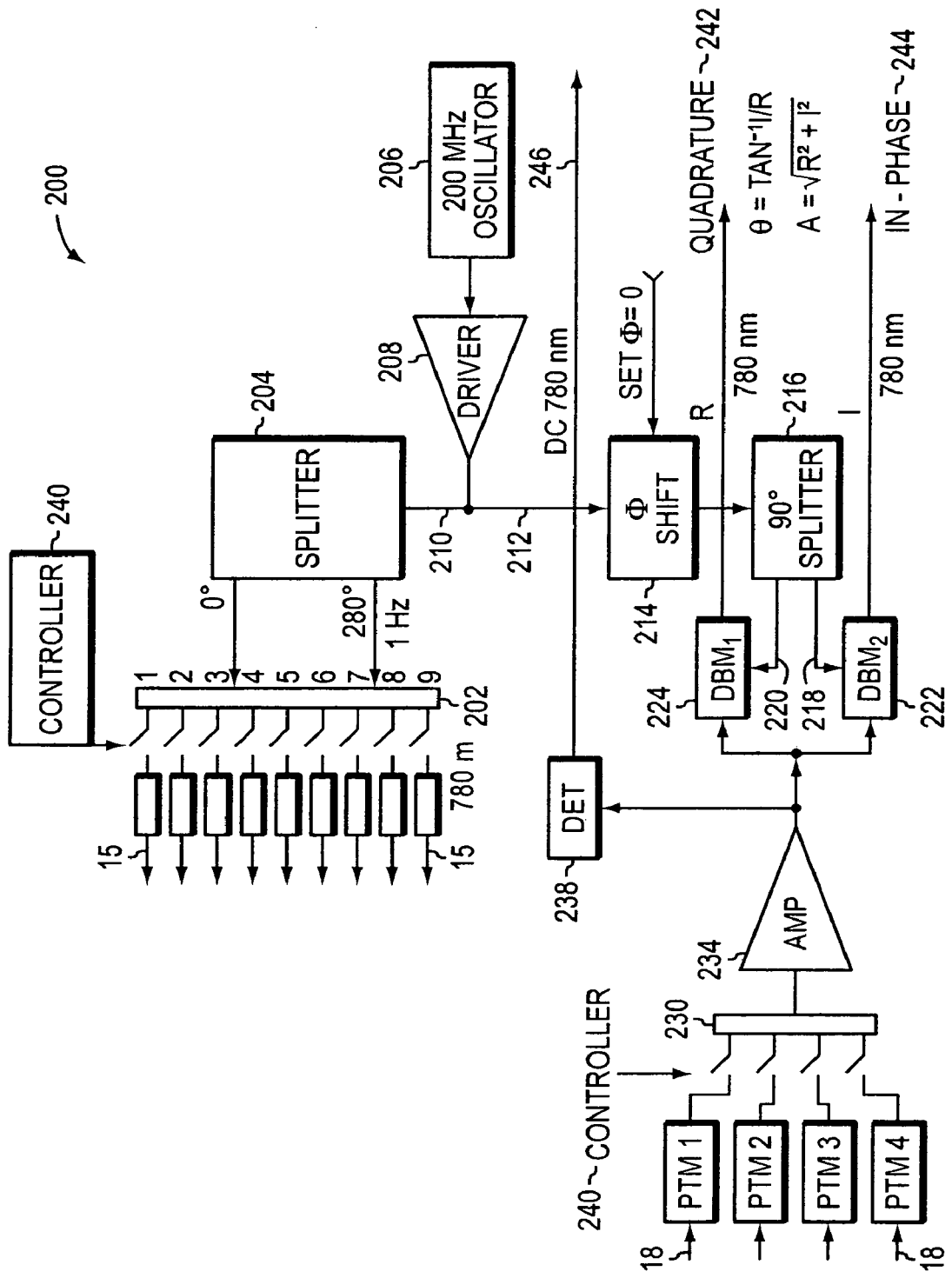
FIG. 6 shows schematically a homodyne phase-modulation system used for non-contact optical examination or imaging.

FIG. 5 shows a block diagram of the dual wavelength TRS system using single photon counting electronics. Laser diodes 122 and 124 (e.g., Hamamatsu PLP 10 laser diode) are driven by a 100 MHz pulse generator 118 connected to a 5 mW pulser 119. The light beam from laser 122 or laser 124 may be directed toward the tissue region of interest, or may be time shared electromechanically as shown in FIG. 5. Specifically, a vibrating mirror 126 (e.g., operating at 60 Hz synchronously with a switch 131) is used to deliver alternately the laser beam to the tissue region of interest (i.e., human tissue, small animal tissue, tissue model).

Referring still to FIG. 5, after the illumination of the tissue region of interest, photons migrate over scatter paths inside the examined tissue and exit the tissue surface. A photodetector 110 (e.g., a photomultiplier) collects at least a portion of the exiting photons. The output of photomultiplier tube 110 is directly connected to a wide band amplifier 112 with appropriate roll-off to give good pulse shape and optimal signal-to-noise ratio. A high/low level discriminator 113 receives an output signal from amplifier 112. Discriminator 113 is a pulse amplitude discriminator wherein the threshold for acceptance of a pulse is a constant fraction of the peak amplitude of the pulse. Next, the discriminator pulses are sent to a time-to-amplitude converter (TAC) 114.

The time-to-amplitude converter produces an output pulse with an amplitude proportional to the time difference between start and stop pulses. The pulse-photon detection cycle is repeated at a frequency on the order of 10 MHz to acquire a typical photon distribution. The multichannel analyzer collects only a single photon for each input light pulse. Signal from each detected photon is encoded for time delay and recorded. Following the time-to-amplitude conversion, the counts corresponding to the two wavelengths are separately summed in two multichannel analyzers (MCA) 130 and 132, respectively. Each multichannel analyzer collects and stores the time resolved spectrum that consists of a detected pulse (140, FIG. 5A) modified by the examined tissue and a reference pulse (150, FIG. 5A) collected for timing and reference purposes. The delay of the reference pulse in FIG. 5A is much smaller and is shown for pulse shape comparison only. (The system may use a reference fiber of a known length, coupling the light source and detector for detecting and collecting a reference pulse spectrum, used for calibration.)

In general, the TRS systems of FIGS. 4, 4A, and 5 provide nanosecond or picosecond laser illumination of a tissue region that is distant from the light source by 1, 2 or more meters permitting non-contact activation of photon migration. The detector system images the object illuminated using a large 10×10 cm lens which gives a viewing angle of approximately 10 degrees. In order to distinguish reflected light from diffusing light, short pulses are used, shorter than a few nanoseconds and preferably three tenths of a nanosecond.

The emerging signal consists of any leakage from the source to the detector in the time domain of three tenths of a nanosecond. (Traveling through space at 30 picoseconds equals 1 cm) Thereafter, 3 or more nanoseconds later, the first specular reflections from the tissue are observed as shown in FIG. 5A. Numerous photons exit; in fact, a large fraction of them exit, but not all of them will exit in the direction of the objective lens. The diffusing photons then decay in intensity as they emerge farther and farther from the source impact point, as shown by the tail of curve 140 in FIG. 5A.

The detector is preferably an ICCD, since it can collect an image of the emergent photons from an area of several centimeters surrounding the point of impact of the input light. (Furthermore, notice that it is usually not possible to measure photons emergent from the source position; in this case we have the advantage of doing this.) The detected emergent photons can be integrated over the area of the ICCD detector. The information from the TRS data is in the slope of the logarithm of the intensity against the arrival time (in nanosec) according to the equation originally provided in "Time-resolved reflectance and transmittance for the noninvasive measurement of tissue optical properties" by M. S. Patterson, B. Chance, and B. C. Willson, Appl. Optics Vol. 28, 2331-2336 (1989). Thus, the detected spectrum provides directly the absorption coefficient of the biological tissue in which the photons have migrated.

The above-described TRS systems can resolve the migrating photons. After irradiation, the first 1-3 nanoseconds after irradiation, the detector detects directly reflected photons or shallow photons migrating near the tissue surface. On the other hand, 7-10 nanoseconds after irradiation, the detector detects photons from inside the tissue. The optical system can "zoom" on the selected area of the tissue surface to collect the emanating photons. By varying the magnification, the detection system detects a small image or a large image for the selected imaging mode (e.g., functional imaging or molecular imaging)

Figure 5B:
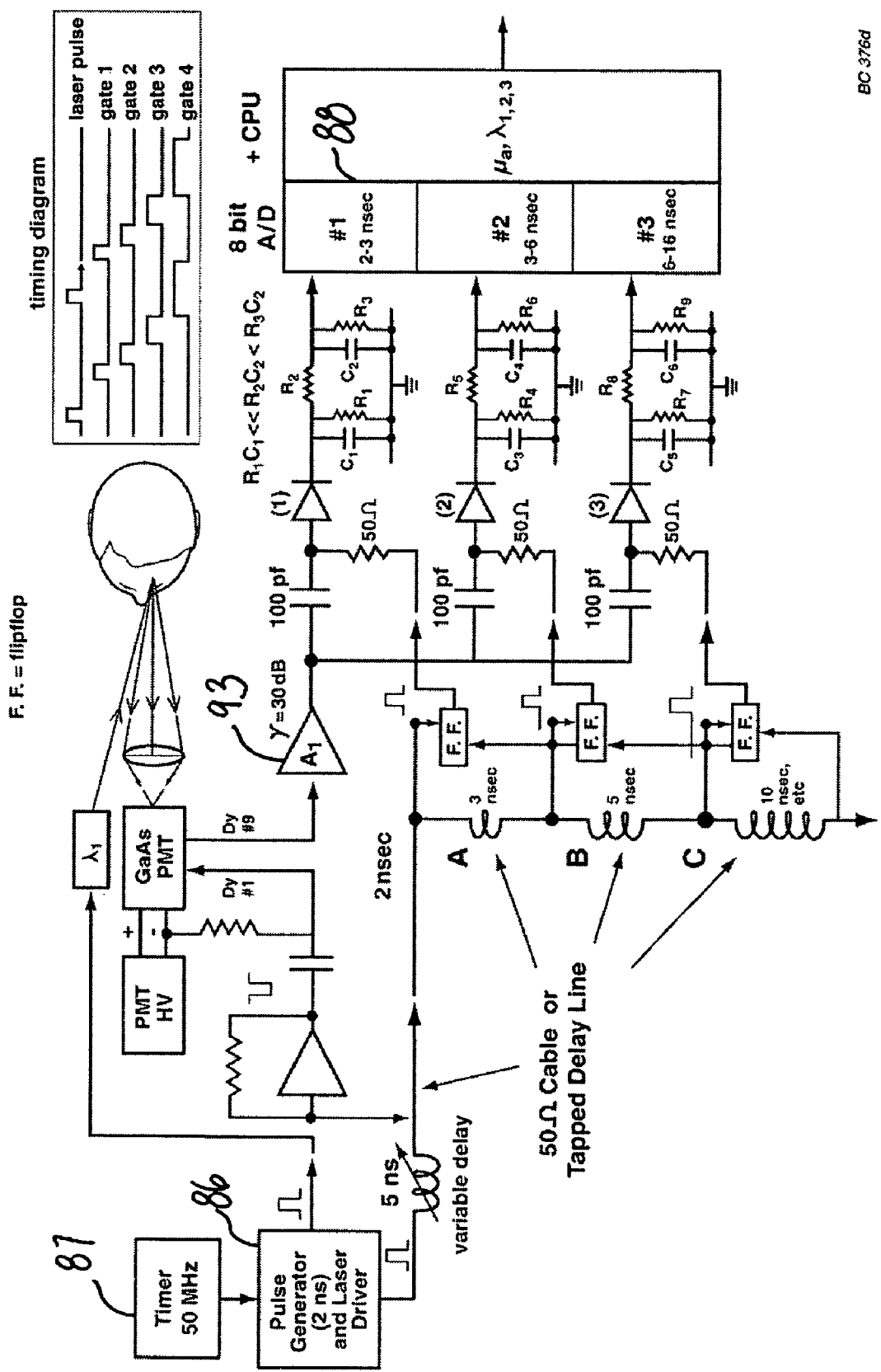
FIG. 5B shows schematically another embodiment of a non-contact optical examination TRS system having multiple gates for data integration.

FIG. 5B shows schematically a three-channel time-resolved spectroscopic system that functions as described above. The boxcar detector obtains data integration of the photon migration signal from each one of the PMT detectors. This diagram contains a negative pulse for dimension of the PMT sensitivity during the time at which specular reflections are expected to arrive at the detecting PMT. Thus, the laser driving pulse is delayed by a variable delay and inverted to give a negative pulse to the dynode number 1 of the PMT.

A very simple system term often used in TRS systems, is termed "late gate circuit." In this case, 2 pulse generators are used, one to activate the laser diode at the above mentioned powers and the other with a one nanosecond pulse, to provide a delayed pulse and "catch" the pulse train from the breast model or the breast itself. The second pulse generator generates a pulse of 5 nsec after the initial pulse, for 5-10 nanoseconds. This gate activates the PMT amplifier which signals via a pin diode to an integrating circuit for that integral at the fastest possible repetition rate, say, 50 MHz. The signal required during this late gate has been integrated with a final time constant of 1 sec. connected to the ADC and displayed on the computer screen, as known for the multiple gate or "boxcar" principle. The boxcar detector operates with a standard pulse generator which has in it a timer set at 50 MHz with a 2 ns pulse output to drive the 3 wavelength laser diodes at wavelengths of 760, 805 and 850 nanometers.

Referring still to FIG. 5B, the diagram shows the electronic circuits for boxcar multi-gate detection of signals between 3 and 20 nsec together with an electronic circuit for decreasing photomultiplier gain at the time that the different specular reflection signals are expected. The system has 50 MHz timer 87, and 2 ns pulse generator 86 which decreases the first dynode accelerating voltage as shown. The timer affords time selection of the appropriate laser diode for the wavelength system. A photo multiplier output is fed into the boxcar integrating circuits of which only 3 are shown here 88. Simply duplicating the circuits can readily increase the data handling capacity. FF represents the flip-flop, which generates impulses of appropriate duration for turning on and off the integrator at variable times as indicated. The output of the integrators is coupled to an 8 bit A to D and to a CPU for creating the absorption values and images of a single-channel detector as shown, but for multi-channel detector images, multi-channel box car integrators will be used. The detector output is coupled through 30 dB gain amplifier (100 MHz) 93 to bring the signal level to about 100 millivolts. This signal is capacity coupled to the first pin diode. This pin diode is activated at a 7 ns delay with respect to the light pulse (due to the propagation from the source to the reflecting object and back to the PMT). The first boxcar 88 is turned on for 3 ns, i.e., 10-13 ns in order to integrate the PMT signal by C1, C2, R1, R2, R3 which gives the integrated pulse signal as a DC voltage of 0-10 Hz which is coupled to an ADC and a CPU. The pin diode is switched off after 3 ns integration time by a coupling to the flip-flop giving a 3 ns integration time for the first box car interval. The second interval starts immediately thereafter with the activation of pin diode #2 and integration this time of 6 ns, i.e., 13-18 ns after the light pulse. A third integration may be used from 18-27 ns after the light pulse with a repetition interval of 20 nsec or a frequency of 50 MHz. Thus, integration of the signals in these boxcar intervals can be obtained. These intervals are arbitrary, they may overlap or a gap may occur between them. Whatever the intervals may be, the computer program is designed to fit them to a logarithmic decay curve, the slopes of which will give the values of the absorption coefficients, $\mu_a$. Tapped delay lines can be used to obtain the various intervals and that these taps can readily be computer controlled so that digital signal processing can be used to determine the optimum intervals and the number of intervals. Thus, the boxcar technology is very flexible and economical. A very small chip may be manufactured by surface mount technology to provide a large number of channels.

In order to avoid overload of the PMT we will incorporate a gain switching circuit line for the first two dynodes. This circuit is incorporated in the design of FIG. 5B and shows a decrease of voltage during the arrival of specular photons. This circuit can also be used with ICCD detectors.

The pulse generators give a satisfactory rectangular 2-nanosecond pulse, which drives the laser through a buffer amplifier. The duty ratio being 1 in 25, the heating of the laser is not expected to be significant. If not, an appropriate heat sink is available. The input current is limited by the driver circuit capability.

Two modes of operation of the circuit of FIG. 5B are possible: 1) as a peak detector where the time constant is short so that an average every 20 nsec is obtained (boxcar) and an ADC readout is taken at 50 MHz, or 2) the signal is integrated over the entire data acquisition time. In that case, the integrating time constant is long and the ADC can operate at 1 Hz. The design will make a large difference in the number of boxcar units employed. In the first case, one for each wavelength and one for each detector should be sufficient, i.e. 24 detector units from which the sample data will be A to D converted, and a new position of a source-detector "telescope" will be taken up either by galvanometer mirror deflection of the source, or movement of the entire source-detector array, as is most convenient with reflective optics.

Data sets may be stored for each position of the source-detector combination resulting in a large number of integrating detectors coupled to serial ADC readouts from all the boxcars of the samples and held at appropriate intervals. The first requires an ADC which can sample the memory circuits at any convenient time in the interval following data acquisition while the second method requires high speed digital processing.

Since integration of at least three intervals of photon decay at multi-wavelengths and multi-diode detector systems is required, this boxcar or gated detector system is proposed which may be of a short time constant or a long time constant, depending upon whether a fast or slow ADC is used. In the case of detection from five decay intervals at three wavelengths and 8 detectors, 120 boxcar integrators would be required for one complete data cycle converting these 120 outputs into digital code before starting a new set of data collection in a new position of sources and detectors. Alternatively, it would require 50 MHz ADC to digitize every transmitted light pulse, three fast ADCs, and data stores.

Referring to FIG. 6, in another embodiment, a homodyne phase modulation system 200 is used instead of the above-described examination and/or imaging systems. Phase modulation system 200 provides signal to a non-contact optical probe 12 (shown in FIG. 1) from one or several light sources (e.g., photodiodes or diode lasers) and detects light by one or several detectors (e.g., PMT or avalanche diode). For example, one source and detector pair may be used for one wavelength in the range of visible to infrared light (e.g., 650 to 900 nm). Each detector also includes an interference filter, which is important especially when the system detects excited fluorescent light. If several sources and detectors are used at the same time, the signal may be phase or frequency encoded to improve resolution in case of parallel tissue examination.

The PMS system 200 employs homodyne phase detection. A switch 202 connects, for example, laser diodes $S_1, S_2, \ldots, S_9$ to a phase splitter 204, which provides to the diodes an RF modulation signal having both a 0° phase and a 180° phase. Imaging system 200 also includes a 200 MHz oscillator 206 providing RF signal to a driver 208, which is connected to phase splitter 204. (Alternatively, an oscillator in the range of 10-1000 MHz, preferably 50-500 MHz, may be used.) A phase shifter 214 receives the drive signal (212) from driver 208 and provides the signal of a selected phase (e.g., a 0° phase change) to 90° phase splitter 216. Phase splitter 216 provides a 0° phase signal (218) and a 90° phase signal (220) to double balance mixers (DBM) 222 and 224, respectively.

A controller 240, connected to a personal computer (PC), sequences laser diodes $S_1, S_2, \ldots, S_9$ using switch 202 so that two diodes receive modulate signal at a 0° phase and a 180° phase from splitter 204. At the same time, controller 240 connects a symmetrically located PMT using switch 230 to amplifier 234. Amplifier 234 provides a detection signal to double balance mixers 222 and 224, and to a DC detector 238. Double balance mixer 222 receives the detection signal and the 0° phase reference signal (218) and provides an in-phase signal I (244). Double balance mixer 224 receives the detection signal and the 90° phase reference signal (220) and provides a quadrature signal R (242). DC detector 238 provides DC signal (246). The in-phase signal I and the quadrature signal R specify the phase ($\theta = \tan^{-1} I/R$) of the detected optical radiation and the amplitude ($A = (R^2 + I^2)^{-1/2}$) of the detected optical radiation. This phase detection circuit was described in U.S. Pat. No. 5,553,614, which is incorporated by reference.

Optical system 200 directs controller 240 to sequence the laser diodes and the PMT detectors using an appropriate timing diagram. Alternatively, several sources and detectors are used in parallel using frequency encoding. The computer stores the phase value and the amplitude value measured for each of the source detector combinations for calculating blood volume, oxygenation, or scattering coefficient. The computer can also generate images, as described below.

Figure 6A:
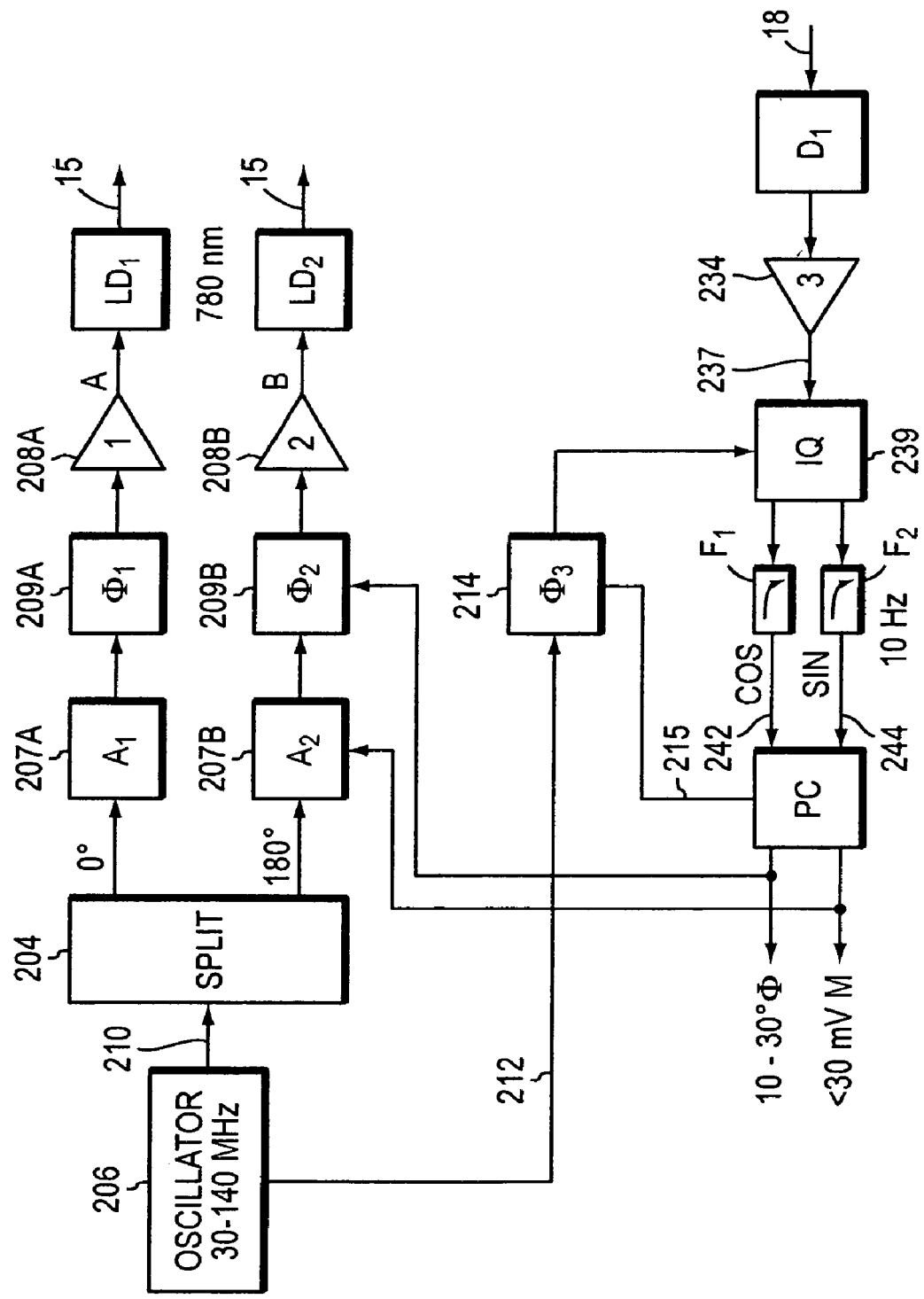
FIG. 6A shows schematically another homodyne phase-modulation system used for non-contact optical examination or imaging.

FIG. 6A shows diagrammatically one portion of phase cancellation, phased array imaging system 200. The depicted portion of imaging system 200 includes two laser diodes $LD_1$, and $LD_2$ and a light detector $D_1$ optically coupled to non-contact optical probe 12. Oscillator 206 provides carrier waveforms having a frequency in the range of 30 to 140 MHz. The carrier waveform frequency is selected depending on the operation of the system. When time multiplexing the light sources using switch 202, the carrier waveform is modulated at a lower frequency, e.g., 30 MHz to afford switching time.

When no time multiplexing is performed, oscillator 206 operates in the 100 MHz region. Splitter 204 splits the oscillator waveform into 0° and 180° signals that are then attenuated by digitally controlled attenuators 207A and 207B by 0% to 10% in amplitude. The phase of the attenuated signals is appropriately shifted by digitally controlled phase shifters 209A and 209B in the range of 10°-30° and preferably 20° in phase. Laser drivers 208A and 208B drive $LD_1$ and $LD_2$, respectively, which emit light of the same wavelength, for example, 780 or 800 nm. After the introduced light migrates in the examined tissue, a PMT detector $D_1$ amplifies the detected signals having initially the 0° and 180° phases. As described above, for homogeneous tissue and symmetric locations of $LD_1$, $LD_2$, and $D_1$, the output of the PMT is 90°, i.e., halfway between 0° and 180° and the amplitude is close to zero. The PC adjusts the attenuation provided by attenuator 207B and the phase shift provided by phase shifter 209B so that detector $D_1$ detects phase nominally around 25° and amplitude nominally around $\leq 10$ millivolts for homogeneous tissue. This signal is connected to amplifier 234 and to the IQ circuit 239. The cosine and sine signals are fed into the personal computer, which takes the amplitude (the square root of the sum of the squares of I and Q) and the phase angle (the angle whose tangent is I/Q) to give outputs of phase around 25° and amplitude signals around 10 millivolts. The personal computer also adjusts the reference signal to the IQ to have the phase $\phi_3$ between 10° to 30° and preferably around 25°, i.e., phase shifter 214 provides to IQ circuit 239 the reference phase having a value selected by the combination of phase shifters 209A and 209B.

Splitter 204 may be a two way 180° power splitter model number ZSCJ-21, available from Mini-Circuits (P.O. Box 350186, Brooklyn, N.Y. 11235-0003). Phase shifters 209A, 209B and 214 and attenuators 207A, and 207B are also available from Mini-Circuits, wherein the attenuators can be high isolation amplifier MAN-1AD. IQ demodulator 239 is, for example, the demodulator MIQY-140D also available from Mini-Circuits.

The system obtains the initial values of attenuator 207B ($A_2$) and phase shifter 209B ($\phi_2$) on a model or a symmetric tissue region (e.g., the contralateral breast or kidney or another region of the same organ that is tumor free). The non-contact probe may be calibrated on a tissue model by storing the calibration values of $A_2$ and $\phi_2$ for the various source-detector pairs (e.g., for different wavelengths, to obtain baseline values or a baseline image). The non-contact probe is then directed to the examined breast or abdomen, for example, and the phases and amplitudes are detected for the various source and detector combinations. When the contralateral "tumor free" kidney is used as a model, the probe is transferred to the contralateral kidney (taking note to rotate the probe because of the mirror image nature of the kidney physiology) and then the images are read out from all the source-detector combinations to acquire the tissue image.

There is no limitation on multiplexing as long as the bandwidth of $F_1$ and $F_2$ is recognized as being the limiting condition in the system normalization. The normalization is accurate and without "dither" to achieve a significant amount of filtering in $F_1$ and $F_2$, i.e., less than 10 Hz bandwidth. If $\phi_2$ is adjusted over a large range, there will be amplitude-phase crosstalk. Thus, the system may adjust phase and then amplitude and repeat these adjustments iteratively because of the amplitude phase crosstalk. The control of $A_1$ and $\phi_1$ provides even a greater range of control, where obviously inverse signals would be applied to them, i.e., as the $A_1$ and $\phi_1$ signals are increased, the $A_2$, $\phi_2$ signals would be decreased. Both $A_2$ and $\phi_2$ can be controlled by PIN diodes, to achieve an extremely wideband frequency range. However, since signal processing controls the bandwidth of the feedback system, either PIN diode or relay control of the phase and amplitude is feasible for automatic compensation. If dual wavelength or triple wavelength sources are used, each one of them is separately calibrated for the intensity and position relative to the examined or imaged tissue.

The PMS system separates the detected "useful" photons from the "unwanted" specular or surface-scattered photons computationally by a Fourier transform on all detected data. That is, the TRS system separates the detected "useful" photons (which have migrated in the examined tissue) from the "unwanted" specular or surface-scattered photons by adjusting the detection gates to eliminate the photons that arrive much earlier (i.e., to eliminate photons that are not delayed by the photon migration in the examined tissue). As described in the above-cited publications, the detected PMS signal (in the frequency space) corresponds to the detected TRS signal (in the time space) via a Fourier transformation. Therefore, the detected PMS signal (including both the "useful" photons and the "unwanted" photons) is Fourier transformed from the frequency domain to the time domain. Then, the processor eliminates the initial portion corresponding to the "early" arriving photons. The "later" arriving photons had migrated in the examined tissue and thus carry information about the tissue properties.

As described above, the optical data can be collected over two symmetrical tissue regions (e.g., the left breast and the right breast, or two symmetrical brain lobes expected to have the same optical properties for normal tissue). Any difference in the optical properties corresponds to a tissue abnormality (e.g., bleeding or tumor), or different functional use of the brain tissue manifested as changes in blood oxygenation or in a blood volume in the examined tissue. For example, tapping with fingers of the right hand can be functionally detected in the left brain hemisphere. The "functional" data can be compared to the rest of the data to obtain a baseline image. The optical data sets are processed using an imaging algorithm, for example, a back projection algorithm known in computed tomography (CT).

The collected data sets are processed using an imaging algorithm. The imaging algorithm calculates the blood volume of the examined tissue for each source-detector combination for each data set. The imaging algorithm can also calculate the oxygenation of the examined tissue for each source-detector combination.

The blood volume or oxygenation images can be subtracted from "model" images. The blood volume image can be subtracted from the oxygenation image to create congruence data (further described below) to localize and characterize a tissue anomaly. The imaging algorithm may also create an image using the differential image data sets. Prior to creating the image, an interpolation algorithm is employed to expand the differential image data set, containing 16 (4×4) data points, to an imaging data set containing 32×32 image points.

Alternatively, the computer uses a back projection algorithm known in computed tomography (CT) modified for light diffusion and refraction and the banana like geometry employed by the optical imaging system. In the optical back projection algorithm, the probabilistic concept of the "photon migration density" replaces the linear relationship of ballistically transmitted X-rays, for the beam representing pixels. The photon migration density denotes a probability that a photon introduced at the input port will occupy a specific pixel and reach the detection port. For different types of tissue, the phase modulation spectrophotometer provides the values of the scattering and absorption coefficients employed in the probability calculations. (These values are determined as described in U.S. Pat. No. 5,402,778, which is incorporated by reference.) In the image reconstruction program, the probability is translated into a weight factor, when it is used to process back projection. The back projection averages out the values of information that each beam carries with the weighting in each pixel. The specific algorithms are provided in U.S. Pat. No. 5,853,370 issued on Dec. 29, 1998.

A method for correcting blurring and refraction used in the back projection algorithm was described by S. B. Colak, H. Schomberg, G. W.'t Hooft, M. B. van der Mark on Mar. 12, 1996, in "Optical Back projection Tomography in Heterogeneous Diffusive Media," which is incorporated by reference as if fully set forth herein. The references cited in this publication provide further information about the optical back projection tomography and are incorporated by reference as if fully set forth herein.

The above described non-contact systems provide the possibility of examination of brain function or interrogation of a large number of people; for example, in line for baggage check-in at an airport. As described in U.S. application Ser. No. 10/618,579, which is incorporated by reference, the examined individuals may be asked to answer several security questions (e.g., "Did anybody else pack your luggage?") displayed on a computer terminal. As the individuals are looking at the computer terminal, there is a spectroscopic system with a source and a detector for brain examination. The non-contact spectroscopic system can use a number of wavelengths in the NIR region, presumably those emphasizing the less visible light, at 780 nm, 805 nm, or 850 nm.

Pursuant to an approval (if required), each individual may be surveyed by a gated CCD camera that images the forehead, including separately the facial expression. This system tracks various individuals who are giving extraordinary oxygenation and or blood signals measured by any of the above-referenced spectroscopic systems, suggesting "suspicious" mental activity. Since the check-in lines often last a half hour, any particular person might be tagged for more detailed studies or other studies could be accomplished separately.

As described in U.S. application Ser. No. 10/618,579, the spectroscopic system creates separate images for blood volume and blood oxygenation. The images include numerous voxels of data generated using histograms or other methods known in the art. The spectroscopic system is then used as a "deceit measure detector" by checking for a specific signal at one or several signature voxels for lying (e.g., examining blood volume and signals) when the subject is lying while answering questions provided at the check-in line at the airport. On the other hand, the system detects a weak signal at the signature voxel when the subject is telling the truth. The system can automatically design questions displayed at the computer terminal, where the answer is known to provide "control images" for each person. For example, based on the booked airline ticket, the system asks questions related to the name, address, sex and other known information about the individual. (In the image, the system looks for extraordinarily high blood volume or oxygenation signals and their possible congruence as described in PCT Application PCT/US99/03030, which is incorporated by reference.)

Figures 7, 7A:
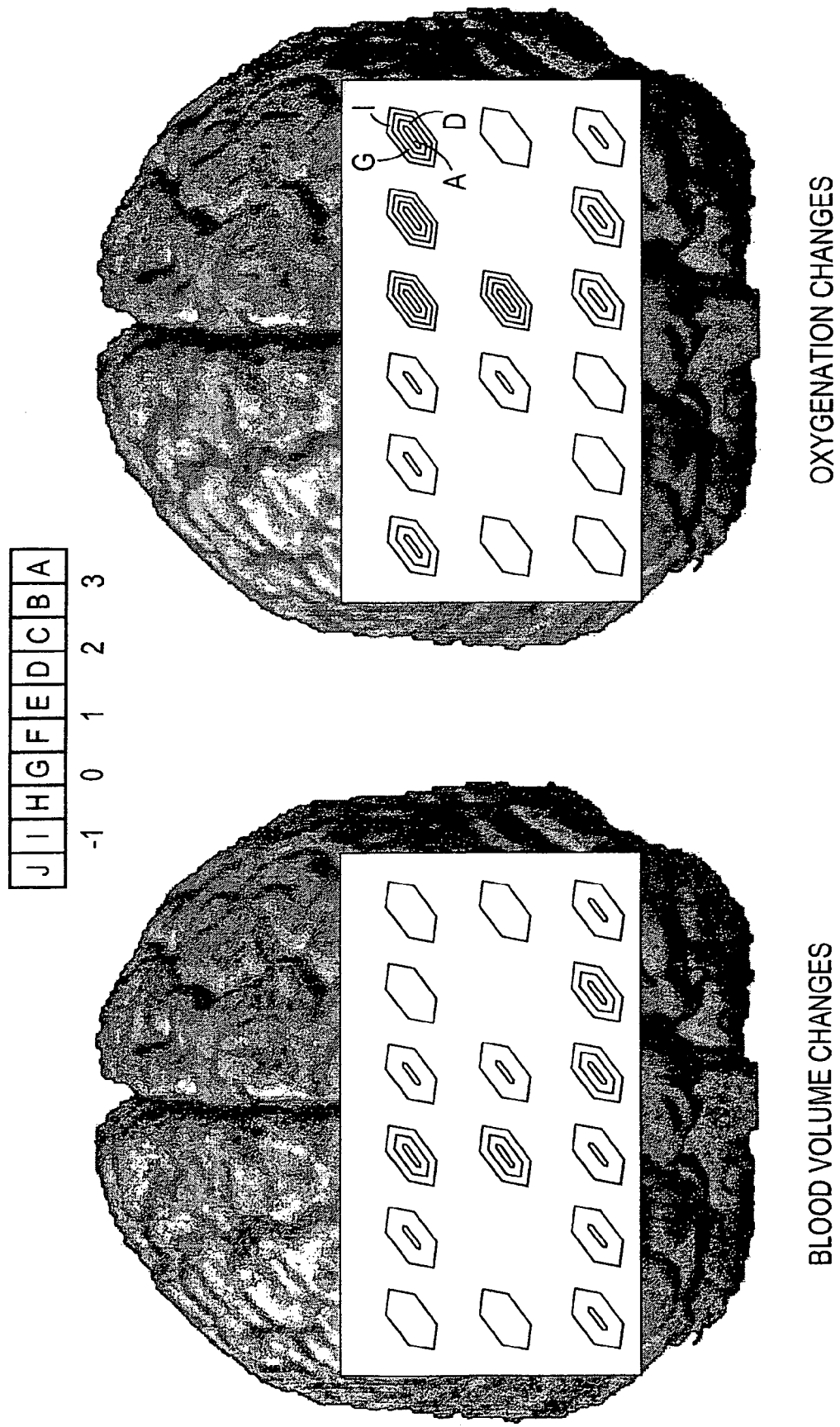
FIGS. 7 and 7A show example of optical images corresponding to blood volume changes and oxygenation changes, in the frontal lobe, when solving 8 letter anagrams by a human subject.
Figure 7C:
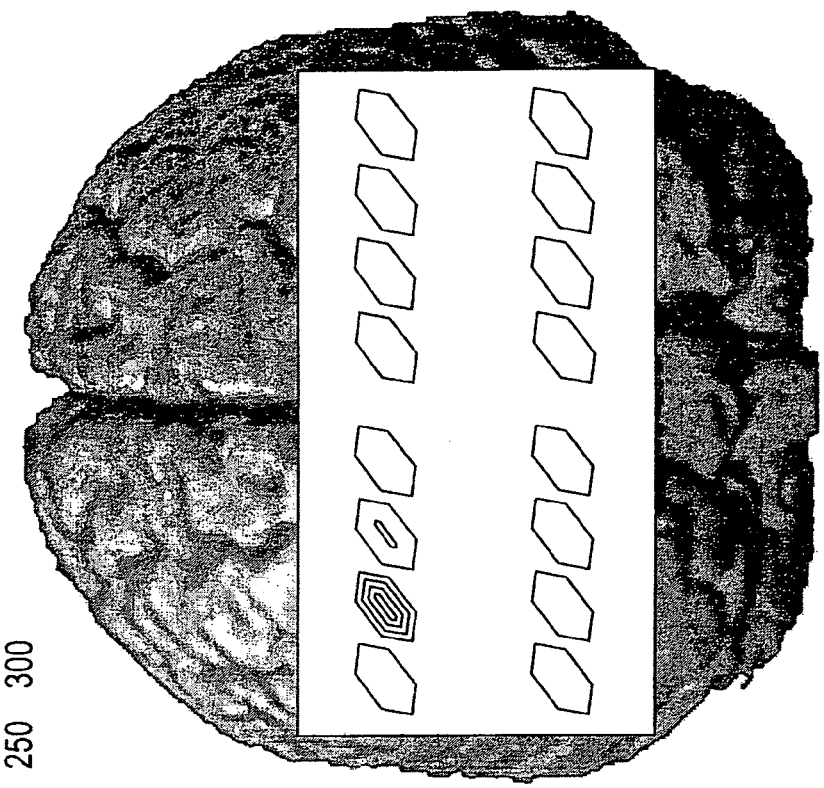
FIGS. 7B and 7C show example of optical images corresponding to oxygenation changes, in the frontal lobe, when the examined subject tells a lie and the truth, respectively.
Figure 7B:
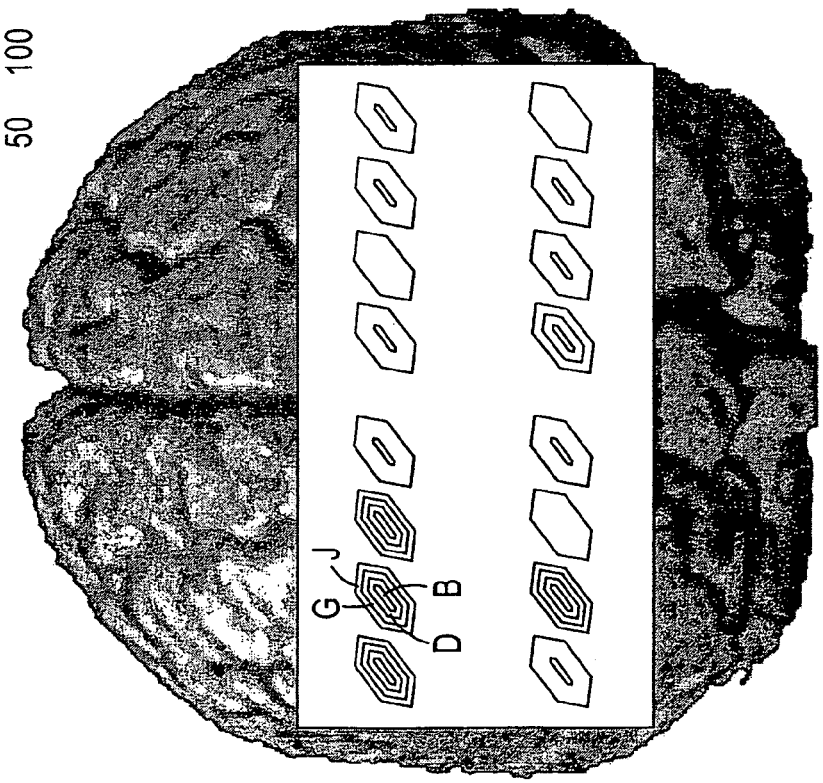
Figure 7D:
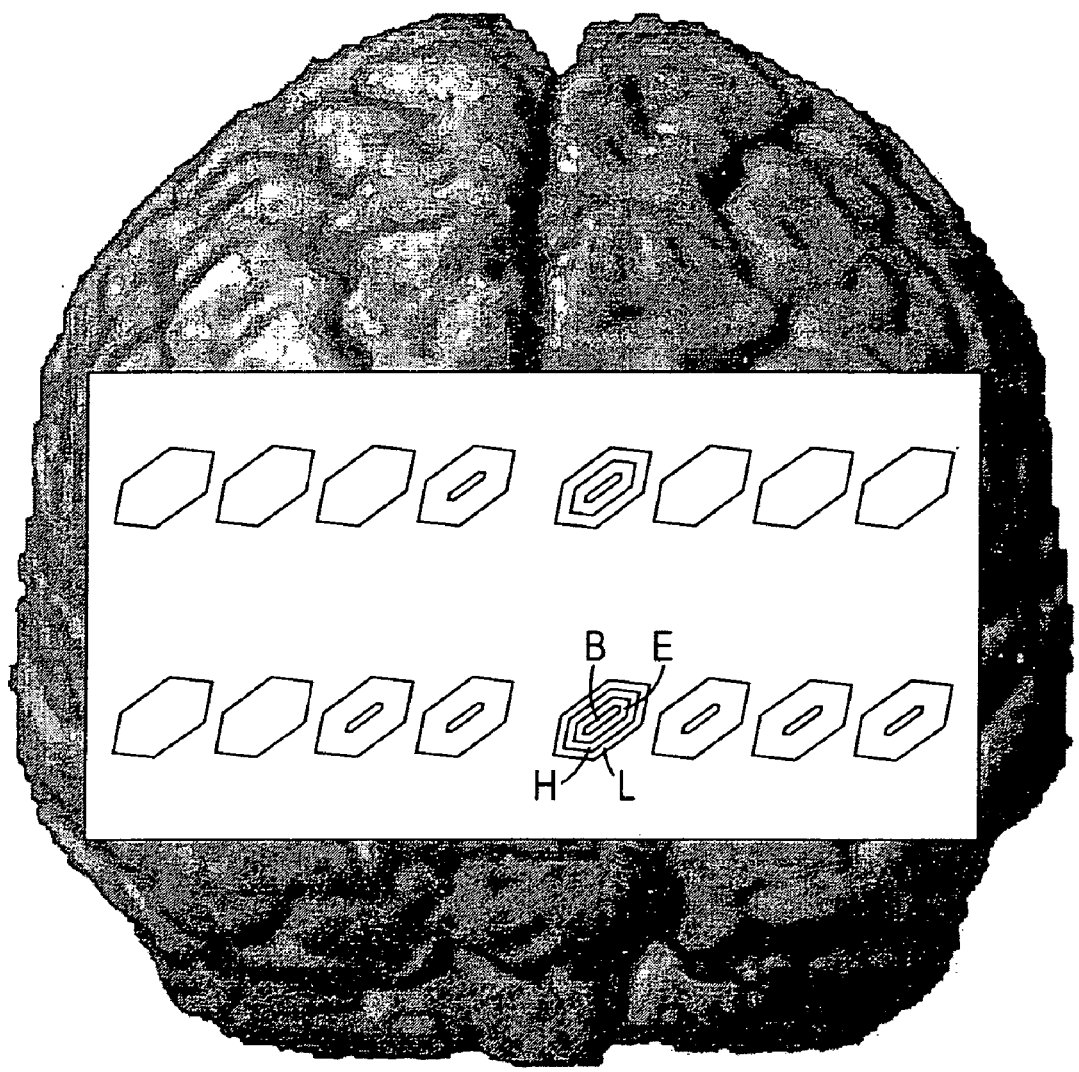
FIG. 7D shows an example of a sudden insight optical image for oxygenation changes, in the frontal lobe, 15 seconds after solving an anagram minus 15 seconds before solving the anagram.

FIGS. 7, 7A, 7B, 7C and 7D show optical images of the frontal lobe generated by the optical system of FIG. 1 described in the co-pending U.S. application Ser. No. 10/618,579 (incorporated by reference). The contactless optical system 10 (FIG. 1) can generate similar images. FIGS. 7 and 7A show optical images corresponding to blood volume changes and oxygenation changes, in the frontal lobe, when solving 8 letter anagrams by a human subject. FIGS. 7B and 7C show optical images corresponding to oxygenation changes, in the frontal lobe, when the examined subject tells a lie and the truth, respectively. FIG. 7D shows a sudden insight optical image for oxygenation changes, in the frontal lobe, 15 seconds after solving an anagram minus 15 seconds before solving the anagram.

Referring to FIGS. 7B and 7C, based on the detected intensity at each measured voxel of the image, the optical system can determine the "deceit" level corresponding to the answer of the examined subject. Generally, based on the "background" image of an individual, when an individual is telling the truth, the oxygenation images include one or two highly pronounced voxels (FIG. 7C). When the examined individual is lying, the oxygenation images usually provide a large number of active voxels, as shown in FIG. 7B.

In general, the above-described embodiments examine biological tissue (i.e., in vivo human tissue, animal tissue, or animal model) by measuring tissue absorption, tissue scattering or fluorescent emission from one or several selected molecules located in the tissue. Using visible, near-infrared or even infrared light, the above described systems image the tissue to provide a detailed characterization of the examined tissue. This includes characterization of tumors or other tissue in homogeneities associated with diseases (e.g., breast cancer or brain stroke) and characterization of normal tissue including cognitive processes.

According to one field of use, the above-described optical non-contact system may also be used at the security location to check for magnetic objects. While in the other two examinations, i.e. waiting for baggage check-in, or ticket check-in, ample time is available because the process can take respectively 30 minutes or 5 minutes, in the latter case taking into account that the rhetorical, "Have you had your baggage with you at all times?" has routinely been answered by a lie. In special security, which indeed should be curtained off (i.e. public examination is demeaning, and where the shoes are examined, etc.), it is certainly stressful and a few questions could certainly be asked and the response noted. Any person with a particular hat covering the forehead, or nodding their head during the scanning process so as to confound the image would immediately be suspect, and additional screening would be conducted.

According to another aspect of the present invention, the scanning system is a "radar-like" frontal surveillance system that includes not only close-up applications, for example, where a person is singled out and interrogated (for example, using the TRS system imaging his forehead with ICCD camera technology). In this system, laser light is scanned over the person's forehead to obtain optimal signal-to-noise ratio of image data processed as described in Appendix A. The system provides diffuse illumination and background signals are minimized by standard radar techniques, for example, by moving target indication, which would select out anyone who is moving the head while in the security line and distinguish them from multiple reflection images.

As described above, the ICCD image acquisition is gated to receive light in the first 10 nsec. The system concentrates on the less visible NIR wavelengths, such as 780, 805 and 850 nm and is beset by multiple reflections of the excitation light from surrounding objects, which might be delayed sufficiently to obscure the photon migration signal from the forehead.

Alternatively, the system may generate an image using only ballistic photons, as known in the spectroscopic art. The detector need not be an ICCD but could be a mosaic of detectors such as a multi-anode Multi-Channel-Plate detector (MCP), etc. And if, indeed, the photons are ballistic, it just means there is minimal scattering and an image taken with CW or phase would serve just as well. In fact, this might be the case where phase modulation imaging might come to the fore because it is so much simpler than the pulse time imaging.

Any of the above-described systems may be constructed as an attachment to notebook computers so that the user would be monitored for alertness by a flying spot scan over the forehead or an area of illumination taking advantage of the fact that a TRS system affords a time separation of the illumination pulse and the re-emitted light, as described above. For airport detection, the prefrontal imaging can occur either covertly or with consent. Advantageously, there is nothing to be "put on the subject" and the brain scan can start immediately where the subject is, for example, at an examination booth or by looking at a monitor. The same thing goes for an interrogation procedure, which is more convenient if the scanner is part of the interrogation. Great care is taken so that the generated laser beam is not directed to the subject's eyes. The scanner can operate at room light since it would be in the NIR region and suitable filters would allow room light illumination in shorter wavelengths than NIR.

With respect to immobilization, this is not a high-resolution system and head motions of a few millimeters are quite acceptable, since we expect the activation to cover a significant area, 2-3 $cm^2$. However, in covert detection one would obviously have a TV system as well which would allow one to track the head and to shift the laser beam to illuminate the same spot or spots of the forehead regardless of movement.

The above-described optical systems examine or image in vivo, non-invasively biological tissue (e.g., the breast tissue of a female subject or the brain). The system's controller (e.g., a notebook computer) controls the operation of the light source and the light detector to detect light that has migrated inside the examined tissue. A processor receives signals from the detector and forms at least two data sets. The first data set represents, for example, blood volume in the examined tissue, and the second data set represents, for example, the blood oxygenation in the examined tissue. The processor correlates the first and second data sets for the same tissue region to detect abnormal tissue in the examined tissue region. The second data set may include hemoglobin deoxygenation values, or hemoglobin oxygenation values.

The processor may also receive data and form a third data set, collected by irradiating a reference tissue region having similar light scattering and absorptive properties as the examined tissue region. The processor may also receive data and form a fourth data set, collected by irradiating a tissue model having selected light scattering and absorptive properties.

The processor is also constructed arranged to correlate the first and second data sets (or the first and third data sets, or the first and fourth data sets) by determining congruence between data of the two or more sets. These data sets are preferably images (e.g., absorption images or fluorescent images). The congruence is described in detail in the PCT application PCT/99/03066; the PCT application PCT/99/02953; and the PCT application PCT/99/03030, all of which are incorporated by reference. The congruence or two or more data sets, or images, increases the sensitivity of detection and tissue characterization, before, during and after administering a chemical agent or a pharmacological agent. The congruence or two or more data sets, or images, may be performed over time to study the kinetics.

According to another field of use, the optical system measures tissue absorption, tissue scattering or fluorescent emission from one or several selected molecules located in the tissue. The above-described systems image the tissue to provide a detailed characterization of the examined tissue. This includes characterization of tumors or other tissue in homogeneities associated with diseases (e.g., breast cancer or brain stroke). Furthermore, this characterization includes the analysis of molecular pathways leading to diseases or molecular imaging for drug agent or drug agent precursors where animal model is used to model a human disease.

The above-described optical systems may be used for measuring perfusion and metabolism associated with new blood vessel formation (i.e., angiogenesis). One example for contact irradiation and detection is provided in U.S. application Ser. No. 09/383,476, filed on Aug. 26, 1999, which is incorporated by reference. The described optical system is used for measuring angiogenesis and the influence of an administered drug on the examined tissue. The presence or absence of angiogenesis is associated with multiple diseases, such as cancer and cardiac disease.

Furthermore, the described optical systems may be used to detect naturally occurring fluorescent compounds or injected fluorescent compounds. The optical imaging allows specific tagging of particular receptors, antibodies, genes, or drugs. This tagging enables the detection and quantification of a compound and the detection of biodistribution and pharmacokinetics. The molecular images are used to understand processes associated with progress of diseases and treatment.

The time-resolved spectroscopy and phase modulation spectroscopy have numerous advantages. They are used to measure quantitatively tissue absorption and scattering coefficients allowing precise pharmacokinetics and biodistribution of molecules including fluorophores/chromophores. The time-resolved spectroscopy and phase modulation spectroscopy provide the depth sensitivity of the introduced photons. The can measure the fluorescence lifetime, which changes with deviations in the physiological environment (pH, oxygen saturation, ion concentration). They can discriminate between two or more fluorophores whose emission spectra overlap, thus allowing the analysis of drugs used in combination therapy.

Another embodiment is directed to molecular imaging and functional imaging. Functional imaging non-invasively monitors physiological processes in the examined tissue, primarily based on blood flow and cellular metabolism. Molecular imaging further images one or several selected, targeted processes and pathways in the examined tissues (including cells located in the tissue). Both the functional imaging and the molecular imaging are performed by the time-resolved spectroscopy or phase modulation spectroscopy using the above-described systems.

The molecular imaging system (i.e., using the time-resolved spectroscopy, TRS, or the phase modulation spectroscopy, PMS) measures absorption and scattering properties, fluorescence intensity and fluorescent lifetime. The combination of these values provides more tissue characteristics and improves the contrast of the collected image. This improved image is used for the analysis of drugs used in various types of treatment (including the combination therapy). This image can resolve cells or fluorophores located at the same wavelength. The changes in fluorescence lifetime occur in different environments such as varying tissue pH and oxygenation levels. Thus by detecting the effect and changes of the environment, the above-described systems can characterize various processes. These processes can be studied in tissue models, in small animals, or in human tissue (under approved protocols) to study pharmacological agents and their effect on the diseased tissue.

Molecular imaging can take the advantage of the optical properties of naturally occurring metabolites and their original optical properties. Other molecules can be added to a system, as well, to track naturally occurring molecules that are difficult to observe, or for other purposes. The studied molecules can also have a fluorescent tag added to them for optical tracking. Fluorescent probes, which bind to a particular molecule, can also be added to a system for the study of a particular molecule. For example, a fluorescently tagged antibody to a known cancer-specific protein being studied can be injected into a system to visualize and determine localization of the protein being studied. This can also be done with receptor agonists and antagonists, or other small molecules. Fluorescent tags and probes are generally safe, and do not interfere with other metabolic processes. The above-described systems can very closely optically track molecules of interest in the examined tissue. The systems can not only detect, but also characterize a tissue tumor prior to and in response to treatments with or without administering a pharmacological agent. The optical tracking of the molecules is a very sensitive and can measure metabolism of the molecule, its density, localization and quantity in the examined tissue.

Figure 8A:
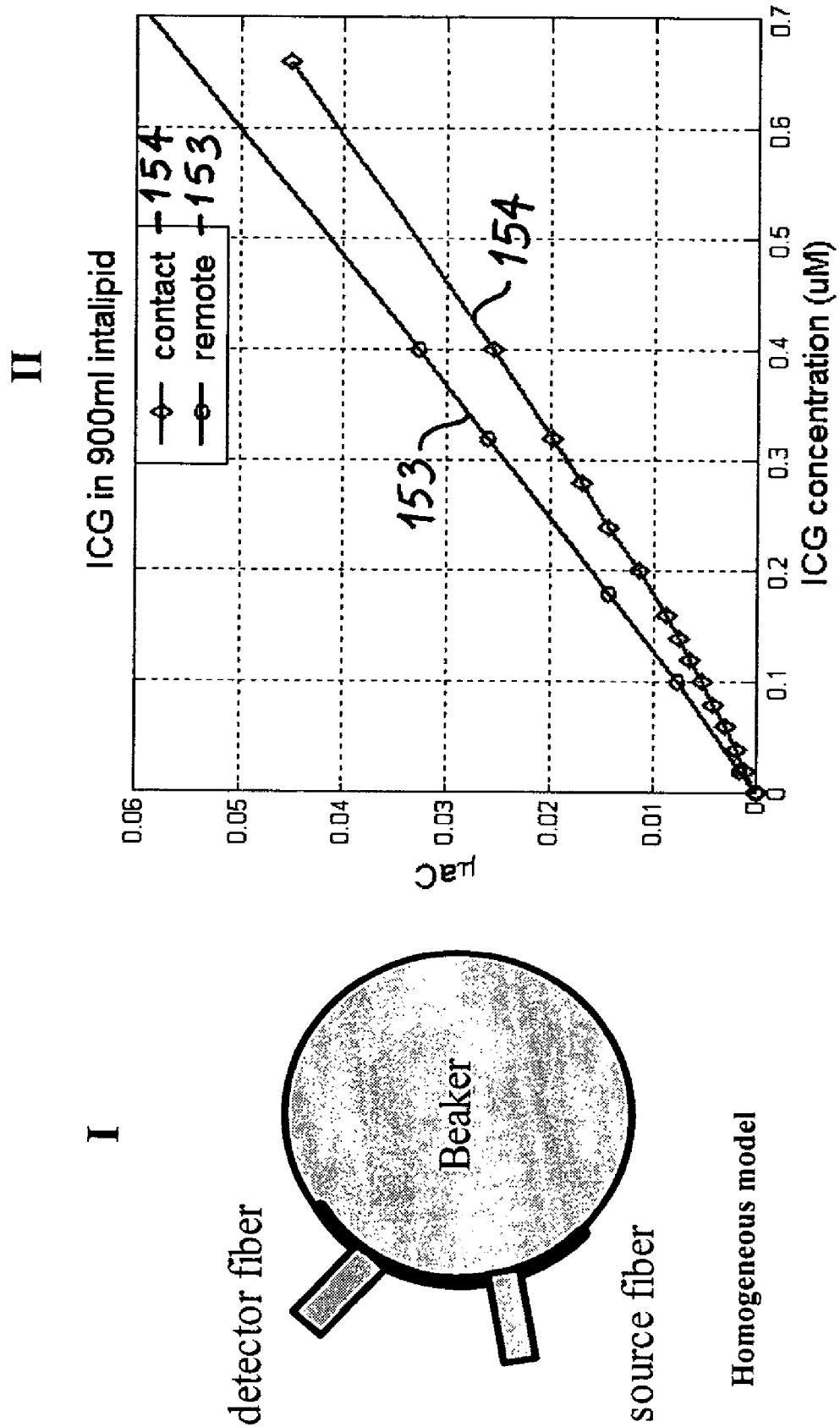
FIG. 8A shows a homogeneous model used for a contact TRS system on a liquid solution with varying concentration of ICG.
Figure 8B:
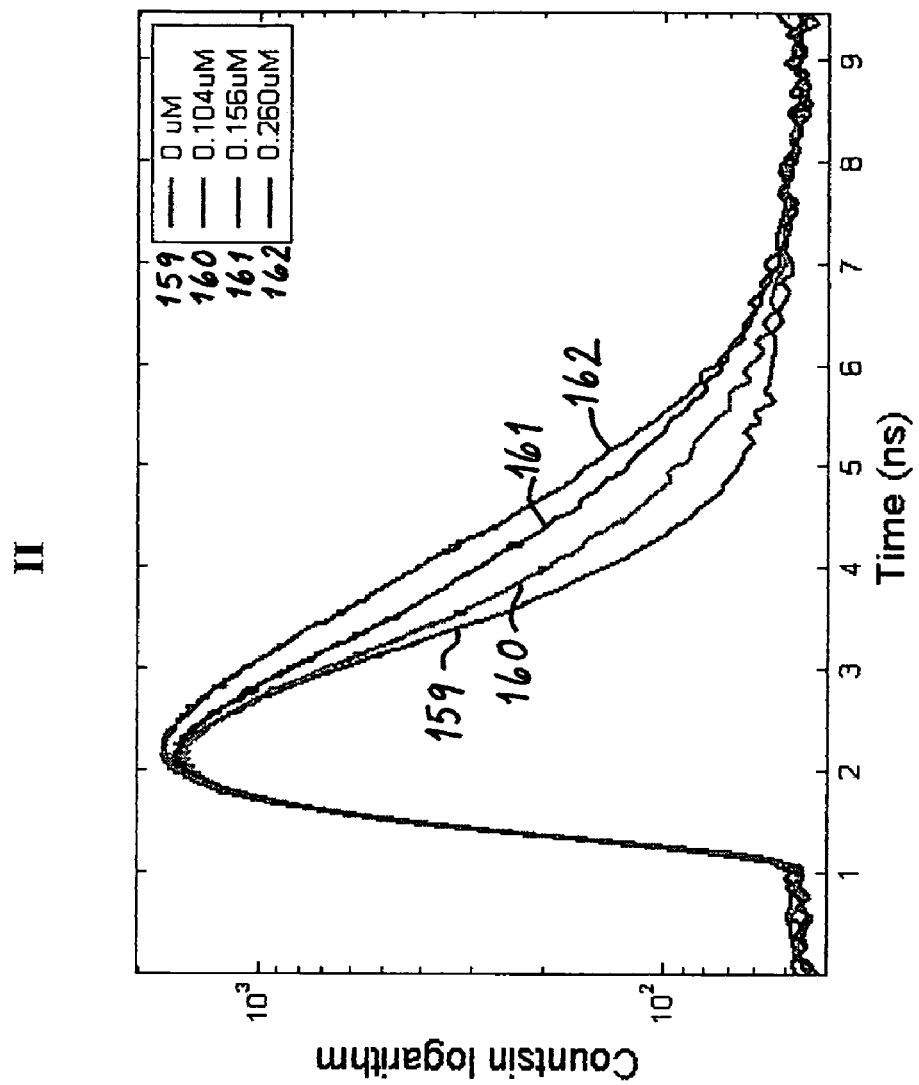
FIG. 8B shows a homogeneous model used for a remote, non-contact TRS system on a liquid solution with varying concentration of ICG.
Figure 8B:
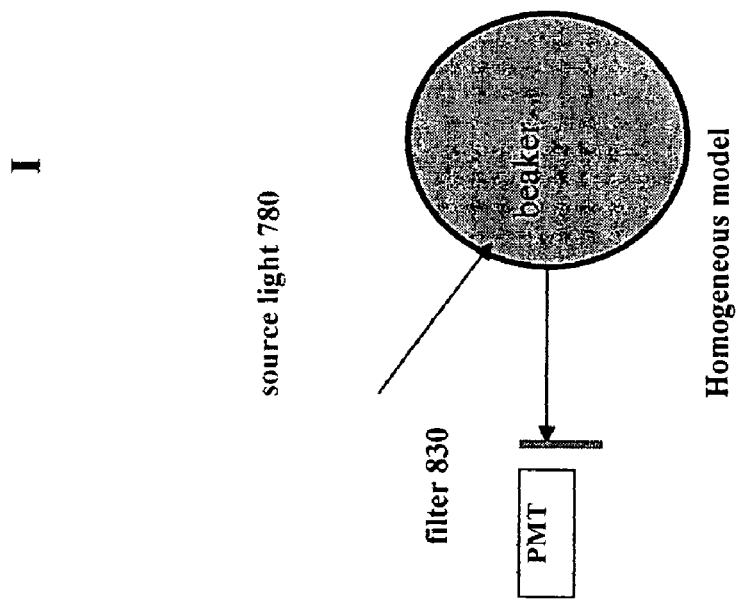

FIG. 8A illustrates a homogeneous system for comparing the performance of the remote, non-contact optical system with the contact optical system (using fiber optics). FIG. 8-I illustrates a liquid homogeneous model with the fluorescent dye indocyanine green (ICG), and the geometry of contact TRS source and detector fibers with respect to a 900 ml beaker. The beaker includes an intralipid solution and variable concentrations of ICG plotted in FIG. 8A-II. For the varied amounts of ICG (solutions from 0.01~0.7 μM ICG with intralipid), the absorption coefficient was measured by both the contact TRS system and the remote, non-contact TRS system (See FIGS. 8A-I and 8A-II).

FIG. 8A-II shows the slope of the log of photon decay curve to get $\mu_a$, obtaining a somewhat more linear relationship for remote sensing (153) than for contact sensing (154) due to the fact that the detector is more linear with the lowest signal. The agreement of absorption coefficient $\mu_a$ measurements is quite good between contact and remote TRS, however, given the difference in method. FIG. 8A-II also shows that the $\mu_a$ of ICG is linearly proportional to ICG concentration. Photon counts for 0.24 μM ICG are, for contact TRS, $1 \times 10^4$, and for remote TRS, $1.5 \times 10^3$. The ratio is about 1/7.

FIG. 8B-I illustrates the remote, non-contact TRS system using a 780 nm light source with respect to the set-up of the intralipid solution beaker containing variable concentrations of ICG tested, as well as the detector with the 830 nm filter. FIG. 8B-II shows the detected fluorescence intensity from 0~0.26 μM ICG in 1200 ml of intralipid solution. FIG. 8B-II also shows that photon decay, time and intensity increase as ICG concentration increases.

FIG. 8B II shows the fluorescence spectra, but the specular reflection is at excitation wavelength that is not detected by the PMT. The remote, non-contact TRS system operating in the fluorescent mode is also suitable for detection of molecular beacons, an 830 nm, where 780 nm excitation light pulses were used. The count rate of the fluorescence signal was $10^3$ compared to the count rate of $2\times10^3$ for the absorption.

Figure 9:
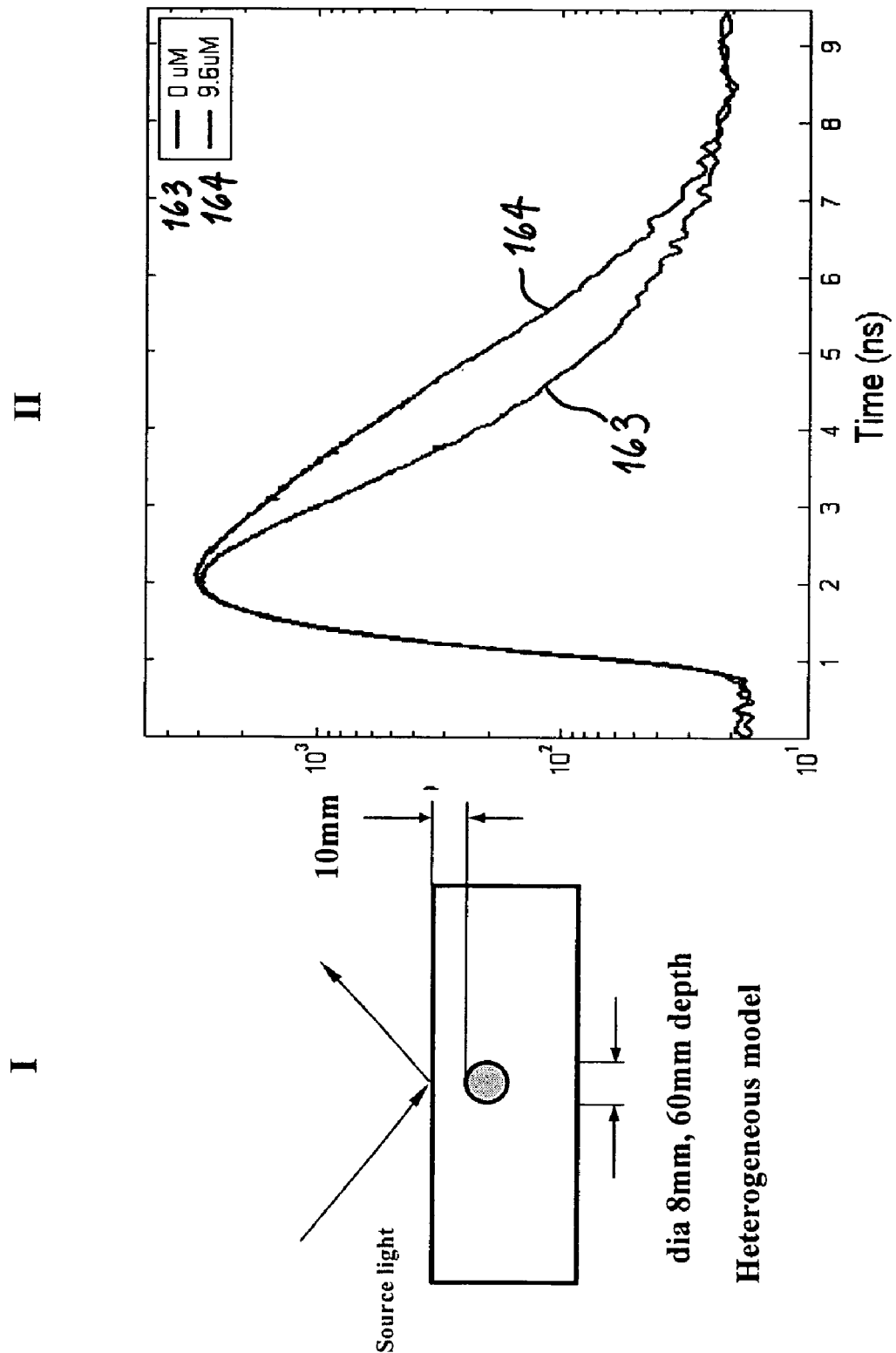
FIG. 9 shows a heterogeneous model for comparing a contact TRS system and a remote, non-contact TRS system on liquid solution and a container with ICG.

FIG. 9 shows a heterogeneous system with two objects, illustrating breast tumor detection. The first object is a vessel with intralipid solution (providing a signal 163), and the second object is a vessel with ICG (providing a signal 164). The fluorescence excitation is used to detect the object containing ICG. The data show that the nearby object lacking ICG does not perturb the detection of the object containing ICG. The fluorescence intensity from the local marker is 0~9.6 µM ICG in 8 ml intralipid, and the container with the objects is in the hole, in hard phantom. These data illustrates that the remote TRS able to distinguish a breast tumor (i.e., cancerous tumor) against the heterogeneous background of Ductal and Adipose tissue.

The above tests preliminarily show that the remote, non-contact TRS system works with fluorescent molecular markers, such as ICG. The absorption coefficients for ICG samples measured using both the contact and remote TRS systems were in good agreement. The fluorescence is a desirable quality due to specular reflection being at excitation wavelength, and phantom effects are not a concern.

Figure 10B:
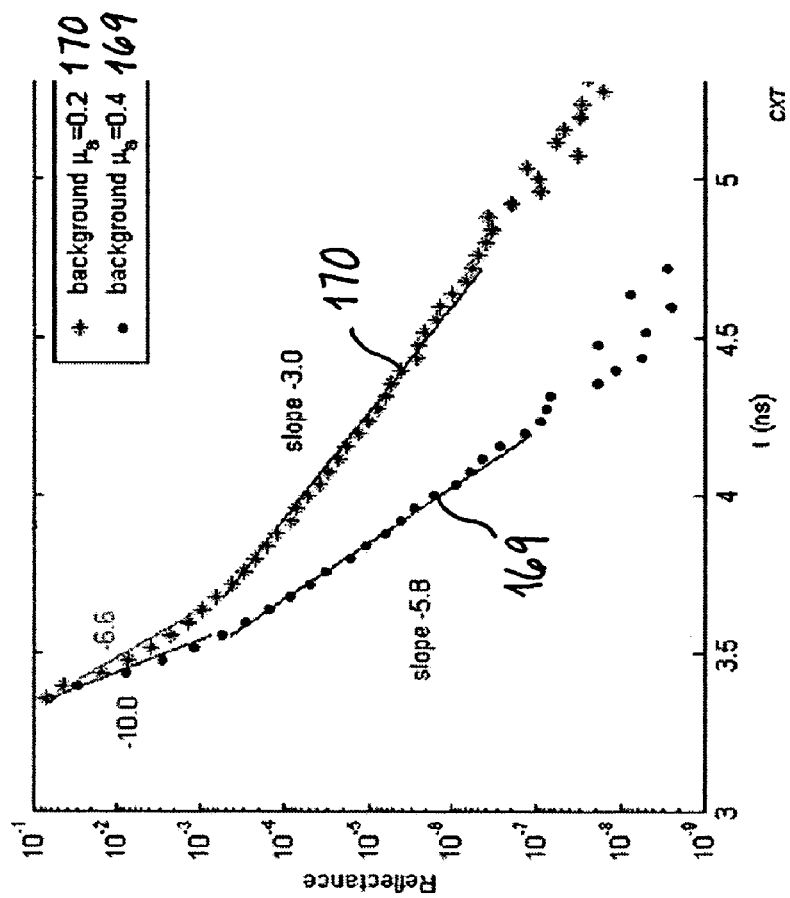
FIGS. 10A and 10B show a model of Monte Carlo simulation of remote TRS data.
Figure 10A:
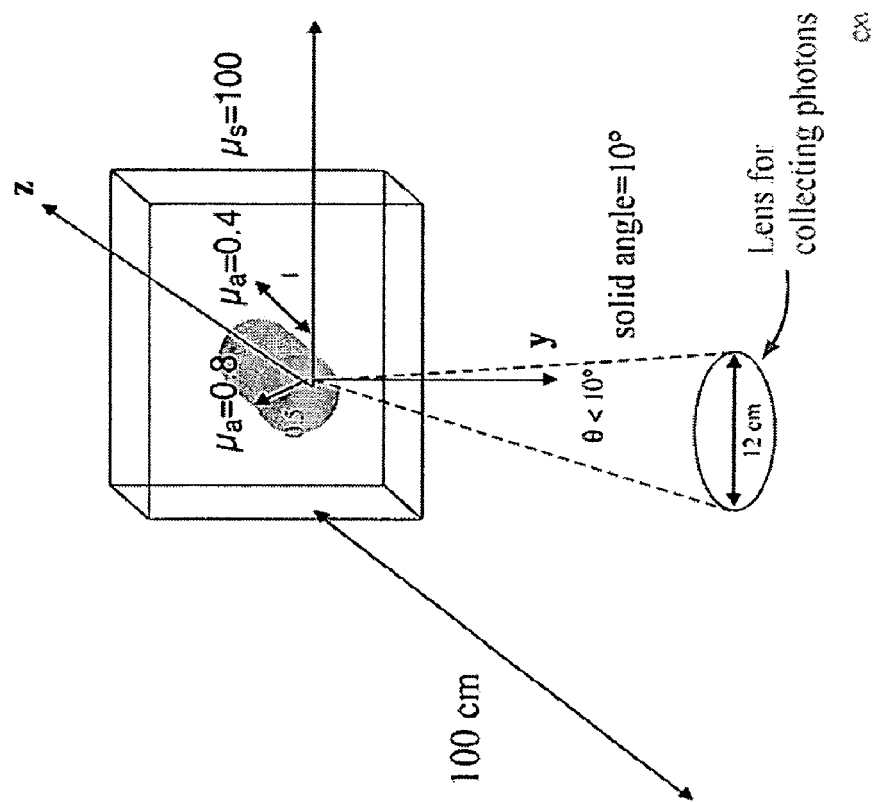

FIGS. 10A and B, shows the Monte Carlo simulation of time-resolved spectroscopy in time-domain of remote detected reflectance done to initiate experiments. Sufficient photons ($10^7$) were introduced in order to achieve an accurate slope in 10B. These simulation results strongly support the proposition that remote sensing of diffusive photons technology is feasible. In fact, simulation of contact and remote TRS does give the same log slope to within 5%. Ab initio, in FIG. 10A, 1 embedded object (1 cm$^3$) which has a much higher absorption coefficient than background can be detected. The distance between subject and source/detector is 1 m (111). The lens has a solid detection angle of ~10° (112). Semi-infinite medium with $\mu_a$=0.4 cm$^{-1}$, $\mu_s$=10 cm$^{-1}$ with a small object 115 embedded (1 cm×0.5 cm) of $\mu_a$=0.8 cm$^{-1}$ and same $\mu_s$.

FIG. 10B shows Monte Carlo simulation of photon migration tracks with two models with background µa of 0.2 (170) and 0.4 (169). A small absorber is put in the center of each model, with µa of 0.4 and 0.8, respectively. The early slope of the reflectance curve (−6.6 or −10) is bigger than the tail slope (−3 or −5.8), which may provide a clue for detection of the embedded object. The µa values calculated from tail slope (0.19 or 0.36 cm$^{-1}$) fits the theoretical value very well, suggesting the remote time-domain system can detect tissue absorption coefficients very accurately.

Figure 11:
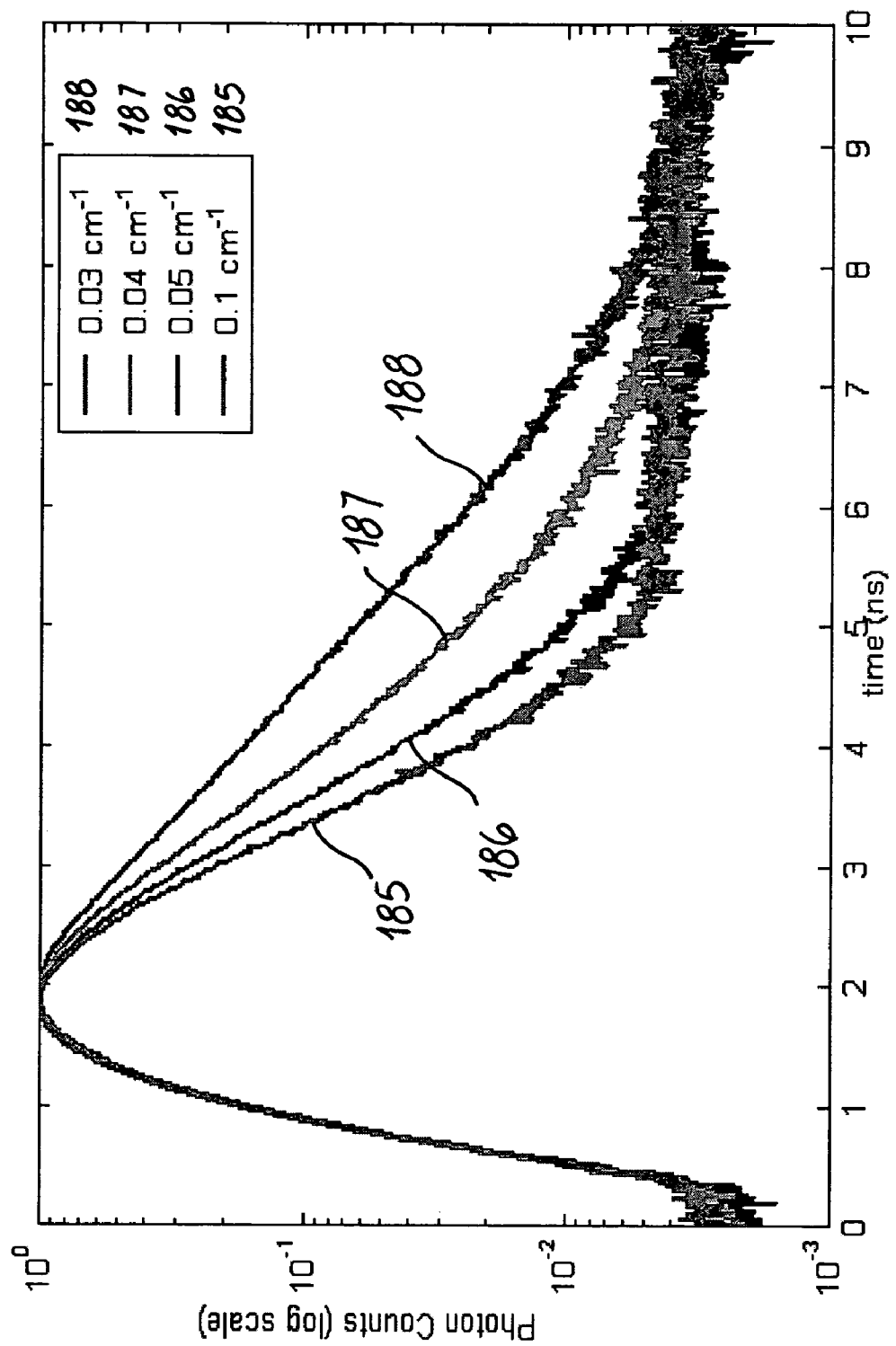
FIG. 11 shows a Monte Carlo simulation for a heterogeneous model.

FIG. 11 shows more of this data, where heterogeneous models, as suggested by the Monte Carlo simulations, are made with different models: a small absorber or fluorescence marker in a homogeneous phantom, for example. The figure shows remote detected time-resolved curves of backscattered light from tissue-like phantoms at 1M distance. The exact values of their absorption coefficient ($\mu_a$) are shown in the small box and the legends labeled 185, 186, 187 and 188. The slopes of these curves are proportional to $\mu_a$. This proves the remote TRS system able to measure unknown absorption coefficients of tissue. FIG. 11 illustrates that the equations for TRS spectroscopy previously derived by Patterson, Chance and Wilson apply to absorption coefficients from a model containing intarlipid at a $\mu_s$ of 10 cm$^{-1}$. The absorption constant was varied by serial additions of India ink, giving the four values of $\mu_a$ which are calculated to be exactly proportional to the model values. Since the model is homogeneous, the log slope is constant over a wide range of values; that is, remote detection has no effect on the measurements. These data also show the feasibility of using the remote, non-contact TRS system for biological tissue examination and imaging.

Other embodiments are within the following claims:
The invention claimed is:

1. An optical system for examination of breast tissue, comprising:
    a light source for generating a light beam of a wavelength in a visible to infra-red range to be introduced in the breast tissue spaced apart from said source;
    a scanning and irradiation system constructed to receive said generated light beam and irradiate a tissue surface over an area of the breast tissue to be examined by scanning said light beam, said scanning and irradiation system being spaced apart from the tissue area;
    a tissue tracking system constructed to track position of the tissue area;
    a light detector located away from the examined breast tissue and constructed to detect light that has migrated over scatter paths inside the examined breast tissue and exited inside the tissue; and
    a computer controlled system including electronics for controlling said light source, said light detector and said scanning and irradiation system, said computer controlled system being constructed to separate reflected photons from photons that have migrated deep inside the examined breast tissue over tissue scatter paths by timing operation of said light source and said light detector to prevent detection of the photons reflected from the tissue surface by the light detector.

2. The optical system of claim 1, further including a module constructed and arranged to deliver a chemical or pharmacological agent into the examined tissue.

3. The optical system of claim 2, wherein said wavelength of said light source is sensitive to said agent including ICG.

4. The optical system of claim 2, wherein said wavelength of said light source is sensitive to said agent including a fluorescent agent.

5. The optical system of claim 2, wherein said wavelength of said light source is sensitive to said agent including a pharmacological agent.

6. The optical system of claim 1, wherein said light source includes a pulsar constructed to generate pulses of an input waveform of duration on the order of a nanosecond or less, and wherein said light source is constructed to receive said pulses of said input waveform and is constructed to generate said light beam including light pulses of said input waveform.

7. The optical system of claim 6, wherein said computer controlled system includes an analyzer constructed to store over time signals corresponding to said detected pulse waveforms; and said computer is constructed to determine changes in shapes of said detected pulse waveforms relative to said input pulse waveform.

8. The optical system of claim 1 wherein said computer controlled system is constructed to calculate hemodynamic signal based on said optical data.

9. The optical system of claim 1 wherein said computer controlled system is constructed to calculate a spatial distribution of blood volume based on said optical data.

10. The optical system of claim 1 wherein said computer controlled system is constructed to calculate metabolic signal based on said optical data.

11. An optical method for examination of breast tissue, comprising:

generating a light beam of a wavelength in a visible to infra-red range from a light source;

receiving said generated light beam by a scanning and irradiation system being spaced apart from the breast tissue to be examined;

irradiating a tissue surface over an area of the examined breast tissue by scanning said light beam over a tissue area;

tracking the tissue area by a tracking system;

detecting by a light detector, located away from the examined biological tissue, light that has migrated over scatter paths inside the examined breast tissue and exited inside the tissue;

controlling operation of said light source and said light detector;

separating photons reflected from the surface from photons that have migrated inside the examined breast tissue to prevent detection of the reflected photons by the light detector or eliminating after detection the reflected photons in optical data detected by the light detector; and examining breast tissue using said optical data.

12. The method of claim 11 including performing molecular imaging for monitoring processes or pathways in cells located in the examined tissue.

13. The method of claim 11, wherein said detecting includes performing confocal detection from a selected depth of the examined tissue.

14. The method of claim 11, wherein said detecting includes detecting fluorescent light excited in and emanating from the examined tissue.

15. The method of claim 11 wherein the examining breast tissue includes human tissue.

16. The method of claim 11 wherein the examining breast tissue includes animal tissue.

17. The method of claim 11 further including tracking medical processes associated with progress of diseases and treatment.

18. The method of claim 11 further including evaluating a metabolite.

19. The method of claim 18, wherein said evaluating a metabolite includes a metabolite of a chemical agent.

20. The method of claim 18, wherein said evaluating a metabolite includes a metabolite of a pharmacological agent.

21. The method of claim 11 further including calculating hemodynamic signal based on said optical data.

22. The method of claim 11 further including calculating a spatial distribution of blood volume inside the examined tissue based on said optical data.

23. The method of claim 11 further including calculating metabolic signal based on said optical data.

24. An optical system for examination of breast tissue, comprising:

a light source for generating a light beam of a wavelength in a visible to infra-red range to be introduced in the breast tissue spaced apart from said source;

a scanning and irradiation system constructed to receive said generated light beam and irradiate a tissue surface over an area of the breast tissue to be examined by scanning said light beam, said scanning and irradiation system being spaced apart from the tissue area;

a tissue tracking system constructed to track position of the tissue area;

a light detector located away from the examined breast tissue and constructed to detect light that has migrated over scatter paths inside the examined breast tissue;

a computer controlled system including electronics for controlling said light source, said light detector and said scanning and irradiation system; and said computer controlled system eliminating after detection photons reflected from the surface in detected optical data from photons that have migrated deep inside the examined breast tissue over tissue scatter paths by Fourier transformation and producing optical data used for tissue examination.

25. The optical system of claim 24 further comprising a first oscillator constructed to generate a first carrier waveform at a first frequency on the order of $10^8$ Hz, said first frequency having a time characteristic compatible with the time delay of photon migration from an input port to a detection port;

said light source being coupled to said first oscillator and constructed to generate said light modulated by said first carrier waveform;

a phase detector constructed to determine change in waveform of the detected light relative to the waveform of the introduced light and measure therefrom the phase shift of said detected light at said wavelength, said phase-shifted light being indicative of scattering or absorptive properties of the examined tissue region; and said processor being arranged to form said data based on the measured phase shift.

26. The optical system of claim 25 further comprising a second oscillator constructed to generate a second waveform at a second frequency;

said light detector being a photomultiplier (PMT) arranged to receive a reference waveform at a reference frequency offset by a frequency on the order of $10^3$ Hz from said first frequency and to produce a signal, at said offset frequency, corresponding to said detected radiation; and said phase detector being adapted to compare, at said offset frequency, the detected radiation with the introduced radiation and to determine therefrom said phase shift.

27. The optical system of claim 24 further comprising:

an oscillator constructed to generate a first carrier waveform of a selected frequency compatible with time delay of photon migration from an input port to a detection port; said light source being connected to receive from said oscillator said carrier waveform and constructed to generate optical radiation modulated at said frequency;

a phase splitter connected to receive said carrier waveform from said oscillator and produce first and second reference phase signals of predefined substantially different phases;

first and second double balanced mixers connected to receive from said phase splitter said first and second reference phase signals, respectively, and connected to receive from said detector said detector signal and to produce therefrom a in-phase output signal and a quadrature output signal, respectively; and said processor being connected to said double balanced mixers and arranged to receive said in-phase output signal and said quadrature output signal and form therefrom said data set.

28. The optical system of claim 27 wherein said processor is arranged to calculate a phase shift ($\Theta_A$) between said light introduced at said input port and said light detected at said detection port prior to forming said data set.

29. The optical system of claim 27 wherein said processor is arranged to calculate an average migration pathlength of photons scattered in the examined tissue between said optical input port and said optical detection port prior to forming said data set.

30. The optical system of claim 29 wherein said processor further employs said pathlength in quantifying hemoglobin saturation (Y) of the examined tissue.

31. The optical system of claim 27 wherein said processor is arranged to calculate a signal amplitude ($A_\lambda$) determined as a square root of a sum of squares of said in-phase output signal and said quadrature output signal prior to forming said data set.

32. The optical system of claim 31 further comprising:
a narrow band detector connected to receive from said optical detector said detector signal and to produce a DC output signal therefrom; and said signal processor further determining a modulation index ($M_\lambda$) as a ratio of values of said signal amplitude and said signal amplitude plus said DC output signal.

33. The optical system of claim 24 wherein said computer controlled system is constructed to calculate hemodynamic signal based on said optical data.

34. The optical system of claim 24 wherein said computer controlled system is constructed to calculate a spatial distribution of blood volume based on said optical data.

35. The optical system of claim 24 wherein said computer controlled system is constructed to calculate metabolic signal based on said optical data.

* * * * *